US012778576B2

(12) United States Patent
Phillips et al.

(10) Patent No.: US 12,778,576 B2
(45) Date of Patent: *Nov. 3, 2026

(54) MAGNET-ASSISTED SUTURE GRASPER COMPRISING A SUTURE RETRIEVAL NEEDLE, A GRASPER FERRULE, A GRASPER MAGNET, AND A MAGNET WIRE

(71) Applicant: APPLIED MEDICAL TECHNOLOGY, INC., Brecksville, OH (US)

(72) Inventors: Grant Wesley Phillips, Richfield, OH (US); Steven Alfred Soeder, North Royalton, OH (US); George J. Picha, Brecksville, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/129,504

(22) PCT Filed: Nov. 18, 2022

(86) PCT No.: PCT/US2022/050444

§ 371 (c)(1),
(2) Date: May 13, 2025

(87) PCT Pub. No.: WO2024/107205

PCT Pub. Date: May 23, 2024

(65) Prior Publication Data

US 2026/0102153 A1 Apr. 16, 2026

(51) Int. Cl.
*A61B 17/04* (2006.01)
*A61B 17/00* (2006.01)

(52) U.S. Cl.
CPC .................... *A61B 17/0469* (2013.01); *A61B 2017/00876* (2013.01)

(58) Field of Classification Search
CPC ........... A61B 17/0469; A61B 17/0483; A61B 2017/00876; A61B 2017/00358
See application file for complete search history.

(56) References Cited

U.S. PATENT DOCUMENTS 1,212,870 A 1/1917 Zolper
3,762,418 A 10/1973 Wasson
(Continued)

FOREIGN PATENT DOCUMENTS

EP 778004 B1 3/2003
JP 2006-25932 A 2/2006
(Continued)

OTHER PUBLICATIONS

Medacta International, "FastShuttle Suture Passer System Product Catalog," pp. 1-8 (2019), available at https://media.medacta.com/media/pc-99116sm180-rev-00.pdf, last accessed Sep. 29, 2022.
(Continued)

*Primary Examiner* — Katherine M Shi
*Assistant Examiner* — Mohammed S Adam
(74) *Attorney, Agent, or Firm* — EVENTIDE LAW LLC

(57) ABSTRACT

A magnet-assisted suture grasper for grasping a magnetic suture is provided. The magnet-assisted suture grasper includes a suture retrieval needle, a retriever tube, a grasper ferrule, a grasper member, a grasper magnet, and a magnet wire. Translation of the retriever tube within a needle lumen of the suture retrieval needle in a first direction causes the grasper member to move from a first position to a second position, thereby exposing the grasper magnet from the needle lumen and allowing contact between the grasper magnet and a magnetic suture attracted thereto. Translation of the retriever tube within the needle lumen in a second direction opposite the first direction causes the grasper member to move from the second position to the first
(Continued)

position, thereby sequestering the grasper magnet and grasping the magnetic suture within the needle lumen.

33 Claims, 48 Drawing Sheets

(56) References Cited

U.S. PATENT DOCUMENTS

| | | | |
|---|---|---|---|
| 4,115,015 | A | 9/1978 | Torii |
| 4,266,881 | A | 5/1981 | Rubens |
| 4,540,300 | A | 9/1985 | Midorikawa |
| 4,560,298 | A | 12/1985 | Oki et al. |
| D292,297 | S | 10/1987 | Bingham |
| 4,711,592 | A | 12/1987 | Gregory |
| 4,759,650 | A | 7/1988 | Granoff |
| 4,969,764 | A | 11/1990 | Gregory |
| 4,986,682 | A | 1/1991 | Lu |
| 5,022,773 | A | 6/1991 | Waldinger et al. |
| 5,026,190 | A | 6/1991 | Longarzo |
| D321,207 | S | 10/1991 | Granoff |
| D321,718 | S | 11/1991 | Ambasz |
| 5,131,775 | A | 7/1992 | Chen |
| 5,152,626 | A | 10/1992 | Eppler |
| 5,174,814 | A | 12/1992 | Burwell et al. |
| 5,364,365 | A | 11/1994 | Wortrich |
| 5,501,692 | A | 3/1996 | Riza |
| 5,651,626 | A | 7/1997 | Chen |
| 5,653,716 | A | 8/1997 | Malo et al. |
| 5,722,981 | A | 3/1998 | Stevens |
| 5,756,941 | A | 5/1998 | Snell |
| 5,817,111 | A | 10/1998 | Riza |
| 5,824,009 | A | 10/1998 | Fukuda et al. |
| 5,864,490 | A | 1/1999 | Van Bost |
| 5,928,250 | A | 7/1999 | Koike et al. |
| 5,997,204 | A | 12/1999 | Ducrocq |
| 6,159,224 | A | 12/2000 | Yoon |
| 6,213,661 | B1 | 4/2001 | Coon |
| 6,318,921 | B1 | 11/2001 | Craine |
| D457,917 | S | 5/2002 | Traut et al. |
| 6,450,721 | B1 | 9/2002 | D'Amico et al. |
| 6,547,470 | B2 | 4/2003 | Legg |
| 6,551,304 | B1 | 4/2003 | Whalen et al. |
| 6,719,765 | B2 | 4/2004 | Bonutti |
| D494,218 | S | 8/2004 | Anand |
| D495,001 | S | 8/2004 | Anand |
| 6,830,402 | B2 | 12/2004 | Sunatori |
| 6,981,812 | B1 | 1/2006 | Hsieh |
| D537,878 | S | 3/2007 | Anand |
| D542,349 | S | 5/2007 | Anand |
| 7,226,229 | B1 | 6/2007 | Register |
| D548,788 | S | 8/2007 | Anand |
| 7,334,954 | B1 | 2/2008 | Rentz |
| D571,400 | S | 6/2008 | Anand |
| D574,429 | S | 8/2008 | Kusaba et al. |
| D591,136 | S | 4/2009 | Cheldin |
| D616,497 | S | 5/2010 | Shiina |
| 7,887,212 | B2 | 2/2011 | Liu |
| 7,948,648 | B2 | 5/2011 | Silverbrook et al. |
| 7,969,587 | B2 | 6/2011 | Silverbrook |
| 8,031,177 | B2 | 10/2011 | Lapstun et al. |
| 8,087,841 | B2 | 1/2012 | Liu |
| 8,094,325 | B2 | 1/2012 | Silverbrook |
| 8,182,167 | B2 | 5/2012 | Liu |
| 8,240,931 | B1 | 8/2012 | Collins |
| 8,262,241 | B2 | 9/2012 | Liu |
| 8,267,947 | B2 | 9/2012 | Pantages et al. |
| 8,287,204 | B2 | 10/2012 | Silverbrook et al. |
| 8,297,868 | B2 | 10/2012 | Underwood et al. |
| 8,360,669 | B2 | 1/2013 | Underwood et al. |
| 8,414,210 | B2 | 4/2013 | Silverbrook et al. |
| 8,632,270 | B2 | 1/2014 | Liu |
| 8,702,753 | B2 | 4/2014 | Mikkaichi et al. |
| D725,112 | S | 3/2015 | Bo |
| 9,351,721 | B2 | 5/2016 | Auerbach et al. |
| D758,988 | S | 6/2016 | An et al. |
| 9,474,572 | B2 | 10/2016 | Lowry |
| 9,770,238 | B2 | 9/2017 | Bonutti |
| 10,245,021 | B2 | 4/2019 | Phillips et al. |
| 10,299,786 | B2 | 5/2019 | Levine et al. |
| 10,343,445 | B2 | 7/2019 | Wu |
| 10,503,284 | B1 | 12/2019 | Chang et al. |
| 10,960,705 | B1 | 3/2021 | Yu |
| 10,974,540 | B1 | 4/2021 | Yu |
| 11,241,904 | B2 | 2/2022 | Yu |
| 11,672,530 | B2 | 6/2023 | Williams et al. |
| 11,723,655 | B2 | 8/2023 | Phillips et al. |
| 11,839,373 | B2 | 12/2023 | Phillips et al. |
| 12,114,854 | B2 | 10/2024 | Phillips et al. |
| 2003/0139752 | A1 | 7/2003 | Pasricha et al. |
| 2003/0216613 | A1 | 11/2003 | Suzuki et al. |
| 2004/0116963 | A1 | 6/2004 | Lattouf |
| 2005/0154403 | A1 | 7/2005 | Sauer et al. |
| 2006/0069398 | A1 | 3/2006 | Suzuki et al. |
| 2007/0118153 | A1 | 5/2007 | Funamura et al. |
| 2008/0154286 | A1 | 6/2008 | Abbott et al. |
| 2008/0243148 | A1 | 10/2008 | Mikkaichi et al. |
| 2008/0269783 | A1 | 10/2008 | Griffith |
| 2009/0224561 | A1 | 9/2009 | Jackson, III |
| 2009/0318958 | A1 | 12/2009 | Ochiai |
| 2010/0280530 | A1 | 11/2010 | Hashiba |
| 2011/0015653 | A1 | 1/2011 | Bogart et al. |
| 2011/0112555 | A1 | 5/2011 | Overes et al. |
| 2011/0118757 | A1 | 5/2011 | Pierce |
| 2011/0144666 | A1 | 6/2011 | Egle et al. |
| 2011/0245850 | A1 | 10/2011 | van der Burg et al. |
| 2012/0277766 | A1 | 11/2012 | Ferree |
| 2013/0074849 | A1 | 3/2013 | Rousseau et al. |
| 2013/0317291 | A1 | 11/2013 | Yamamoto |
| 2015/0038976 | A1 | 2/2015 | Roschak et al. |
| 2015/0039027 | A1 | 2/2015 | Broom et al. |
| 2015/0100071 | A1 | 4/2015 | Phillips et al. |
| 2015/0327850 | A1 | 11/2015 | Kostrzewski |
| 2016/0324517 | A1 | 11/2016 | Liu |
| 2017/0049439 | A1 | 2/2017 | Keyser et al. |
| 2018/0049733 | A1 | 2/2018 | Zhao et al. |
| 2018/0296201 | A1 | 10/2018 | Holsten et al. |
| 2019/0076141 | A1 | 3/2019 | Liu |
| 2019/0133591 | A1 | 5/2019 | Dobashi et al. |
| 2020/0214695 | A1 | 7/2020 | Liu |
| 2020/0360017 | A1 | 11/2020 | Liu |
| 2021/0045735 | A1 | 2/2021 | Nobles et al. |
| 2021/0059667 | A1 | 3/2021 | Williams et al. |
| 2022/0104802 | A1 | 4/2022 | Liu |
| 2022/0104803 | A1 | 4/2022 | Desjardin et al. |
| 2022/0125426 | A1 | 4/2022 | Khanicheh et al. |
| 2023/0141192 | A1 | 5/2023 | Phillips et al. |
| 2024/0057998 | A1 | 2/2024 | Phillips et al. |

FOREIGN PATENT DOCUMENTS

| | | | |
|---|---|---|---|
| JP | 2010514467 | A | 5/2010 |
| WO | 2010129312 | A2 | 11/2010 |
| WO | 2011025767 | A1 | 3/2011 |
| WO | 2022245819 | A1 | 11/2022 |
| WO | 2022245822 | A1 | 11/2022 |

OTHER PUBLICATIONS

Imhoff, J., "Performing Incision-Less Hernia Repair for Kids," Michigan Health, pp. 1-5 (Feb. 17, 2020), available at https://labblog.uofmhealth.org/industry-dx/performing-incision-less-hernia-repairs-for-kids, last accessed Feb. 16, 2022.

Johnson, K.N., et al., "Ultrasound-Guided Pediatric Inguinal Hernia Repair," Journal of Pediatric Surgery, vol. 56, pp. 1240-1245 (epublished Mar. 11, 2021).

Young, R., "Rethinking the Simple Suture Passer," Orthopedics This Week, RRY Publications, pp. 1-8 (Apr. 29, 2016), available at https://ryortho.com/2016/04/rethinking-the-simple-suture-passer/, last accessed Apr. 25, 2022.

OrthoMed, Inc., "Suture Passer with Crochet Hook," pp. 1-2 (2022), available at https://www.orthomedinc.com/surgical-instruments/suture-passer-with-crochet-hook, last accessed Sep. 29, 2022.

(56) References Cited

OTHER PUBLICATIONS

Mediflex Surgical Products, "5mm Curved Maryland Dissector with Cross Serrations," pp. 1-4 (2022), available at https://mediflex.com/products/5mm-curved-maryland-dissector, last accessed Sep. 29, 2022.
CooperSurgical, Inc., "Carter-Thomason CloseSure System—Port Site Closure," pp. 1-2 (2022), available at https://www.coopersurgical.com/detail/carter-thomason-closesure-system-port-site-closure/, last accessed Sep. 29, 2022.
Endoscopy Superstore, "Arthro-Pro Suture Manipulator Grasper," Manufacturer: Advanced Endoscopy Devices, pp. 1-2 (2022), available at https://www.endoscopysuperstore.com/arthro-pro-suture-manipulator-grasper.aspx#, last accessed Sep. 29, 2022.
Arthrex, Inc., "Back Grasper with SR Handle," pp. 1-3 (2022), available at https://www.arthrex.io/products/AR-12531SR, last accessed Sep. 29, 2022.
Arthrex, Inc., "CrabClaw," pp. 1-3 (2022), available at https://www.arthrex.com/shoulder/crabclaw, last accessed Sep. 29, 2022.
Smith & Nephew, "Meniscus Mender II," pp. 1-2 (2022), available at https://www.smith-nephew.com/professional/ products/all-products/meniscus-mender-ii/, last accessed Sep. 29, 2022.
DePuy Synthes, "Chia Percpasser Suture Passer," pp. 1-5 (2021), available at https://www.jnjmedtech.com/en- US/product/chia-percpasserr-suture-passer, last accessed Sep. 29, 2022.
DePuy Synthes, "Ideal Suture Shuttle," pp. 1-4 (2021), available at https://www.jnjmedtech.com/en-US/product/ideal-suture-shuttle, last accessed Sep. 29, 2022.
Arthrex, Inc., "SutureLasso," pp. 1-5 (2022), available at https://www.arthrex.com/shoulder/suturelassos, last accessed Sep. 29, 2022.
Medtronic, "Endoscopic Suturing Devices," pp. 1-3 (2022), available at https://www.medtronic.com/covidien/en-us/products/hand-instruments-ligation/endoscopic-suturing-devices.html, last accessed Sep. 29, 2022.
Zimmer Biomet, "SpeedSnare Surgical Suture Passer," pp. 1-7 (2022), available at https://www.zimmerbiomet.com/en/products-and-solutions/specialties/sports-medicine/speedsnare-surgical-suture-passer.html, last accessed Sep. 29, 2022.
Wikipedia, "Veress needle," pp. 1-3 (Apr. 3, 2022), available at https://en.wikipedia.org/wiki/Veress_needle, last accessed Sep. 29, 2022.
CooperSurgical, Inc., "Carter-Thomason II Port Site Closure System," pp. 1-2 (2022), available at https://www.coopersurgical.com/detail/carter-thomason-ii-port-site-closure-system/, last accessed Sep. 29, 2022.
Mediflex Surgical Products, "SafePass Suture Grasper," pp. 1-4 (2022), available at https://mediflex.com/products/safepass%E2%84%A2-suture-grasper-box-of-10-sterile, last accessed Sep. 29, 2022.
Zimmer Biomet, "Dragon Tongue Suture Passer," pp. 1-5 (2022), available at https://www.zimmerbiomet.com/en/products-and-solutions/specialties/sports-medicine/dragon-tongue-suture-passer.html, last accessed Sep. 29, 2022.
Medtronic, "Port-Site Closure Devices," pp. 1-4 (2022), available at https://www.medtronic.com/covidien/en-us/products/trocars-access/port-site-closure-devices.html; last accessed Sep. 20, 2022.
International Search Report and Written Opinion of PCT/US2022/050444, mailed Mar. 6, 2023, pp. 1-19.
Owens, J., "How Does a Clicky Pen Work?" You Tube, pp. 1-8 (2022), available at https://www.youtube.com/watch?v=Zv5Qa2kGL04, last accessed Sep. 29, 2022.
Notice of Reasons for Rejection, Japanese Pat. Appl. No. 2025-528587, issued Jul. 28, 2026, pp. 1-5 (including English translation).

MAGNET-ASSISTED SUTURE GRASPER COMPRISING A SUTURE RETRIEVAL NEEDLE, A GRASPER FERRULE, A GRASPER MAGNET, AND A MAGNET WIRE

FIELD OF THE INVENTION

The invention relates to a magnet-assisted suture grasper for grasping a magnetic suture, and more particularly to a magnet-assisted suture grasper for grasping a magnetic suture comprising a suture retrieval needle, a retriever tube, a grasper ferrule, a grasper member, a grasper magnet, and a magnet wire.

BACKGROUND OF THE INVENTION

Suture passing is required in many surgical procedures. A suture passer is a surgical instrument which provides a means of delivery and/or retrieval of a suture through some bodily tissue. There are many existing instruments on the market which utilize a mechanical solution to secure a suture for passing.

Increasingly, minimally invasive techniques are being employed over open surgery due to reduction in risk, faster recovery time, and generally better cosmesis. Minimally invasive techniques typically make use of a scope and specialized tools that can be inserted through existing openings of a patient (e.g., via endoscope, colonoscope, etc.) or artificially created openings of the patient (e.g., via laparoscope, arthroscope, etc.) to gain access to the targeted intracorporeal working space.

Working with indirect visualization of surgical instruments through a scope presents a significant technical challenge to the use of suture passers for retrieval. Retrieving a suture using a typical suture passer requires precise positioning and careful manipulation of the suture passer to position one or more grasping elements of the suture passer around the suture. The suture passer must be held relatively steady in position while the grasping elements are closed about the suture, capturing the suture and holding it firmly so it can be retrieved. Skillful manipulation in this manner is hampered by the fact that most scopes employ a single camera and present a two-dimensional image to the suture passer operator and thus do not provide stereoscopic imaging. The lack of stereoscopic imaging hampers the operator's ability to perceive depth, which increases the level of difficulty associated with precisely positioning the grasping elements around the suture. While three-dimensional imaging systems exist, they are expensive and to date remain relatively rare in the field.

Most existing suture passer designs utilize a multi-arm design, where two or more arms are opened and brought around a suture, then closed around the suture to capture it. The arms may be separate, creating a pincer-style grasper with jaws to grasp a suture, or they may be connected, forming a snare-type grasper forming an eye through which a suture can be threaded.

Unfortunately, regardless of the arm design, these devices require precise positioning to get the jaws of the grasper around the suture, or to thread the suture through the eye of the snare before the suture can be captured. As noted, this is difficult under indirect visualization because camera systems for indirect visualization are typically non-stereoscopic. Without a three-dimensional image, a surgeon must rely on visual cues to judge the instrument position and depth, which makes it difficult to get the instrument positioned properly. Once the instrument is in position, the surgeon then needs to hold the instrument and the suture very steady while attempting to close the grasper around the suture. The long moment arm created by the length of the instrument magnifies even very minor movements, so that a small movement can bring the two components out of alignment. Failed attempts at grasping a suture can extend procedure times and lead to frustration in the operating room.

A magnetic U-stitch suturing device intended to address these difficulties has been disclosed in U.S. Pat. No. 10,245,021. The magnetic U-stitch suturing device is made of two hypodermic needles allowing one or more sutures, at the same time, and a retrieval probe to be advanced into a cavity, such as a stomach cavity, of a patient. The one or more sutures can be magnetic sutures, each including a suture magnet, as described in U.S. Pub. No. 2021/0059667. Both the suture and retrieval probe comprise magnets of opposite polarities on their leading ends. Thus, after the suture and retrieval probe are inside the stomach cavity, the suture and retrieval probe may mate and the suture may be transferred from one hypodermic needle to the other using magnetic attraction. In doing so, the suture forms a loop through the stomach. Once removed, this loop, having two ends that are positioned outside the patient's body, can be pulled tight in order to pull the stomach wall closer to the surface of the patient's body. With the stomach wall close to the surface of the patient's body, it is easier to insert a gastrostomy device.

Unfortunately, certain procedures, such as inguinal hernia repair through high ligation of the patent processus vaginalis, require passing of a suture in a space, e.g., a peritoneal cavity, that is not sufficiently large to permit advancement of the two hypodermic needles of the magnetic U-stitch suturing device simultaneously.

Other suture instruments and/or sutures including magnets also have been disclosed. For example, U.S. Pat. No. 10,299,786 discloses a suture insertion device utilizing small gauge needles for threading one or more sutures through subcutaneous tissue. The suture insertion device can include a magnetic capture mechanism for contacting a magnetically attractive strand in transverse alignment. U.S. Pat. Nos. 6,719,765 and 9,770,238 disclose instruments for passing a medical implement through tissue with magnetic forces. U.S. Pat. No. 6,551,304 discloses an apparatus and method for retrieving a remotely located device equipped with a magnetic coupler. U.S. Pat. No. 8,702,753 and U.S. Pub. No. 2008/0243148 disclose sutures to which magnetic anchors are attached. U.S. Pub. No. 2020/0360017 discloses a suturing apparatus in which a suture thread may be automatically passed between a needle and a transfer tube. The suturing apparatus can include electromagnetic coils to engage and release a suture from the system. U.S. Pub. No. 2020/0214695 discloses a suturing system including a forceps arm and a suture that may be magnetic to thus engage with each other. U.S. Pub. No. 2022/0104802 discloses a suturing system including a rod having a magnetic tube extending from an end thereof and a magnetic needle having an end attracted into the tube to magnetically engage therewith. U.S. Pub. No. 2021/0059667 discloses a magnetic suture that has a ferrule with a tapered region in which a knotted suture is provided and secured with an adhesive and a straight region in which a magnet is provided.

Applied Medical Technology, Inc.'s international application PCT/US2022/029627, filed May 17, 2022, describes a magnet-assisted suture grasper including a suture retrieval needle, a retriever body, a grasper wire, a grasper arm, and a grasper magnet. Translation of the retriever body within a needle lumen of the suture retrieval needle in a first direction causes the grasper arm to move from a first position to a second position, thereby exposing the grasper magnet from the needle lumen and allowing contact between the grasper magnet and a magnetic suture attracted thereto. Translation of the retriever body within the needle lumen in a second direction opposite the first direction causes the grasper arm to move from the second position to the first position, thereby sequestering the grasper magnet and grasping the magnetic suture within the needle lumen.

Applied Medical Technology, Inc.'s international application PCT/US2022/029631, filed May 17, 2022, describes a magnet-assisted suture grasper including a suture retrieval needle, a retriever body, a grasper arm, and a grasper magnet. Another magnet-assisted suture grasper including a handle, a stem, first and second grasper jaws, a grasper magnet, and an actuator body also is described.

Improved suture passers that reduce the technical difficulty associated with capturing and retrieving sutures under indirect non-stereoscopic visualization are needed.

BRIEF SUMMARY OF THE INVENTION

A magnet-assisted suture grasper for grasping a magnetic suture is disclosed. The magnet-assisted suture grasper comprises: (a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis; (b) a retriever tube having a proximal hole, a distal hole, and a retriever tube lumen extending therebetween, the retriever tube being partially disposed within the needle lumen and translatable therein along the needle body axis, the proximal hole of the retriever tube being in fluid communication with the distal hole of the needle body through the retriever tube lumen and the needle lumen; (c) a grasper ferrule comprising a proximal end, a distal end, and a ferrule body extending therebetween, the ferrule body having a proximal hole, a distal hole, and a ferrule lumen extending therebetween, the grasper ferrule being fixedly disposed within the retriever tube; (d) a grasper member comprising a proximal portion, an intermediate portion, and a distal portion, the grasper member extending distally from the grasper ferrule and being reversibly moveable with respect to the needle lumen between a first position and a second position; (e) a grasper magnet being disposed adjacent the intermediate portion of the grasper member, the magnet-assisted suture grasper sequestering the grasper magnet within the needle lumen when the grasper member is in the first position and exposing the grasper magnet from the needle lumen when the grasper member is in the second position; and (f) a magnet wire having a proximal portion and a distal portion, the magnet wire extending distally from the grasper ferrule and the grasper magnet being fixedly attached to the distal portion of the magnet wire, either directly or indirectly. The distal portion of the grasper member extends further distally than the grasper magnet. Translation of the retriever tube within the needle lumen in a first direction along the needle body axis causes the grasper member to move from the first position to the second position, thereby exposing the grasper magnet and allowing contact between the grasper magnet and a magnetic suture attracted thereto. Translation of the retriever tube within the needle lumen in a second direction opposite the first direction along the needle body axis causes the grasper member to move from the second position to the first position, thereby sequestering the grasper magnet and grasping the magnetic suture within the needle lumen.

In some embodiments, the suture retrieval needle is a hypodermic needle.

In some embodiments, the suture retrieval needle is straight, the needle body axis thereby being straight.

In some embodiments, the suture retrieval needle is curved, the needle body axis thereby being curved.

In some embodiments, the suture retrieval needle has a sharp tip.

In some embodiments, the magnet-assisted suture grasper further comprises a proximal hub.

In some embodiments, the retriever tube comprises stainless steel.

In some embodiments, the retriever tube lumen is the only lumen of the retriever tube.

In some embodiments, translation of the retriever tube within the needle lumen is limited to a straight path as the translation of the retriever tube causes the grasper member to move between the first and second positions.

In some embodiments, the grasper ferrule has been crimped onto the grasper member and the magnet wire, with the proximal portion of the grasper member and the proximal portion of the magnet wire being disposed within the ferrule lumen of the grasper ferrule; and the retriever tube has been crimped onto the grasper ferrule, with the grasper ferrule, the proximal portion of the grasper member, and the proximal portion of the magnet wire being disposed within the retriever tube lumen.

In some embodiments, the retriever tube has been crimped onto the grasper ferrule, the proximal portion of the grasper member, and the proximal portion of the magnet wire, with the grasper ferrule, the proximal portion of the grasper member, and the proximal portion of the magnet wire being disposed within the retriever tube lumen, and with the proximal portion of the grasper member and the proximal portion of the magnet wire being disposed adjacent the grasper ferrule and not within the ferrule lumen of the grasper ferrule.

In some embodiments, the grasper member is more flexible than the needle body.

In some embodiments, the grasper member comprises: (i) a grasper wire having a proximal end and a distal end, and (ii) a grasper arm comprising a proximal end, a proximal-to-intermediate portion, a distal portion, and a distal end; the grasper wire is fixedly disposed within the grasper ferrule, or adjacent the grasper ferrule and not within the ferrule lumen of the grasper ferrule; the grasper wire extends distally from the ferrule lumen; the grasper arm extends from the distal end of the grasper wire and is reversibly moveable between the first position and the second position; and the grasper magnet is disposed adjacent the proximal-to-intermediate portion of the grasper arm.

In some of these embodiments, the grasper arm is integral to the grasper wire.

Also in some of these embodiments, the grasper member further comprises an enlarged distal terminus at the distal end of the grasper arm; the grasper arm is reversibly moveable between the first position and the second position based on translation of the grasper arm from inside of the needle lumen to outside of the needle lumen through the distal hole of the needle body; and the enlarged distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

Also in some of these embodiments, the grasper member is a first grasper member; the grasper wire is a first grasper wire; the grasper arm is a first grasper arm; the magnet-assisted suture grasper further comprises a second grasper member comprising: (a) a second grasper wire having a proximal end and a distal end, being fixedly disposed within the retriever tube, and extending distally therefrom; and (b) a second grasper arm comprising a proximal end, a proximal-to-intermediate portion, a distal portion, and a distal end, the second grasper arm extending from the distal end of the second grasper wire and being reversibly moveable between the first position and the second position; the first and second grasper arms are connected at their distal ends, thereby forming a grasper arm loop; the first and second grasper members further comprise an enlarged distal terminus at the distal ends of the first and second grasper arms; the grasper arm loop is reversibly moveable between the first position and the second position based on translation of the grasper arm loop from inside of the needle lumen to outside of the needle lumen through the distal hole of the needle body; the grasper arm loop circumscribes an area sufficiently large, and the enlarged distal terminus has a size sufficiently small, to allow contact between the grasper magnet and a suture magnet of a magnetic suture attracted thereto when the grasper arm loop is in the second position; the enlarged distal terminus has a size sufficiently small to allow a suture of the magnetic suture to pass when the grasper arm loop is in the first position; and the enlarged distal terminus has a size sufficiently large to block the suture magnet of the magnetic suture from exiting the needle lumen through the distal hole of the needle body when the grasper arm loop is in the first position.

Also in some of these embodiments, the grasper arm is formed from a flat wire having a rectangular cross-section; the grasper member further comprises an angled distal terminus at the distal end of the grasper arm; the grasper arm is reversibly moveable between the first position and the second position based on translation of the grasper arm from inside of the needle lumen to outside of the needle lumen through the distal hole of the needle body; and the angled distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position. In some examples of these embodiments, the angled distal terminus comprises a hook. Also in some examples of these embodiments, the angled distal terminus fills 80% or more of an area of the distal hole of the needle body when the grasper arm is in the first position.

In some embodiments, the grasper member comprises a grasper arm comprising a proximal end, a proximal-to-intermediate portion, a distal portion, and a distal end; the grasper arm is integral to the grasper ferrule; and the grasper magnet is disposed adjacent the proximal-to-intermediate portion of the grasper arm.

In some of these embodiments, the grasper ferrule and the grasper arm are formed from a flat wire having a rectangular cross-section; the grasper ferrule comprises opposing first and second portions of the flat wire that have been folded inwardly toward each other, thereby forming the grasper ferrule; the grasper member further comprises an angled distal terminus at the distal end of the grasper arm; the grasper arm is reversibly moveable between the first position and the second position based on translation of the grasper arm from inside of the needle lumen to outside of the needle lumen through the distal hole of the needle body; and the angled distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position. In some examples of these embodiments, the angled distal terminus comprises a hook. Also in some examples of these embodiments, the angled distal terminus fills 80% or more of an area of the distal hole of the needle body when the grasper arm is in the first position.

Also in some of these embodiments, the grasper ferrule and the grasper arm are formed from a cut tube comprising a cylindrical portion and a semi-cylindrical portion; the cylindrical portion of the cut tube comprises the grasper ferrule; the semi-cylindrical portion of the cut tube comprises the grasper arm; the grasper member further comprises an angled distal terminus at the distal end of the grasper arm; the grasper arm is reversibly moveable between the first position and the second position based on translation of the grasper arm from inside of the needle lumen to outside of the needle lumen through the distal hole of the needle body; and the angled distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position. In some examples of these embodiments, the angled distal terminus comprises a hook. Also in some examples of these embodiments, the angled distal terminus fills 80% or more of an area of the distal hole of the needle body when the grasper arm is in the first position.

Also in some of these embodiments, the grasper ferrule has been crimped onto the magnet wire with the proximal portion of the magnet wire being disposed within the ferrule lumen of the grasper ferrule; and the retriever tube has been crimped onto the grasper ferrule with the grasper ferrule and the proximal portion of the magnet wire being disposed within the retriever tube lumen.

Also in some of these embodiments, the retriever tube has been crimped onto the grasper ferrule and the proximal portion of the magnet wire, with the grasper ferrule and the proximal portion of the magnet wire being disposed within the retriever tube lumen, and with the proximal portion of the magnet wire being disposed adjacent the grasper ferrule and not within the ferrule lumen of the grasper ferrule.

In some embodiments, the magnet wire further comprises a magnet wire distal terminus, the magnet-assisted suture grasper further comprises a magnet ferrule fixedly attached to the magnet wire distal terminus, and the grasper magnet is fixedly attached to the magnet ferrule.

In some embodiments, the magnet-assisted suture grasper further comprises a lock mechanism that can be reversibly engaged to prevent translation of the retriever tube within the needle lumen in the first direction and/or the second direction. In some of these embodiments, the lock mechanism can be reversibly engaged in a first setting that prevents translation of the retriever tube within the needle lumen in the first direction but not the second direction when the distal end of the grasper arm is inside the needle lumen and reversibly engaged in a second setting that prevents translation of the retriever tube within the needle lumen in the first direction but not the second direction when the grasper magnet is outside of the needle lumen. In some examples of these embodiments, maintaining the lock mechanism in the first setting or the second setting does not require energy input.

A system for passing a magnetic suture also is disclosed. The system comprises the magnet-assisted suture grasper. The system also comprises a magnetic suture comprising a suture magnet and a suture extending from the suture magnet.

BRIEF DESCRIPTION OF THE DRAWINGS

These and other features, aspects, and advantages of the present disclosure are better understood when the following detailed description is read with reference to the accompanying drawings, which are as follows.

FIG. 84 also is a side view of a distal portion of a magnet-assisted suture grasper that comprises only one grasper arm and only one grasper wire, in which the one grasper arm is integral to the one grasper wire.

FIG. 119 is a side view of the second alternative embodiment of the flat-wire grasper member having an angled distal terminus including a hook and the suture retrieval needle, the grasper magnet, and the magnet wire of FIG. 118.

FIG. 120 is a top view of the second alternative embodiment of the flat-wire grasper member having an angled distal terminus including a hook and the suture retrieval needle, the grasper magnet, and the magnet wire of FIG. 118.

FIG. 121 is a bottom view of the second alternative embodiment of the flat-wire grasper member having an angled distal terminus including a hook and the suture retrieval needle, the grasper magnet, and the magnet wire of FIG. 118.

FIG. 122 is a perspective view of the second alternative embodiment of the flat-wire grasper member having an angled distal terminus including a hook and the suture retrieval needle, the grasper magnet, and the magnet wire of the magnet-assisted suture grasper of FIG. 1. The flat-wire grasper member is in the first position.

FIG. 123 is a perspective view of a third alternative embodiment of the flat-wire grasper member having an angled distal terminus including a hook and the suture retrieval needle, the grasper magnet, and the magnet wire of the magnet-assisted suture grasper of FIG. 1. The flat-wire grasper member is in the second position.

FIG. 124 is a side view of the third alternative embodiment of the flat-wire grasper member having an angled distal terminus including a hook and the suture retrieval needle, the grasper magnet, and the magnet wire of FIG. 123.

FIG. 125 is a top view of the third alternative embodiment of the flat-wire grasper member having an angled distal terminus including a hook and the suture retrieval needle, the grasper magnet, and the magnet wire of FIG. 123.

FIG. 126 is a bottom view of the third alternative embodiment of the flat-wire grasper member having an angled distal terminus including a hook and the suture retrieval needle, the grasper magnet, and the magnet wire of FIG. 123.

FIG. 127 is a perspective view of the third alternative embodiment of the flat-wire grasper member having an angled distal terminus including a hook and the suture retrieval needle, the grasper magnet, and the magnet wire of the magnet-assisted suture grasper of FIG. 1. The flat-wire grasper member is in the first position.

FIG. 128 is a perspective view of a fourth alternative embodiment of the flat-wire grasper member having an angled distal terminus including a hook and the suture retrieval needle, the grasper magnet, and the magnet wire of the magnet-assisted suture grasper of FIG. 1. The flat-wire grasper member is in the second position.

FIG. 129 is a side view of the fourth alternative embodiment of the flat-wire grasper member having an angled distal terminus including a hook and the suture retrieval needle, the grasper magnet, and the magnet wire of FIG. 128.

FIG. 130 is a top view of the fourth alternative embodiment of the flat-wire grasper member having an angled distal terminus including a hook and the suture retrieval needle, the grasper magnet, and the magnet wire of FIG. 128.

Figure 128:
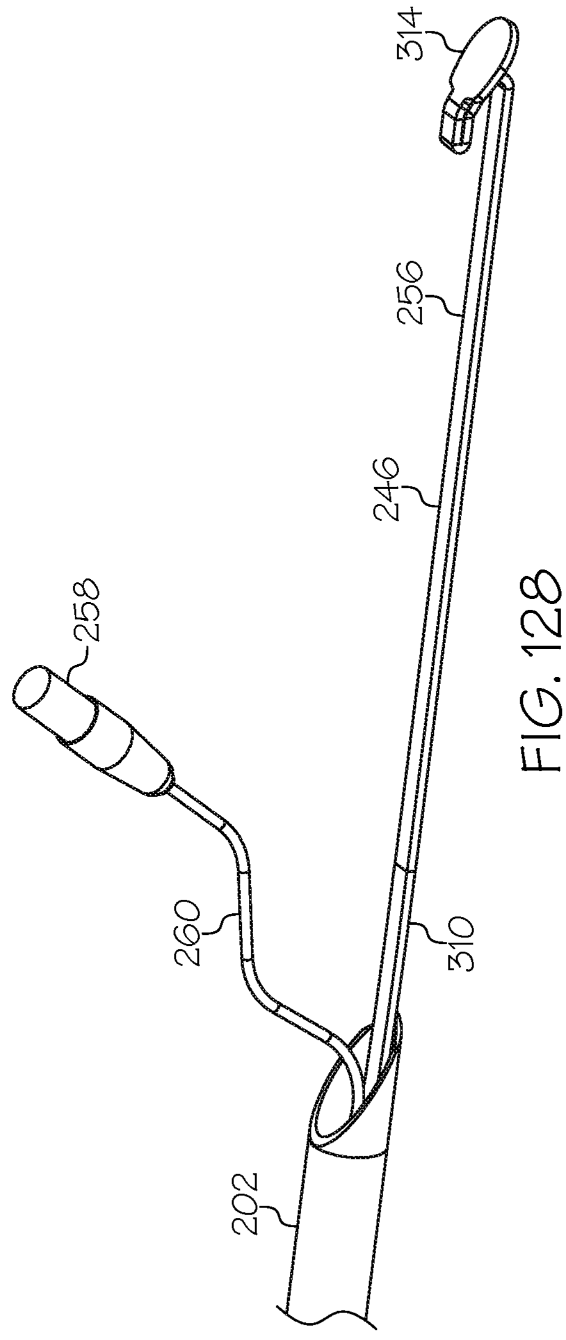
Figures 129, 130, 131:
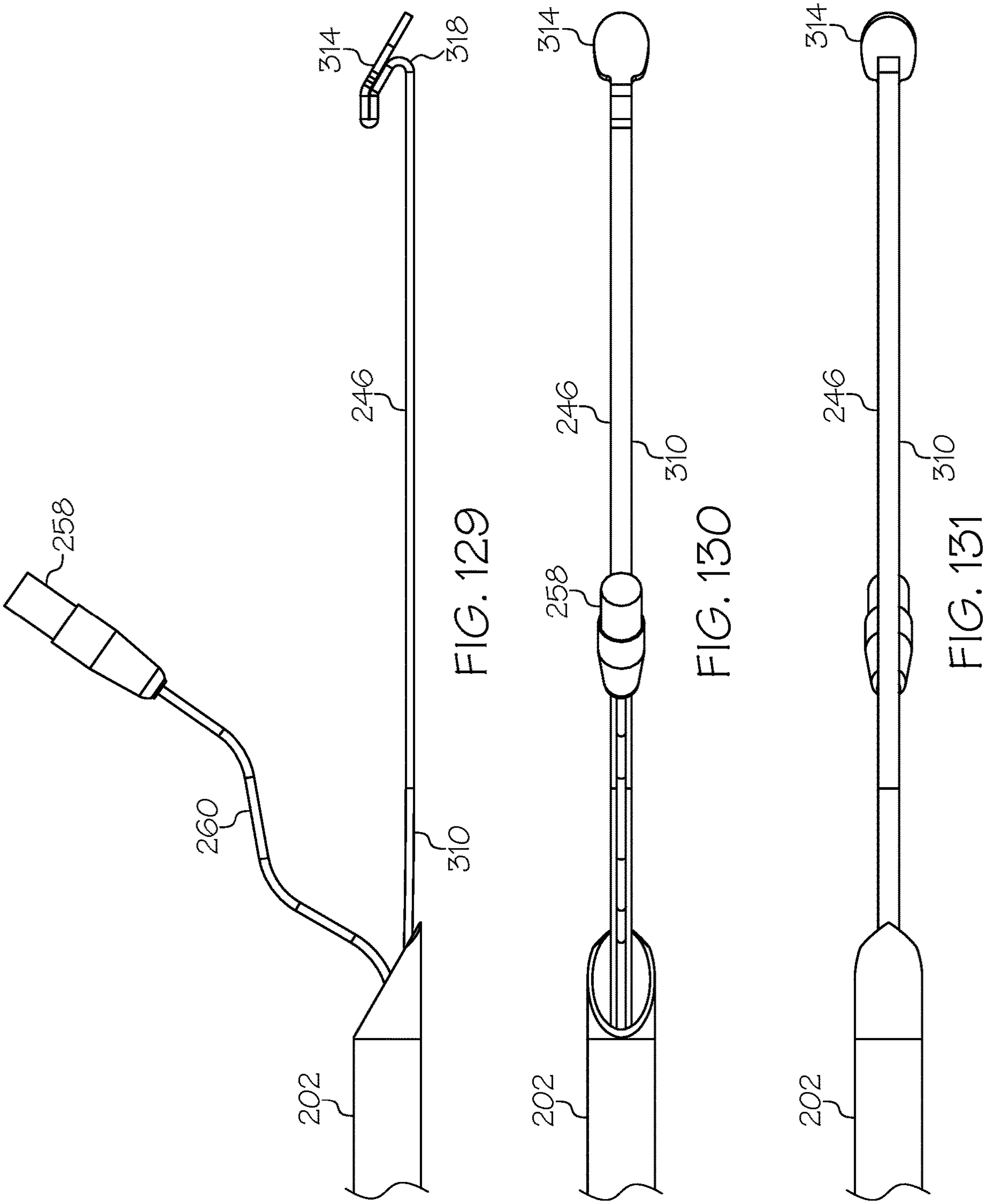

FIG. 131 is a bottom view of the fourth alternative embodiment of the flat-wire grasper member having an angled distal terminus including a hook and the suture retrieval needle, the grasper magnet, and the magnet wire of FIG. 128.

Figure 1:
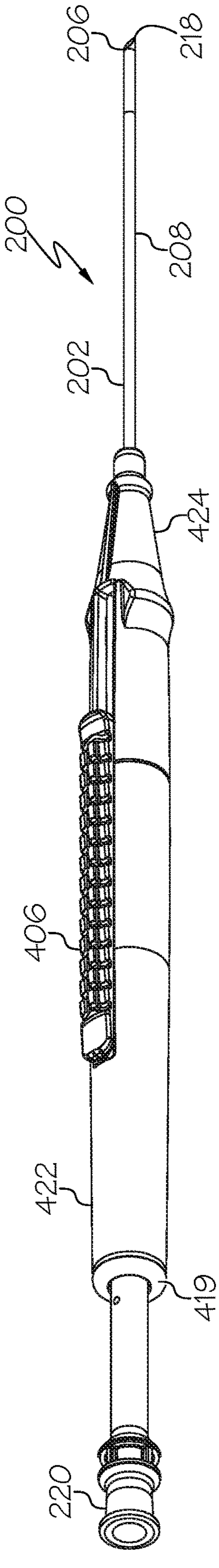
FIG. 1 is a perspective view of a magnet-assisted suture grasper comprising a suture retrieval needle, a retriever tube, a grasper ferrule, a grasper member, a grasper magnet, and a magnet wire, as disclosed herein, in which an advancer assembly of the device is in an unlocked fully retracted position, and the grasper magnet is sequestered within the suture retrieval needle as discussed herein.
Figure 2:
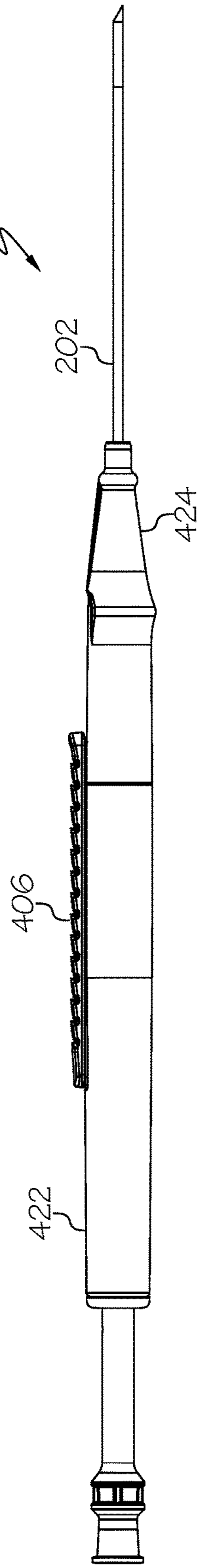
FIG. 2 is a side view of the magnet-assisted suture grasper of FIG. 1.
Figure 3:
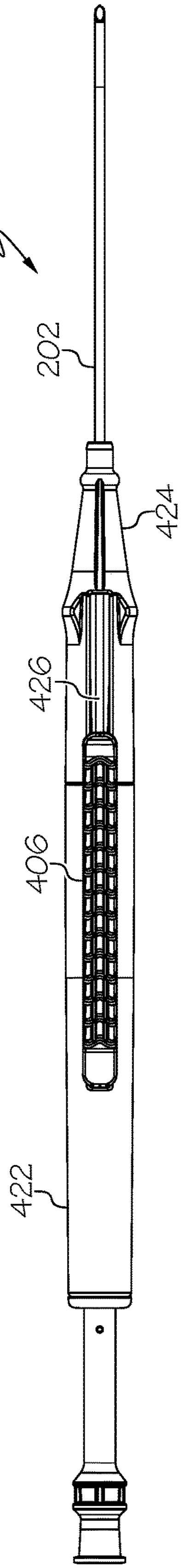
FIG. 3 is a top view of the magnet-assisted suture grasper of FIG. 1.
Figure 4:
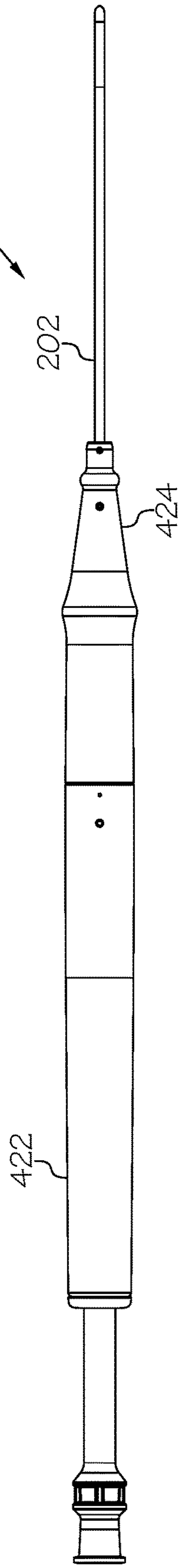
FIG. 4 is a bottom view of the magnet-assisted suture grasper of FIG. 1.
Figure 6:
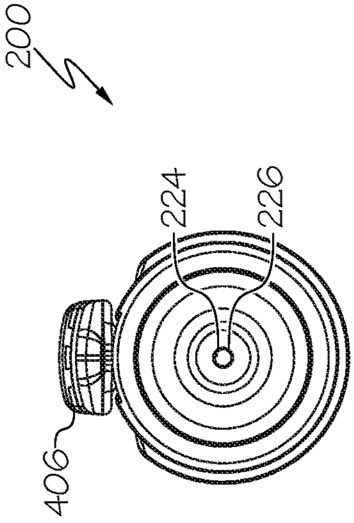
FIG. 6 is a back view of the magnet-assisted suture grasper of FIG. 1.
Figure 5:
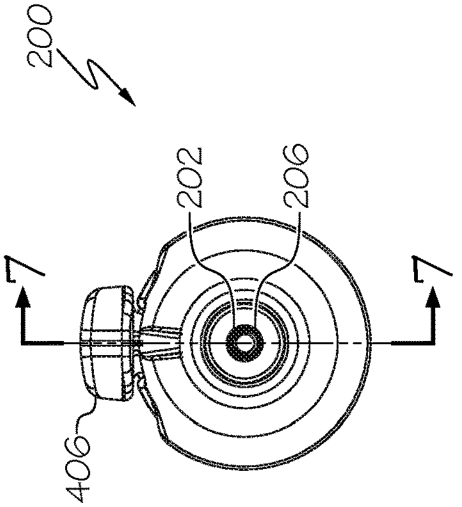
FIG. 5 is a front view of the magnet-assisted suture grasper of FIG. 1.
Figure 7:
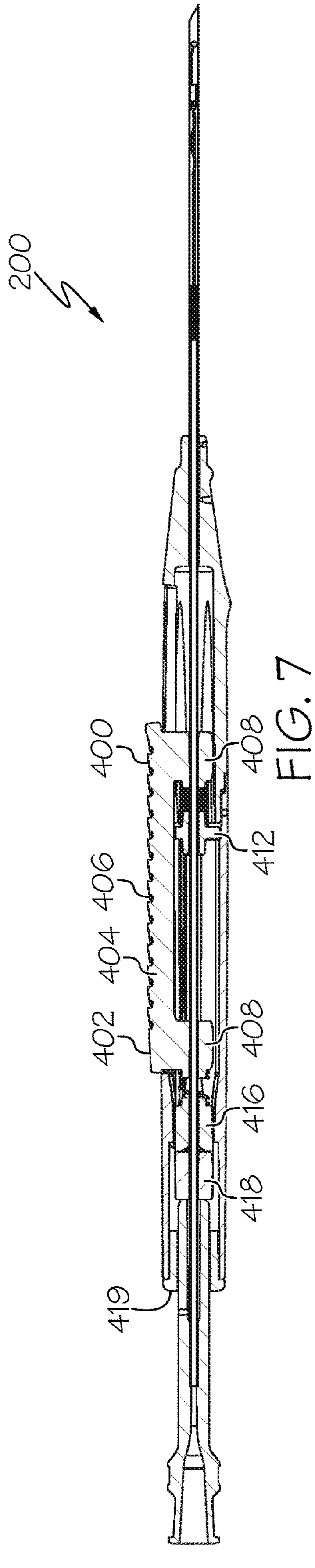
FIG. 7 is a side sectional view of the magnet-assisted suture grasper of FIG. 1, viewed along the cutting plane shown in FIG. 5.
Figure 132:
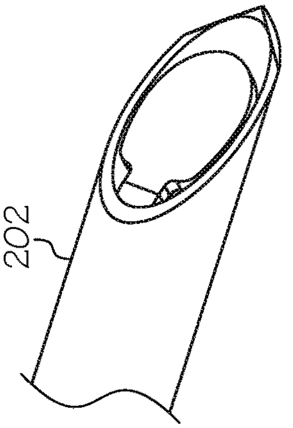

FIG. 132 is a perspective view of the fourth alternative embodiment of the flat-wire grasper member having an angled distal terminus including a hook and the suture retrieval needle, the grasper magnet, and the magnet wire of the magnet-assisted suture grasper of FIG. 1. The flat-wire grasper member is in the first position.

Figure 133:
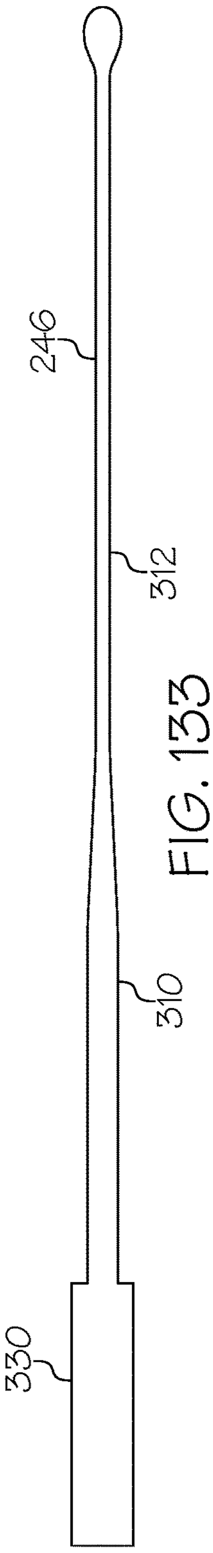

FIG. 133 is a top view of a first alternative embodiment of the grasper ferrule and the grasper member of the magnet-assisted suture grasper of FIG. 1, in which the grasper member comprises a grasper arm and the grasper arm is integral to the grasper ferrule. As shown, the distal terminus of the grasper arm is flat.

Figure 134:
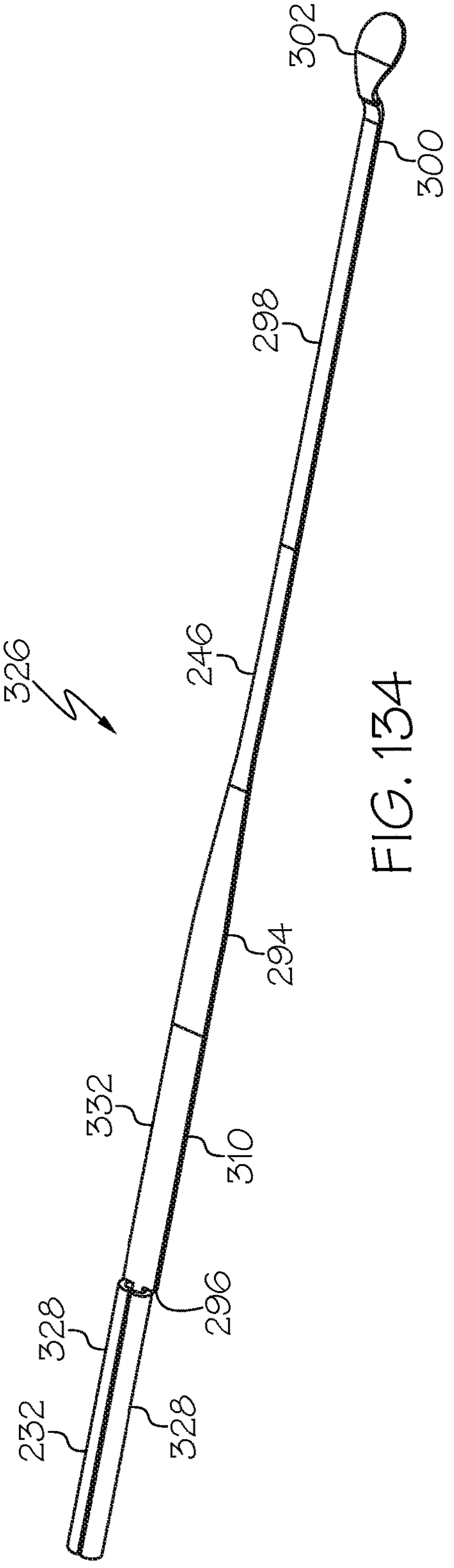

FIG. 134 is a perspective view of the first alternative embodiment of the grasper ferrule and the grasper member of FIG. 133. As shown, the distal terminus of the grasper arm is angled.

Figure 135:
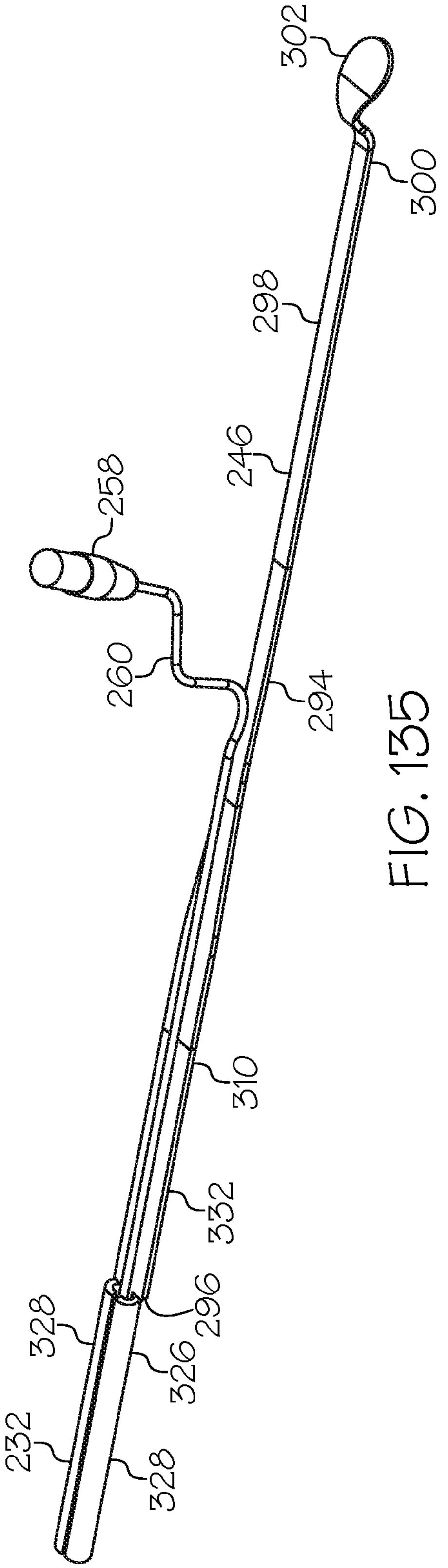

FIG. 135 is a perspective view of the first alternative embodiment of the grasper ferrule and the grasper member of FIG. 133 and the grasper magnet and the magnet wire of the magnet-assisted suture grasper of FIG. 1. As shown, the distal terminus of the grasper arm is angled.

Figure 136:
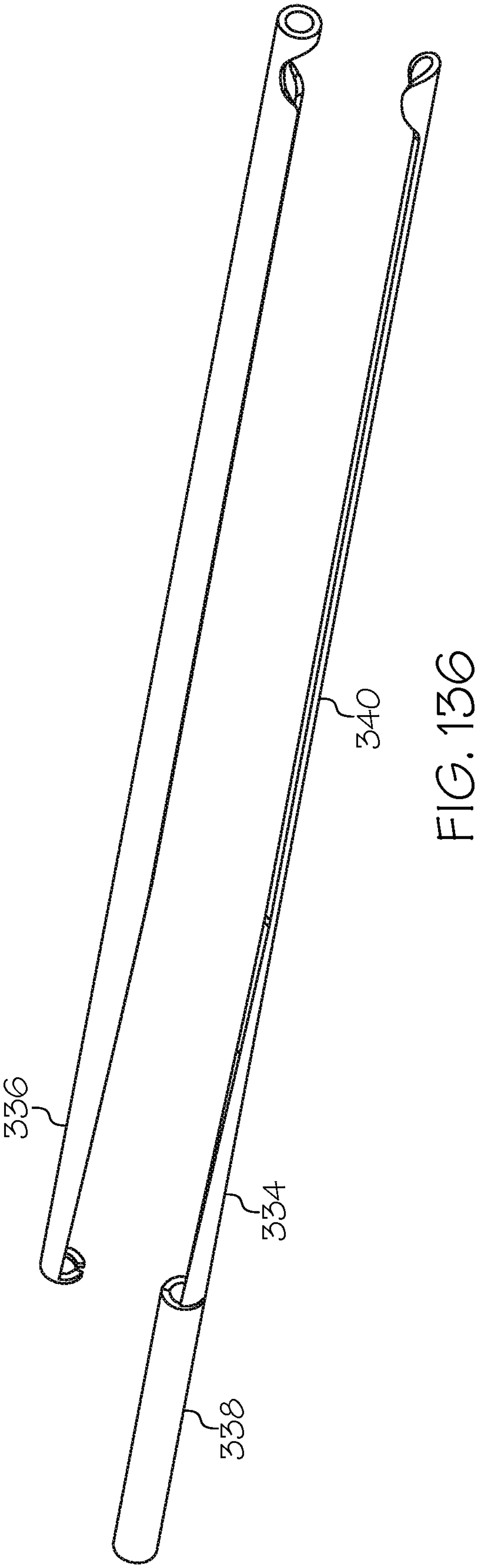

FIG. 136 is a perspective view of a second alternative embodiment of the grasper ferrule and the grasper member of the magnet-assisted suture grasper of FIG. 1, in which the grasper member comprises a grasper arm and the grasper ferrule and the grasper arm are formed from a cut tube. As shown, the distal terminus of the grasper arm has a semi-cylindrical shape.

Figure 137:
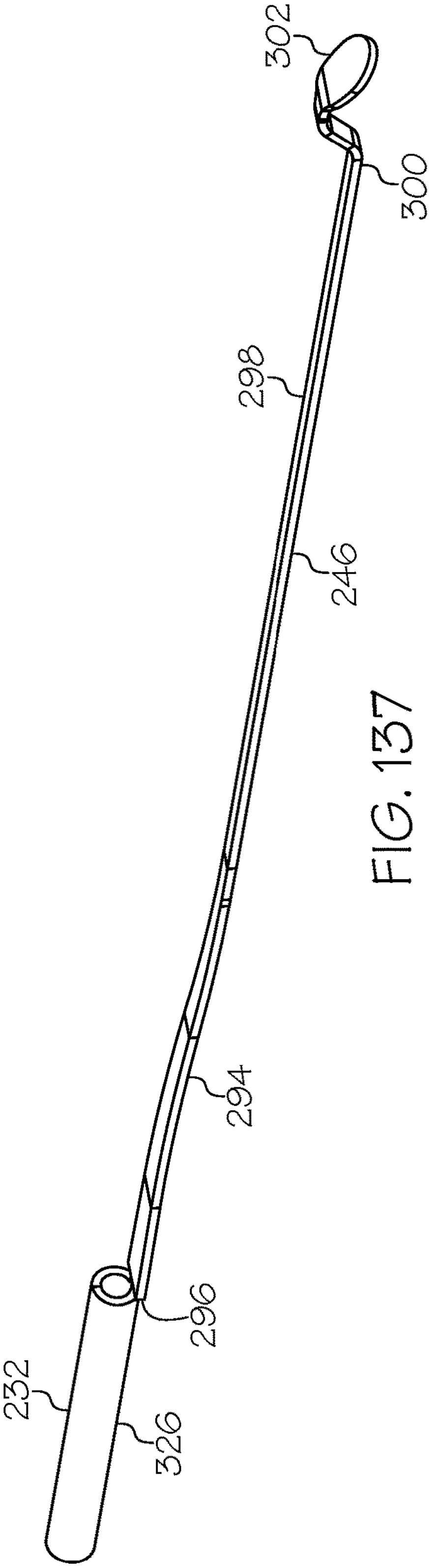

FIG. 137 is a perspective view of the second alternative embodiment of the grasper ferrule and the grasper member of FIG. 136. As shown, the distal terminus of the grasper arm is angled.

Figure 138:
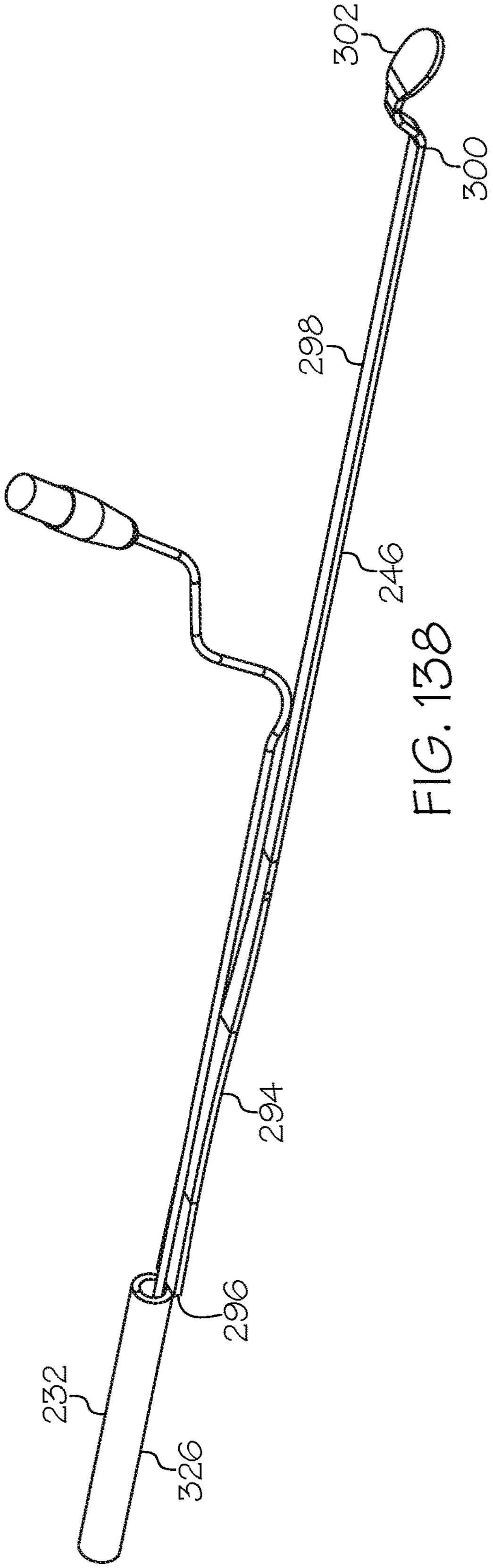

FIG. 138 is a perspective view of the second alternative embodiment of the grasper ferrule and the grasper member of FIG. 136 and the grasper magnet and the magnet wire of the magnet-assisted suture grasper of FIG. 1. As shown, the distal terminus of the grasper arm is angled.

Figure 139:
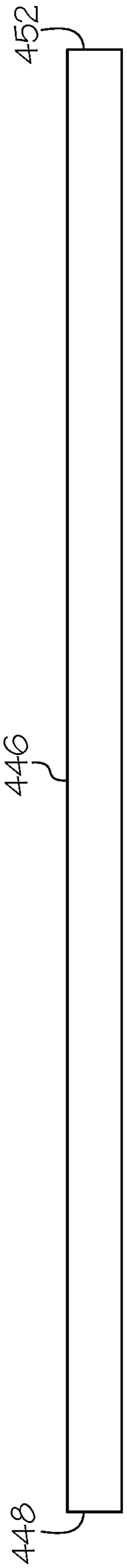

FIG. 139 is a side view of stabilizer tube that can be used in a magnet-assisted suture grasper.

Figure 140:
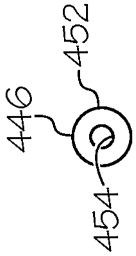

FIG. 140 is a front view of the stabilizer tube of FIG. 139.

Figure 141:
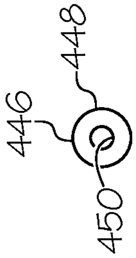

FIG. 141 is a back view of the stabilizer tube of FIG. 139.

Figure 142:
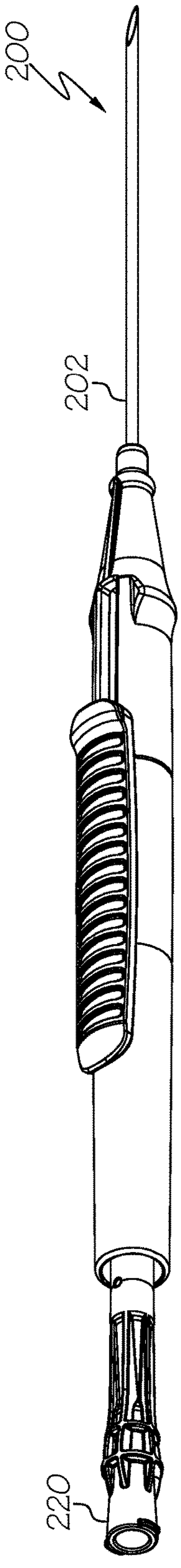

FIG. 142 is a perspective view of an alternative embodiment of a magnet-assisted suture grasper including a stabilizer tube.

Figure 143:
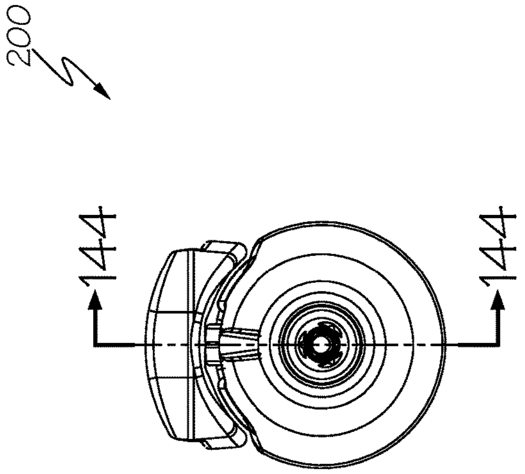

FIG. 143 is a front view of the alternative embodiment of a magnet-assisted suture grasper of FIG. 142.

Figure 144:
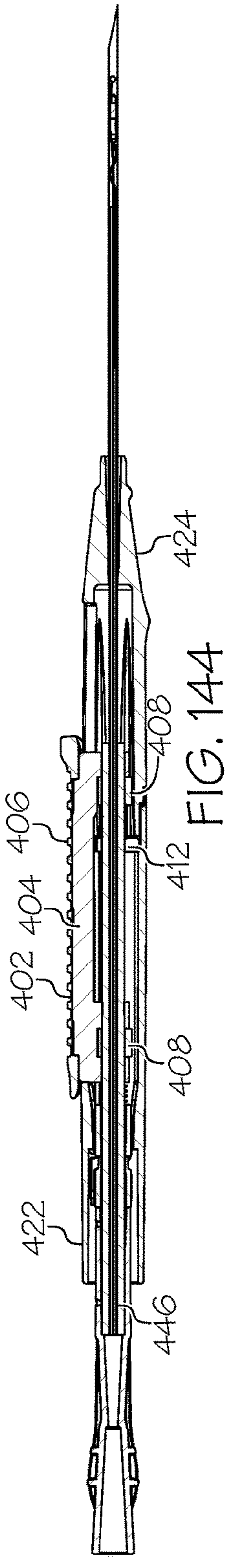

FIG. 144 is an expanded side sectional view of the alternative embodiment of a magnet-assisted suture grasper of FIG. 142, viewed along the cutting plane shown in FIG. 143.

DETAILED DESCRIPTION

Our magnet-assisted suture grasper comprising a suture retrieval needle, a retriever tube, a grasper ferrule, a grasper member, a grasper magnet, and a magnet wire as disclosed herein addresses the technical difficulty associated with capturing and retrieving sutures under indirect non-stereoscopic visualization, while also providing improved fluid flow characteristics relative to a preferred embodiment of our magnet-assisted suture grasper comprising a suture retrieval needle, a retriever body, a grasper wire, a grasper arm, and a grasper magnet as described by us in Applied Medical Technology, Inc.'s international application PCT/US2022/029627, filed May 17, 2022.

Like our magnet-assisted suture grasper described in PCT/US2022/029627, our magnet-assisted suture grasper disclosed herein involves use of two dipole magnets, a grasper magnet of a magnet-assisted suture grasper and a suture magnet of a magnetic suture, to assist with the initial positioning and holding of a magnetic suture while the magnetic suture is captured by a secondary mechanical means of the magnet-assisted suture grasper. The use of the two dipole magnets allows for a self-aligning feature, whereby the attractive forces of the northern and southern poles of the grasper magnet and the suture magnet cause the two magnets to align in a predictable manner, improving aspects of repeatability and reliability of function. Our magnet-assisted suture grasper disclosed herein greatly reduces the need to precisely position a suture passer, as the two magnetic aspects need only be brought near enough to one another that the magnetic fields can interact. The magnetic aspect of the suture is pulled into contact with the grasper magnet. This occurs without need for precise positioning to make contact. The secondary mechanical means then provides a steady-state connection between the magnetic suture and the magnet-assisted suture grasper that serves to hold the suture to the magnet-assisted suture grasper, allowing retrieval of the suture through soft tissue of a patient without needing to rely on magnetic attraction between the grasper magnet and the suture magnetic during the retrieval.

Our magnet-assisted suture grasper disclosed herein also provides improved fluid flow characteristics relative to a preferred embodiment of our magnet-assisted suture grasper described in PCT/US2022/029627 based on including a grasper ferrule that is fixedly disposed within the retriever tube, from which the grasper member and magnet wire extend distally.

In PCT/US2022/029627, we describe a preferred embodiment of a magnet-assisted suture grasper comprising a retriever body that comprises a retriever tube with a proximal hole, a distal hole, and a retriever lumen extending therebetween. We describe that the proximal hole of the retriever tube can be in fluid communication with a distal hole of a suture retrieval needle, and that the retriever tube is preferably made from a polymer such as nylon to facilitate making the retriever body including the retriever tube lumen.

By having the proximal hole of the retriever tube be in fluid communication with a distal hole of a suture retrieval needle, the magnet-assisted suture grasper can be used for recovery of liquids and/or gasses from a surgical site of a patient and/or delivery of contrast agents to the surgical site through the retriever tube lumen of the retriever body. Providing the ability to exchange fluids through the retriever tube lumen and thus through the magnet-assisted suture grasper allows for use of the magnet-assisted suture grasper with interventional techniques that employ fluid exchange to confirm the intracorporeal position of the distal end of the suture retrieval needle. For example, a need exists within the field of interventional radiology for the ability to confirm the location of cannulas inside the gastric lumens of patients during gastropexy. With the magnet-assisted suture grasper including a retriever tube lumen, following introduction of the suture retrieval needle into a patient, aspiration of a small amount of stomach juice or air can be used to confirm the intraluminal position of the distal end of the suture retrieval needle. Alternatively, a small amount of liquid radiographic contrast agent can be injected through the retriever tube lumen into the gastric lumen of the patient, allowing the intraluminal position to be confirmed through radiographic imaging.

By making the retriever tube from a polymer such as nylon, two additional lumens can be included in the retriever tube, one for insertion of a grasper wire and another for insertion of a magnet wire.

Here we have determined that by modifying the magnet-assisted suture grasper to include a grasper ferrule that is fixedly disposed within the retriever tube, from which the grasper member and magnet wire extend distally, a substantial increase in the effective cross-sectional area of the retriever tube lumen can be achieved along most of length of the retriever tube without having to increase the outer diameter of the retriever tube, while also allowing for the proximal hole of the retriever tube to remain in fluid communication with the distal hole of the suture retrieval needle. This can be accomplished without any need to include additional lumens in the retriever tube for insertion of a grasper wire or a magnet wire. Thus we can replace the multi-lumen retriever tube with a single-lumen retriever tube. We use a crimp joint to attach the grasper member and the magnet wire to the retriever tube in place of adhesive bonds that were used with the multi-lumen retriever tube. A crimp grasper ferrule is added to help keep the reduction factor (depth of crimp) within a desired range for the retriever tube. By manipulating the outer-diameter and inner-diameter dimensions of the grasper ferrule, we are able to adjust the amount of squeeze achieved by a crimp joint between the retriever tube and the grasper ferrule. This allows tuning of the crimp joint to achieve a balance of strength and toughness, without overstretching or overdrawing any one component. This is important because overstretching or overdrawing can lead to tearing and/or cracking of material, which can lead to a decrease in strength and consistency of the final joint. The magnet-assisted suture grasper so modified can include a retriever tube having a simpler structure, e.g., a cannula with a single lumen, made from a broader range of materials, e.g., a hard metal such as stainless steel, while remaining useful for recovery of liquids and/or gasses and delivery of contrast agents.

For example, we have compared the effective cross-sectional areas of the open lumen portions of a first exemplary retriever tube lumen of our magnet-assisted suture grasper as disclosed herein (hereinafter "new design") and a retriever tube lumen of our magnet-assisted suture grasper as described in PCT/US2022/029627 (hereinafter "previous design"), for which the corresponding retriever tubes had identical outer diameters. For this first example of our new design, we joined proximal portions of a grasper member comprising a grasper arm loop and a proximal portion of a magnet wire to a grasper ferrule by inserting the proximal portions into a ferrule lumen of the grasper ferrule and crimping the grasper ferrule onto these proximal portions to form an inner crimp joint. We then joined the grasper ferrule, the grasper member, and the magnet wire to the retriever tube by inserting the grasper ferrule and attached proximal portions into a retriever tube lumen of the retriever tube and crimping the retriever tube onto the grasper ferrule and proximal portions to form an outer crimp joint. For our new design, the open lumen portion of the retriever tube lumen is the portion of the retriever tube lumen not occupied by the grasper ferrule. For our previous design, the open lumen portion is the lumen that extends from the proximal end to the distal end of a retriever tube that also includes the two additional lumens for insertion of a grasper wire and a magnet wire. Thus, in our comparison the cross-sectional area of the open lumen portion for our new design is greater than the cross-sectional area of the open lumen portion for our previous design. Specifically, the cross-sectional area of the open lumen portion of our new design is 0.00091 square inches (0.59 square mm), whereas the cross-sectional area of the open lumen portion of our previous design is 0.00013 square inches (0.084 square mm). Our new design thus has 6.8 fold greater effective cross-sectional area compared to our previous design, which is a 584% improvement. In this comparison the length of the retriever tube in our new design is 6.25 inches (159 mm) and the length of the grasper ferrule is 0.250 inches (6.35 mm). The retriever tube lumen in our new design thus is unrestricted over 96% of length of the retriever tube.

Moreover, in empirical testing, for the new design it took 16.2 seconds to push 5 mL of water through the retriever tube lumen, whereas for the previous design, it took 48 seconds to push 5 mL of water through the retriever tube lumen. The new design therefore flows 2.96 fold faster than the previous design. This is a 196% improvement.

In addition, using Poiseuille's law to calculate the pressure loss across the retriever tubes of assembled magnetic-assisted suture graspers of our new design and our previous design, based on the empirical test data noted above, we find that the pressure drop across the retriever tube of our new design is 3,694 Pa (0.54 psi), whereas the pressure drop across the retriever tube of our previous design is 66,528 Pa (9.65 psi). This is a 94.4% reduction in pressure drop.

Also for example we have compared water flow rates for a second example of our new design, this time including a grasper member including a single integral grasper wire and grasper arm and made using an outer crimp joint without an inner crimp joint, with the first example our new design described above. For the second example, we inserted a proximal portion of a grasper member including a single integral grasper wire and grasper arm, a proximal portion of a magnet wire, and a grasper ferrule into a retriever tube lumen of a retriever tube, without making an inner crimp joint and with the proximal portions positioned adjacent outside of the grasper ferrule rather than having been inserted in the ferrule lumen of the grasper ferrule. We then crimped the retriever tube onto the grasper ferrule and the proximal portions to form an outer crimp joint. We determined that the flow rate of the second example was 7.2 fold greater than that of the first example, specifically 0.064 ml/sec (at 1.0 psi pressure) compared to 0.46 ml/sec (at 1.0 psi pressure). Apparently, the second example advantageously maintains a relatively larger open cross-sectional area within the outer crimp joint than the first example.

The magnet-assisted suture grasper so modified to include a retriever tube having only one lumen and being made from a hard metal such as stainless steel provides additional advantages of greater structural integrity, more consistent operative feel, broader chemical compatibility, and greater ease of manufacture.

Regarding greater structural integrity, a retriever tube made from a hard metal such as stainless steel is stiffer than a retriever tube made from a polymer such as nylon by about two orders of magnitude. The tensile modulus of 304 stainless steel is approximately 190 GPA, compared to approximately 1-3 GPA for extrusion grade transparent polymers. The greater stiffness of the metal retriever tube means that it is more resistant to buckling, and does not require the added support of a stabilizer tube, which we describe in PCT/US2022/029627 for our previous design. Additionally, metal tubes are commodity products, available in standard gauge sizes, whereas polymer tubes are engineered products. Replacing two engineered products, i.e., a polymer retriever tube and a polymer stabilizer tube, with a commodity product, i.e., a metal retriever tube, provides advantage of decreased costs and increased supply chain flexibility.

Regarding more consistent operative feel, the greater strength and stiffness of a metal retriever tube allows use of a tube made with a thinner wall than for a corresponding polymer retriever tube. This allows for simultaneously increasing the inner diameter and decreasing the outer diameter of the metal retriever tube. The decrease in outer diameter increases the sliding clearance between components within the lumen of the retriever tube. Additionally, metal tubes generally exhibit better straightness and roundness over polymer tubes. The extra sliding clearance and greater consistency in straightness and roundness results in a noticeable reduction in rubbing of the metal retriever tube with mating components, which provides a smoother and more consistent feel during operation.

Regarding broader chemical compatibility, the metal components used in the new design are generally less reactive with the typical chemical agents to which the components may be exposed during surgery, for example radiographic contrast agents, saline, sterile water, anesthetics, etc.

Regarding greater ease of manufacture, the crimp joints used in assembly of our new design do not require as much skill to assemble, and require significantly less time to assemble and complete, in comparison to our previous design. Moreover, the multi-lumen polymer retriever tube used in our previous design was a custom engineered component that required a high skill level to produce, due to the scale of the component and the tightness of tolerances required to work within the assembly. In contrast, metal cannulas are a commodity part, available in standard gauge sizes of hypodermic needles, that can be easily sourced from numerous suppliers and/or manufacturers.

Like our magnet-assisted suture grasper described in PCT/US2022/029627, optionally our magnet-assisted suture grasper disclosed herein can further comprise a lock mechanism that can be reversibly engaged to prevent translation of the retriever body within the needle lumen.

Our magnet-assisted suture grasper that optionally includes the lock mechanism can incorporate an incompressible and reversible mechanical lock that, when engaged, fixes the longitudinal position of the grasper member in at least one direction, and thereby also fixes the position of a magnetic suture being grasped by the grasper member in the same direction. When engaged, the mechanical lock advantageously bears fully any tensile load applied to the magnetic suture in the same direction. The mechanical lock provides for a single equipoised position. Moreover, a return spring may be added to the magnet-assisted suture grasper to advantageously provide a second equipoised position, allowing the magnet-assisted suture grasper to be switched between positions with a momentary energy input, but requiring no additional energy input to maintain either position.

For comparison, conventional suture passers make use of a spring located between a moveable plunger element and a fixed body element. According to designs of the conventional suture passers, depressing the plunger element by the application of external force compresses the spring, causing the suture passer to transition from a closed position to an open position. Upon release of the plunger element, and thus in the absence of external force, the spring exerts a counterforce back upon the plunger, which returns the suture passer from the open position to the closed position. The conventional suture passers lack a mechanical lock, and thus rely solely on the spring to resist tensile loading of the suture in the direction which acts to pull the suture out of the suture passer. The spring thus needs to be stiff enough that the force required to compress the spring to a position where the suture passer opens sufficiently far to release the suture is greater than the expected loads that will be placed on the suture during retrieval. Additionally, since the conventional suture passers provide for only one equipoised position, which is the closed position, the operator must continually apply an external force great enough to compress the spring in order to maintain an open position of the suture passer while retrieving a suture.

With our magnet-assisted suture grasper including the lock mechanism, these loads are born by the mechanical lock rather than a spring. As a result, a lighter spring can be used, which reduces the operational force needed to move our magnet-assisted suture grasper between open and closed positions. This allows our magnet-assisted suture grasper to be slidingly operated with a single finger, which allows for a more precise gripping style better suited to delicate procedures, such as, for example, dissection and mobilization of the spermatic cord structures away from the peritoneum, such as in percutaneous inguinal ring suturing. Moreover, because the mechanical lock provides an equipoised closed position, the spring action can be reversed to also create an equipoised open position. This advantageously allows an operator to manipulate our magnet-assisted suture grasper in an open position without having to hold forcefully against a spring.

To quantify the significance of this change, consider the design of a suture passer needed to retrieve a 3-0 polyester suture. The minimum tensile strength of a non-absorbable class I suture of 3-0 size, as required by USP <881> is 0.96 kgf (approximately 9.4 N), while the typical tensile strength of a 3-0 polyester braided suture has been observed to be around 1.5-2.0 kgf (approximately 15 to 20 N). In designing our magnet-assisted suture grasper, we realized that it would be desirable to make our magnet-assisted suture grasper such that it could retain sutures up to the full tensile capacity of the sutures.

Using a conventional suture passer, for which the return spring must retain a suture against tensile loading, the spring must be sufficiently stiff to resist compression to a point where the suture passer opens enough to release the suture at up to 2.0 kgf (approximately 20 N). This in turn means that an input force of >2.0 kgf (greater than approximately 20 N) will be required to compress the spring to the open position. Additionally, the operator must apply this >2.0 kgf (greater than approximately 20 N) force continually to maintain the open position.

In our design, the spring only needs to overcome the frictional drag between sliding components. We have found that an input force of 0.045 kgf (approximately 0.44 N) provides sufficient force with an adequate safety factor to assure that our magnet-assisted suture grasper is always returned to the fully open position by the spring. This is the minimum force required by the spring at the lower bound of travel. The maximum force that the spring generates occurs at the upper bound of travel. Working within the geometric constraints of our current design, we may select a typical open-ended music wire spring having an outer diameter of 0.195 inches (4.95 mm) and a wire diameter of 0.008 inches (0.2 mm) and a free length of 3.500 inches (88.90 mm), with 21 coils disposed between ends. We find this spring has a calculated spring rate of 0.195 kgf (1.91 N), resulting in a preload of 0.046 kgf (0.45 N) at the minimal extent of travel, meeting our 0.045 kgf (0.44 N) requirement, and a calculated peak load of 0.063 kgf (0.618 N) at the maximal extent of travel.

Compared to the conventional suture passer, our magnet-assisted suture grasper including the lock mechanism advantageously results in a 96.8% decrease in the force needed to move the device between open and closed positions. Additionally, since our magnet-assisted suture grasper including the lock mechanism provides for equipoised closed and open positions, this force is only needed momentarily to change positions, and does not need to be continually applied while maneuvering our magnet-assisted suture grasper including the lock mechanism.

An example embodiment of a magnet-assisted suture grasper 200 for grasping a magnetic suture 500 is illustrated in FIGS. 1-17. As shown in FIGS. 1-8, a grasper member 246 of the magnet-assisted suture grasper 200 is positioned within a needle lumen 216 of the magnet-assisted suture grasper 200, and a grasper magnet 258 of the magnet-assisted suture grasper 200 is sequestered within the needle lumen 216. As shown in FIGS. 9-17, the grasper member is positioned outside of the needle lumen 216, and the grasper magnet 258 is exposed from the needle lumen 216, allowing contact between the grasper magnet 258 and a magnetic suture 500 attracted thereto.

With reference to FIGS. 84-87, the magnetic suture 500 to be grasped can comprise a suture magnet 502 and a suture 504 extending from the suture magnet 502. The magnetic suture 500 can be, for example, a magnetic suture as described in U.S. Pub. No. 2021/0059667, which is incorporated herein by reference. Thus, the magnetic suture 500 can further comprise a magnetic-suture ferrule 506 with a tapered region 508 in which the suture 504 is provided knotted and secured with an adhesive and a straight region 510 in which the suture magnet 502 is provided.

Figure 17:
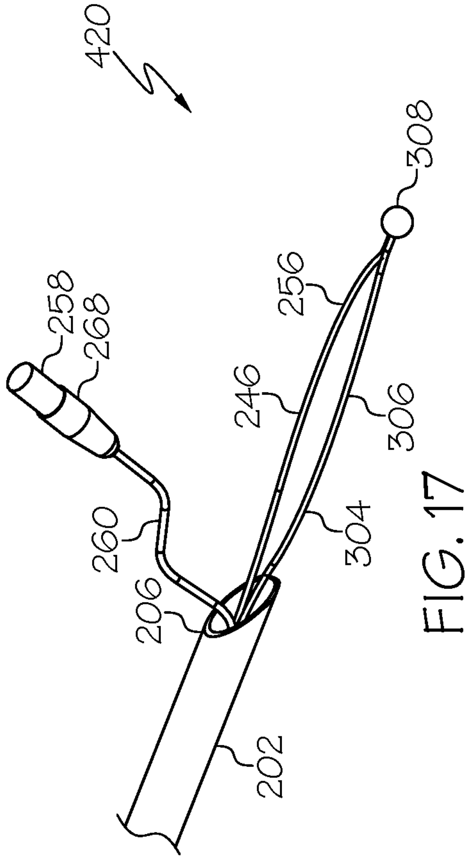
FIG. 17 is a perspective view of a distal portion of the magnet-assisted suture grasper of FIG. 9, in which the grasper member is in the second position.
Figure 18:
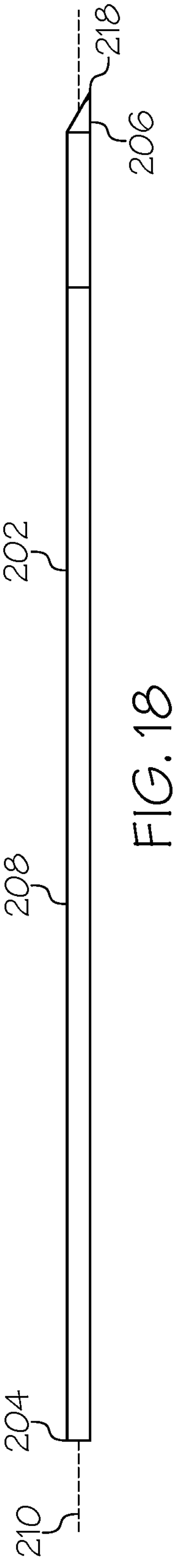
FIG. 18 is a side view of the suture retrieval needle of the magnet-assisted suture grasper of FIG. 1.
Figure 19:
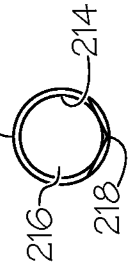
FIG. 19 is a front view of the suture retrieval needle of FIG. 18.
Figure 20:
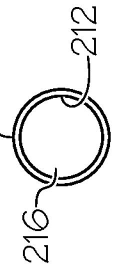
FIG. 20 is a back view of the suture retrieval needle of FIG. 18.

As shown in FIGS. 18-20, with reference to FIGS. 1-17, the magnet-assisted suture grasper 200 comprises a suture retrieval needle 202 comprising a proximal end 204, a distal end 206, and a needle body 208 extending therebetween. The needle body 208 defines a needle body axis 210 between the proximal and distal ends 204, 206 of the suture retrieval needle. The needle body 208 has a proximal hole 212, a distal hole 214, and a needle lumen 216 extending therebetween along the needle body axis 210.

The suture retrieval needle 202 can be, for example, a hypodermic needle. For example, the suture retrieval needle 202 can be an introducer needle designed for introducing guide wires into a vessel, applied here as the suture retrieval needle 202. Also for example, the suture retrieval needle 202 can be a 24-gauge needle, a 21-gauge needle, an 18-gauge needle, a 17-gauge needle, a 16-gauge needle, or a 14 gauge needle.

As shown in FIGS. 1-17, in some embodiments, the suture retrieval needle 202 is straight. In accordance with these embodiments, the needle body axis 210 thereby is straight. Alternatively, as shown in FIGS. 88-93, in some embodiments, the suture retrieval needle 202 is curved. In accordance with these embodiments, the needle body axis 210 thereby is curved. In some embodiments, one or more portions of the suture retrieval needle 202 can be straight, and one or more portions can be curved. For example, as shown in FIGS. 88-93, in some embodiments, the suture retrieval needle 202 includes a curve at or near its distal end 206 but otherwise is straight. In accordance with these embodiments, the needle body axis 210 also includes a curve at or near the distal end 206 of the suture retrieval needle 202, but otherwise is straight.

As shown in FIG. 18, with reference to FIGS. 1-17, in some embodiments, the suture retrieval needle 202 has a sharp tip 218. This can be advantageous for piercing tissue during insertion of the suture retrieval needle 202 into a patient.

Figure 21:
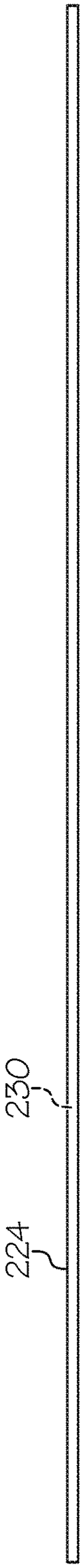
FIG. 21 is a side view of the retriever tube of the magnet-assisted suture grasper of FIG. 1.
Figure 22:
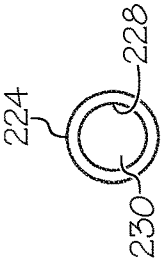
FIG. 22 is a front view of the retriever tube of FIG. 21.
Figure 23:
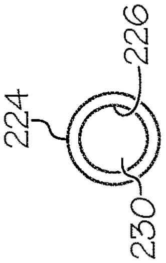
FIG. 23 is a back view of the retriever tube of FIG. 21.

As shown in FIGS. 21-23, with reference to FIGS. 1-17, the magnet-assisted suture grasper 200 also comprises a retriever tube 224. The retriever tube 224 is partially disposed within the needle lumen 216 and translatable therein along the needle body axis 210. The retriever tube 224 can be made from a hard metal, such as stainless steel.

The retriever tube 224 has a proximal hole 226, a distal hole 228, and a retriever tube lumen 230 extending therebetween. The proximal hole 226 of the retriever tube 224 is in fluid communication with the distal hole 214 of the needle body 208 through the retriever tube lumen 230 and the needle lumen 216. As noted above, this can be advantageous by allowing recovery of liquids and/or gasses from a surgical site of a patient and/or delivery of contrast agents to the surgical site through the retriever tube lumen 230 of the retriever tube 224. In some embodiments, the retriever tube lumen 230 is the only lumen of the retriever tube 224. As noted above, the magnet-assisted suture grasper 200 comprising a retriever tube 224 having only one lumen and being made from a hard metal such as stainless steel provides advantages of greater structural integrity, more consistent operative feel, broader chemical compatibility, and greater ease of manufacture.

Figure 26:
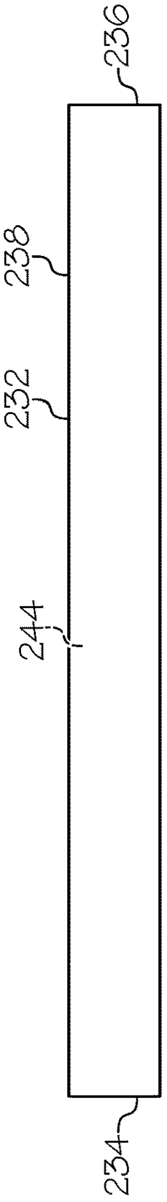
FIG. 26 is a side view of the grasper ferrule of the magnet-assisted suture grasper of FIG. 1.
Figure 28:
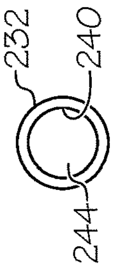
FIG. 28 is a back view of the grasper ferrule of FIG. 26.
Figure 27:
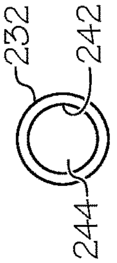
FIG. 27 is a front view of the grasper ferrule of FIG. 26.
Figure 29:
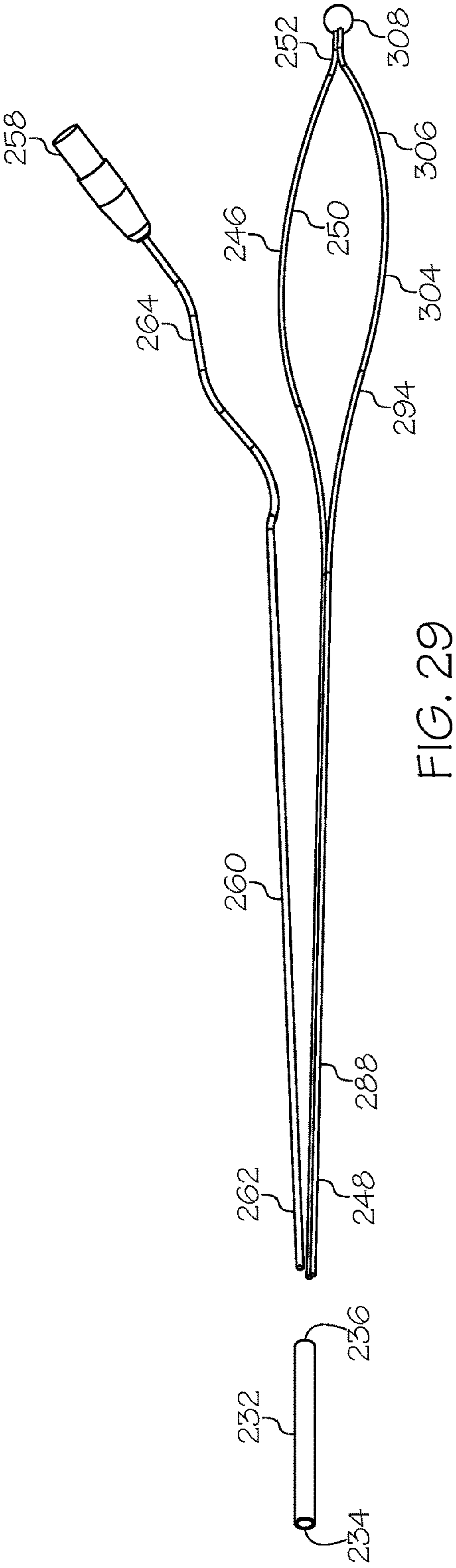
FIG. 29 is an exploded perspective view of the grasper ferrule, the grasper member, the grasper magnet, and the magnet wire of the magnet-assisted suture grasper of FIG. 1.
Figure 30:
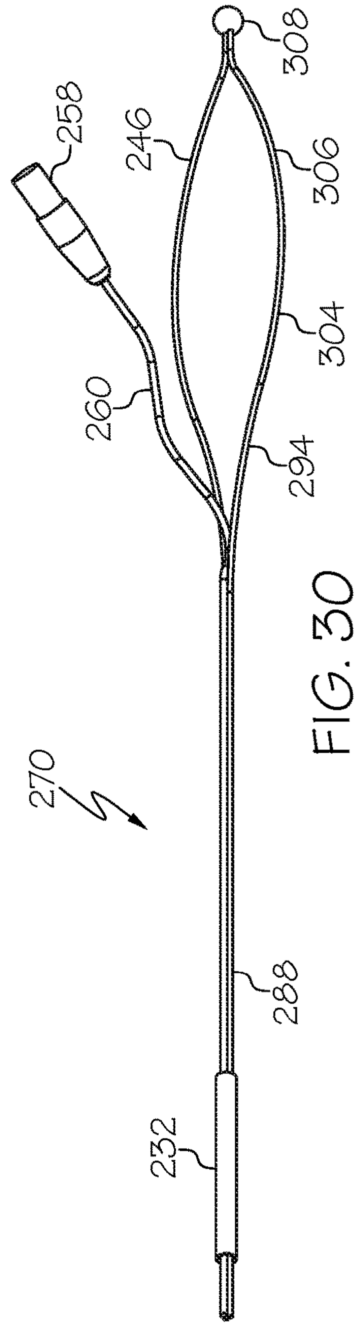
FIG. 30 is a perspective view of the grasper ferrule, the grasper member, the grasper magnet, and the magnet wire of the magnet-assisted suture grasper of FIG. 1.
Figure 31:
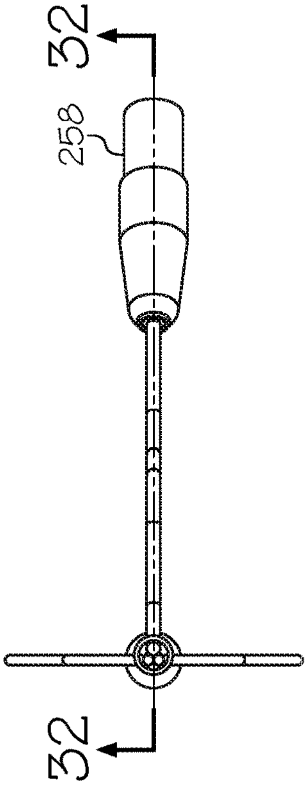
FIG. 31 is a back view of the grasper ferrule, the grasper member, the grasper magnet, and the magnet wire of FIG. 30.

As shown in FIGS. 26-28, with reference to FIGS. 29-40, the magnet-assisted suture grasper 200 also comprises a grasper ferrule 232 comprising a proximal end 234, a distal end 236, and a ferrule body 238 extending therebetween. The ferrule body 238 has a proximal hole 240, a distal hole 242, and a ferrule lumen 244 extending therebetween. The grasper ferrule 232 can be, for example, a metal crimp ferrule made from stainless steel or Nitinol, among other metals, or a hard plastic ferrule made from polycarbonate or polyether ether ketone, among other hard plastics.

The grasper ferrule 232 is fixedly disposed within the retriever tube 224, as discussed below. Accordingly, the grasper ferrule 232 has an outer diameter that is smaller than an inner diameter of the retriever tube 224.

Figure 24:
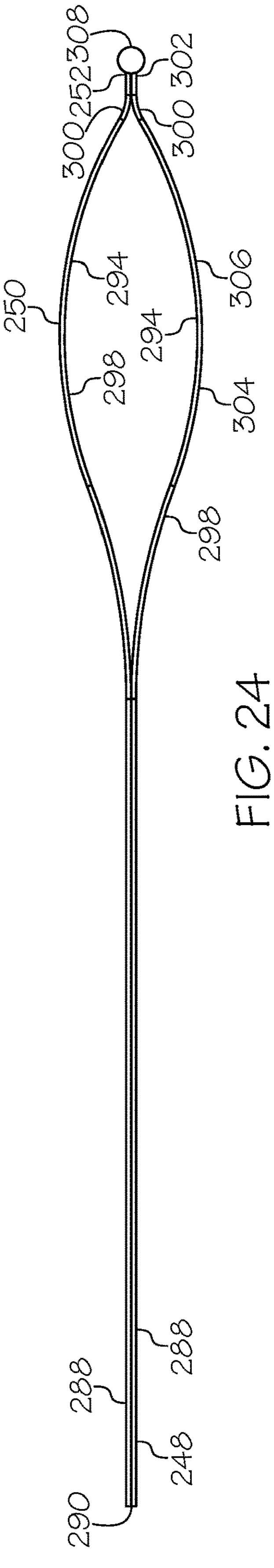
FIG. 24 is a top view of the grasper member of the magnet-assisted suture grasper of FIG. 1.
Figure 84:
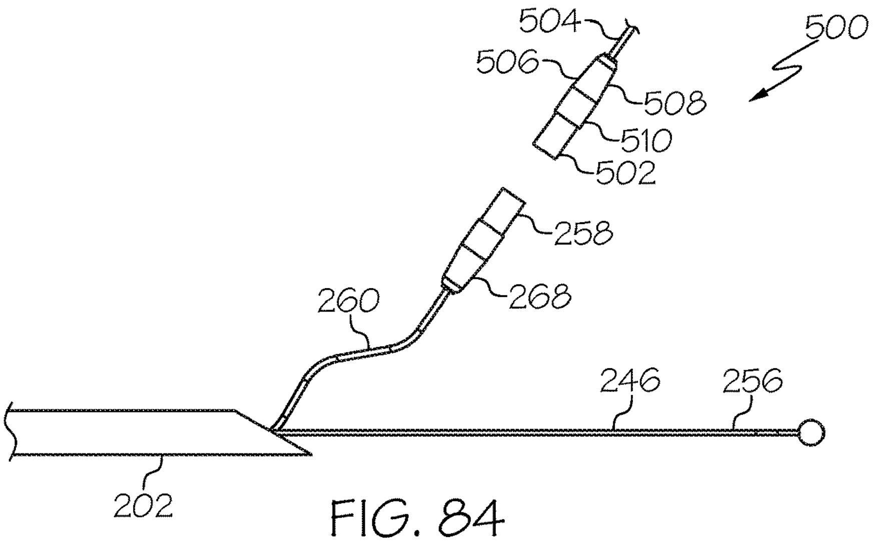
FIG. 84 is a side view of a distal portion of the magnet-assisted suture grasper of FIG. 1, in which the advancer assembly is in the locked extended position, the grasper member is in the second position, the grasper magnet is exposed, and the grasper magnet is attracting a magnetic suture.

As shown in FIG. 24 and FIG. 84, with reference to FIGS. 1-17, the magnet-assisted suture grasper 200 also comprises a grasper member 246. The grasper member 246 comprises a proximal portion 248, an intermediate portion 250, and a distal portion 252.

Figure 32:
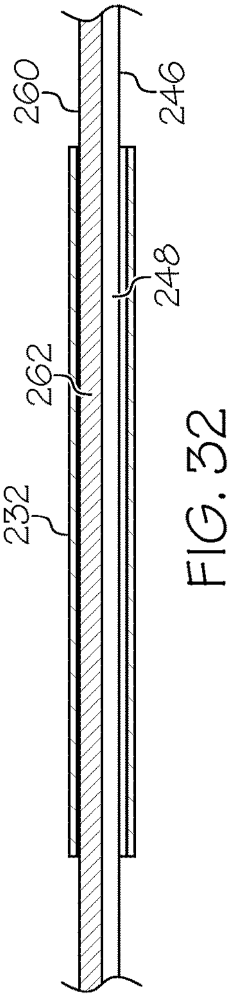
FIG. 32 is an expanded side sectional view of the grasper ferrule, the grasper member, and the magnet wire of FIG. 30, viewed along the cutting plane shown in FIG. 31.

The grasper member 246 extends distally from the grasper ferrule 232. As shown in FIG. 32, in some embodiments, the proximal portion 248 of the grasper member 246 is fixedly disposed within the grasper ferrule 232, as discussed below. In some embodiments, the proximal portion 248 of the grasper member 246 is disposed adjacent the grasper ferrule 232 and not within the ferrule lumen 244 of the grasper ferrule 232, as discussed below. As shown in FIG. 135 and FIG. 138, in some embodiments, the grasper member 246 is integral to the grasper ferrule 232, also as discussed below.

As shown by comparison of FIG. 8 and FIG. 16, the grasper member 246 is reversibly moveable with respect to the needle lumen 216 between a first position 254 and a second position 256, as discussed below.

The grasper member 246 can be made from, for example, a polymeric material, a metal with a high proportional limit, such as Nitinol, or a hard metal, such as stainless steel.

In some embodiments, the grasper member 246 is more flexible than the needle body 208. This can be advantageous for suture retrieval needles 202 in which one or more portions of the suture retrieval needle 202 are curved, e.g., a suture retrieval needle 202 that includes a curve at or near its distal end but otherwise is straight. Then the grasper member 246 is preferentially made of a polymeric material, or a metal with a high proportional limit, such as Nitinol, to allow the grasper member 246 to elastically deform around the curve of the suture retrieval needle 202.

Figure 25:
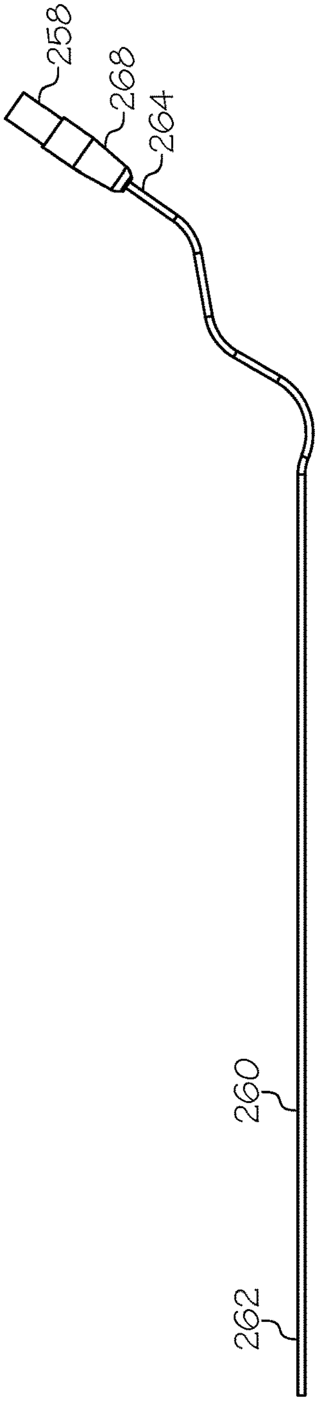
FIG. 25 is a side view of the grasper magnet and magnet wire of FIG. 1.

As shown in FIG. 25, with reference to FIGS. 1-17, the magnet-assisted suture grasper 200 also comprises a grasper magnet 258. The grasper magnet 258 is disposed adjacent the intermediate portion 250 of the grasper member 246. As shown by comparison of FIG. 8 and FIG. 16, the magnet-assisted suture grasper 200 sequesters the grasper magnet 258 within the needle lumen 216 when the grasper member 246 is in the first position 254 and exposes the grasper magnet 258 from the needle lumen 216 when the grasper member 246 is in the second position 256. The grasper magnet 258 can be, for example, a permanent dipole magnet.

As shown in FIG. 25, with reference to FIGS. 1-17, the magnet-assisted suture grasper 200 also comprises a magnet wire 260 having a proximal portion 262 and a distal portion 264.

The magnet wire 260 extends distally from the grasper ferrule. As shown in FIG. 32, in some embodiments, the proximal portion 262 of the magnet wire 260 is fixedly disposed within the grasper ferrule 232, as discussed below. In some embodiments, the proximal portion 262 of the magnet wire 260 is disposed adjacent the grasper ferrule 232 and not within the ferrule lumen 244 of the grasper ferrule 232, as discussed below.

The grasper magnet 258 is fixedly attached to the distal portion 264 of the magnet wire 260, either directly, e.g., based on adhesion or other direct attachment, or indirectly, e.g., based on attachment through one or more intermediate parts, such as a ferrule, ring, or sleeve, among other intermediate parts.

Translation of the retriever tube 224 also results in translation of the magnet wire 260, and thus also the grasper magnet 258.

As shown in FIG. 25, in some embodiments, the magnet wire 260 further comprises a magnet wire distal terminus 266, the magnet-assisted suture grasper 200 further comprises a magnet ferrule 268 fixedly attached to the magnet wire distal terminus 266, and the grasper magnet 258 is fixedly attached to the magnet ferrule 268.

The magnet wire 260 can be, for example, a metal wire, such as a Nitinol wire or a stainless steel wire, or a plastic wire, and can be formed, for example, as a solid wire, a stranded wire, or a braided wire, and can have a shape, for example, based on being a shaped wire and/or a stamped wire, and can comprise, for example, one or more wires joined together at one or more common points, for example, by welding, soldering, braiding, crimping, adhesive, or other means. The magnet wire 260 can be, for example, a Nitinol wire having a mean diameter of about 0.0080 inches (0.20 mm).

Considering attachment of the grasper magnet 258 to the magnet wire 260 in more detail, the grasper magnet 258 can be attached to the magnet wire 260, for example, similarly as described in U.S. Pub. No. 2021/0059667 for attachment of a magnet to a suture. This can be accomplished as follows. The grasper magnet 258 can be attached to a magnet ferrule 268, which is attached to a magnet wire 260 having an enlarged magnet wire distal terminus 266. With reference to U.S. Pub. No. 2021/0059667, the enlarged magnet wire distal terminus 266 would replace the knot tied in a suture. A ball end is the preferred shape for the magnet wire distal terminus 266 and a mono-filament with a round cross-section is the preferred shape of the magnet wire 260. However, as long as the magnet wire 260 and the magnet wire distal terminus 266 are sized appropriately, other constructions and final shapes would also be suitable. The magnet wire distal terminus 266 may be formed into any shape, e.g., cubic, cylindrical, pyramidal, organic, etc., and the magnet wire 260 may be of any cross sectional shape, e.g., square, rectangular, cruciform, etc., and may be of mono- or multi-filament construction.

The magnet wire 260 must be sized small enough to fit through the small opening of the magnet ferrule 268, while the magnet wire distal terminus 266 must be sized larger than the small opening of the magnet ferrule 268 and smaller than the large opening of the magnet ferrule 268. The magnet wire distal terminus 266 may be integrated into the magnet wire 260, e.g., the magnet wire distal terminus 266 can be melt formed, coined, bent, etc., or it may be a separate component. If a separate component, it may be attached by mechanical means, e.g., swaged, threaded, interference fit, pinned, etc., by adhesive means, or by other means, e.g., welding, soldering, brazing, etc.

To assemble the grasper magnet 258, the magnet ferrule 268, and the magnet wire 260, the magnet wire 260 is first passed through the magnet ferrule 268 from its distal end to its proximal end, so that the magnet wire distal terminus 266 becomes positioned inside the magnet ferrule 268. The grasper magnet 258 is then installed from the distal end, and attached to the magnet ferrule 268. The grasper magnet 258 can be attached by mechanical means, e.g., swaged, threaded, interference fit, pinned, etc., or adhesive means or other means, e.g., welding, brazing, etc. Once the grasper magnet 258 is attached, the magnet wire distal terminus 266 is permanently captured between the grasper magnet 258 and the magnet ferrule 268, and the sub-assembly is complete.

Figure 16:
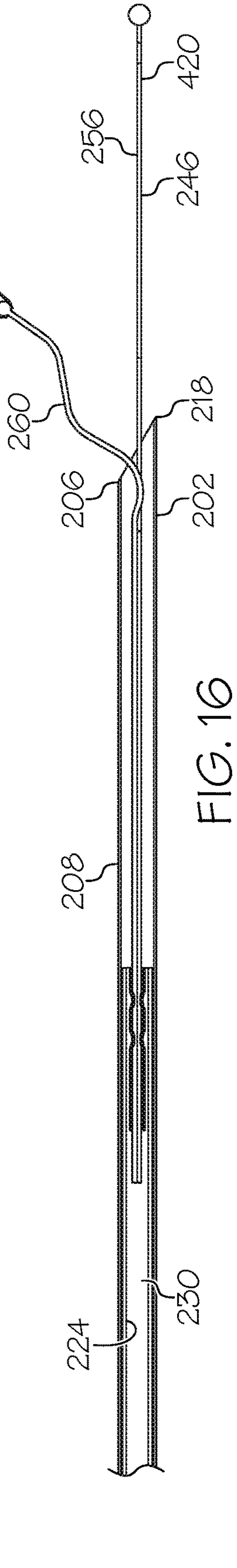
FIG. 16 is an expanded sectional view of the magnet-assisted suture grasper of FIG. 15.

As shown in FIGS. 16-18, in some embodiments, the grasper magnet 258 is displaced radially from the needle body axis 210 when the grasper member 246 is in the second position 256. This can be advantageous by providing an operator of the magnet-assisted suture grasper 200 an additional range of motion to move the grasper magnet 258 within a site of a patient by rotation of the magnet-assisted suture grasper 200 and thus greater versatility in positioning the grasper magnet 258 relative to a magnetic suture 500 in the site.

Figure 8:
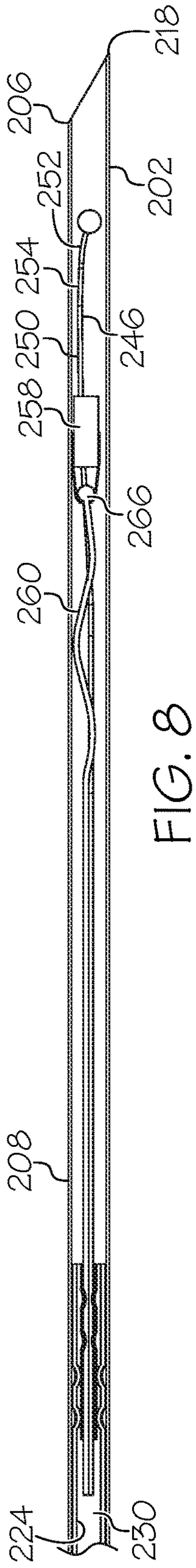
FIG. 8 is an expanded sectional view of the magnet-assisted suture grasper of FIG. 7, in which the advancer assembly of the device is in a locked partially retracted position and the grasper member is in the first position.
Figure 9:
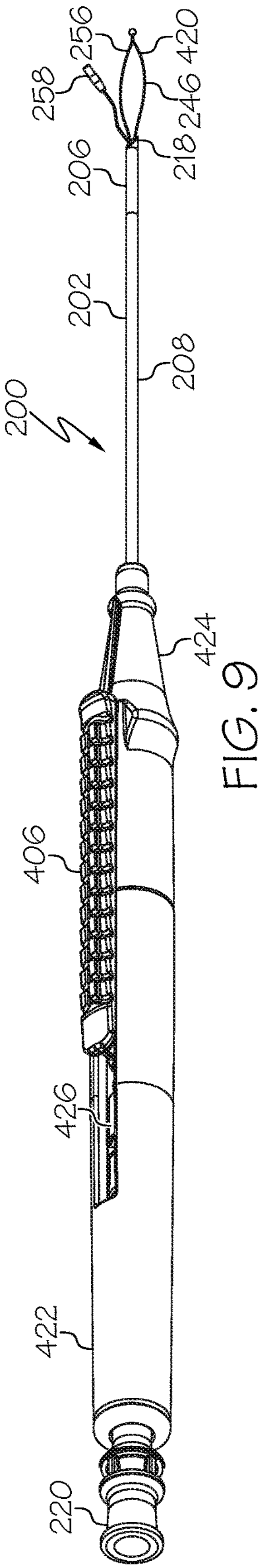
FIG. 9 is a perspective view of the magnet-assisted suture grasper of FIG. 1 in which the advancer assembly of the device is in a fully extended position, the grasper member is in a second position, and the grasper magnet is exposed, allowing contact between the grasper magnet and a magnetic suture attracted thereto.
Figure 10:
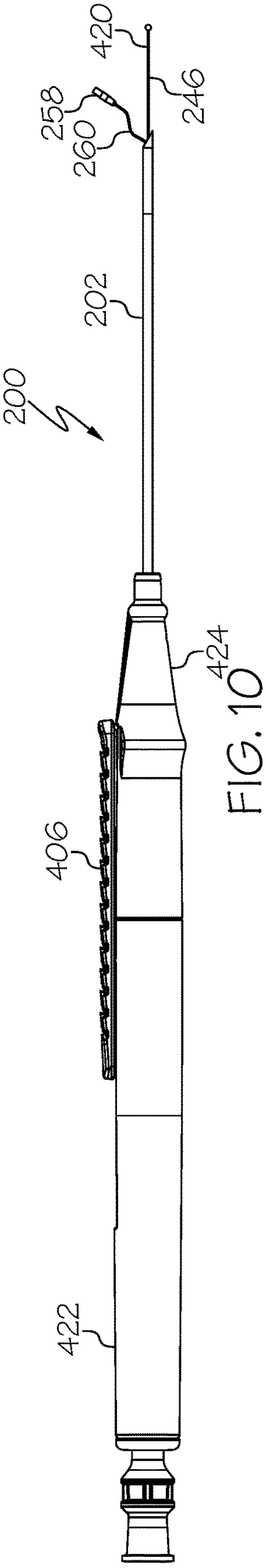
FIG. 10 is a side view of the magnet-assisted suture grasper of FIG. 9.
Figure 11:
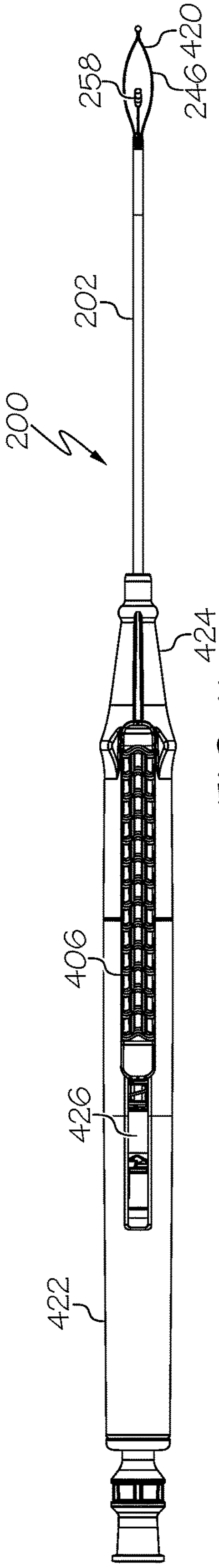
FIG. 11 is a top view of the magnet-assisted suture grasper of FIG. 9.
Figure 12:
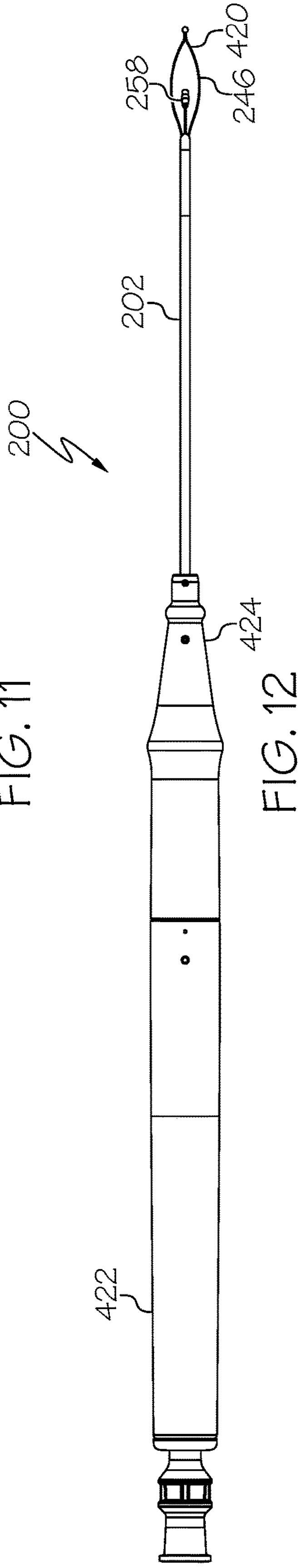
FIG. 12 is a bottom view of the magnet-assisted suture grasper of FIG. 9.
Figure 14:
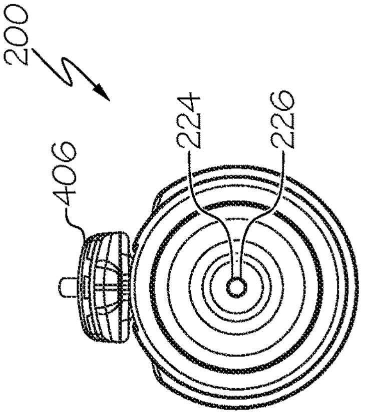
FIG. 14 is a back view of the magnet-assisted suture grasper of FIG. 9.
Figure 13:
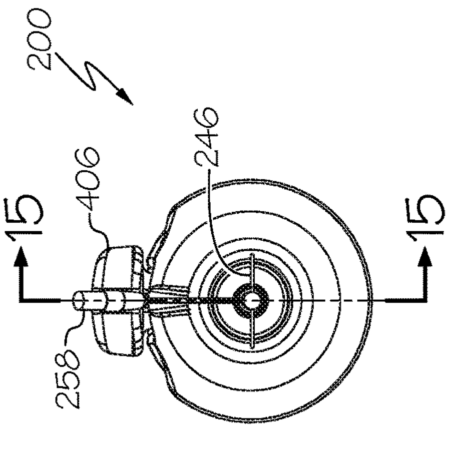
FIG. 13 is a front view of the magnet-assisted suture grasper of FIG. 9.
Figure 15:
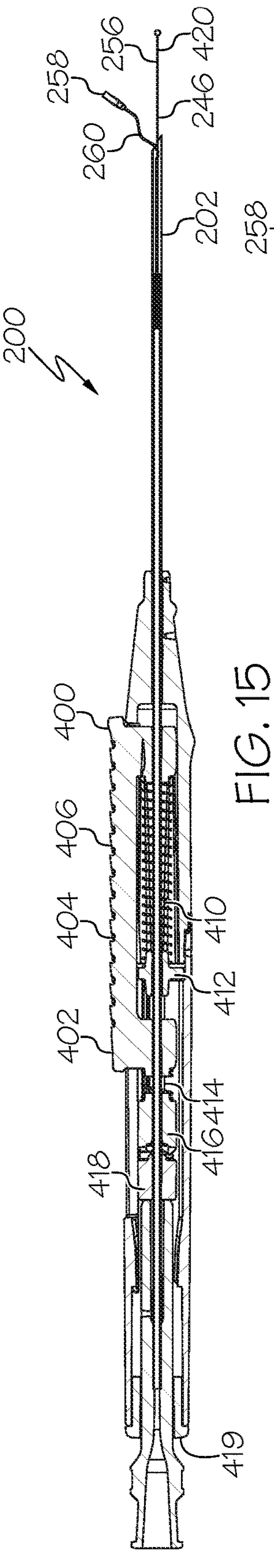
FIG. 15 is a sectional view of the magnet-assisted suture grasper of FIG. 9, viewed along the cutting plane shown in FIG. 13.

As shown in FIG. 8 and FIG. 16, the distal portion of the grasper member 246 extends further distally than the grasper magnet 258. This means that when the grasper member 246 is in the first position 254 that the distal portion 252 of the grasper member 246 extends further distally within the needle lumen 216 than does any portion of the grasper magnet 258. This also means that when the grasper member 246 is in the second position 256 that the distal portion 252 of the grasper member 246 extends further distally from the suture retrieval needle 202 than does any portion of the grasper magnet 258. This also means that when the grasper member 246 is in the second position 256 that the grasper magnet 258 is closer to the distal end 206 of the suture retrieval needle 202 than is the distal portion 252 of the grasper member 246.

With reference to FIG. 8, FIG. 16, and FIGS. 84-87, translation of the retriever tube 224 within the needle lumen 216 in a first direction along the needle body axis 210 causes the grasper member 246 to move from the first position 254 to the second position 256, thereby exposing the grasper magnet 258 and allowing contact between the grasper magnet 258 and a magnetic suture 500 attracted thereto. The translation of the retriever tube 224 results in translation of the grasper member 246. The translation of the retriever tube 224 in the first direction can be translation of the retriever tube 224 within the needle lumen 216 in a direction from the proximal end 204 of the suture retrieval needle 202 toward the distal end 206 of the suture retrieval needle 202. When the grasper member 246 is in the first position 254 the grasper magnet 258 can be disposed entirely inside the needle lumen 216, and thus sequestered within the needle lumen 216. In accordance with these embodiments, such translation of the retriever tube 224 within the needle lumen 216 in the first direction can move the grasper magnet 258 from inside the needle lumen 216 to outside the needle lumen 216, thus exposing the grasper magnet 258.

The grasper member 246 is made to be sufficiently stiff so that translation of the retriever tube 224 within the needle lumen 216 in the first direction moves the grasper member 246 from inside the needle lumen 216 to outside the needle lumen 216, thus exposing the grasper magnet 258.

Translation of the retriever tube 224 within the needle lumen 216 in a second direction opposite the first direction along the needle body axis 210 causes the grasper member 246 to move from the second position 256 to the first position 254, thereby sequestering the grasper magnet 258 and grasping the magnetic suture 500 within the needle lumen 216. The translation of the retriever tube 224 in the second direction can be translation of the retriever tube 224 within the needle lumen 216 in a direction from the distal end 206 of suture retrieval needle 202 toward the proximal end 204 of the suture retrieval needle 202. Such translation of the retriever tube 224 within the needle lumen 216 in the second direction can move the grasper magnet 258 from outside the needle lumen 216 to inside the needle lumen 216, thus sequestering the grasper magnet 258 again and grasping the magnetic suture 500 within the needle lumen 216.

This can be accomplished as follows. Because the grasper magnet 258 is closer to the distal end 206 of the suture retrieval needle 202 than is the distal portion 252 of the grasper member 246 while the grasper member 246 is in the second position 256, when a suture magnet 502 of a magnetic suture 500 contacts the grasper magnet 258 and the retriever tube 224 is translated in the second direction to the first position 254, the grasper magnet 258 and the suture magnet 502 of the magnetic suture 500 enter the needle lumen 216 before the distal portion 252 of the grasper member 246 does. Once the distal portion 252 of the grasper member 246 has followed the suture magnet 502 into the needle lumen 216, the suture magnet 502 cannot exit the needle lumen 216 while the distal portion 252 of the grasper member 246 remains in the needle lumen 216. The grasper member 246 blocks exit of the suture magnet 502, thereby mechanically capturing the magnetic suture 500. The suture magnet 502 of the magnetic suture 500 thus can be grasped by the grasper member 246 as the magnet-assisted suture grasper 200 is used to pull the magnetic suture 500 through soft tissue of a patient. The grasper member 246 is sufficiently strong to resist the frictional drag that results from pulling the magnetic suture 500 through the soft tissue.

As noted above, the grasper member 246 comprises a proximal portion 248, an intermediate portion 250, and a distal portion 252. Also as noted, the grasper magnet 258 is disposed adjacent the intermediate portion 250 of the grasper member 246. The grasper member 246 has a length and orientation sufficient to allow the suture magnet 502 of a magnetic suture 500 to fit between the grasper magnet 258 and the distal portion 252 of the grasper member 246 when the grasper member 246 is in the second position 256, so that the suture magnet 502 of the magnetic suture 500 can contact the grasper magnet 258 for magnetic attraction, and when the grasper member 246 has been returned to the first position 254, so that the suture magnet 502 of the magnetic suture 500 can fit within the needle lumen 216 along with the grasper magnet 258 and the grasper member 246 for mechanical capture. The intermediate portion 250 of the grasper member 246 adjacent to which the grasper magnet 258 is disposed can be any portion of the grasper member 246 distal to the proximal portion 248 of the grasper member 246 and proximal to the distal portion 252 of the grasper member 246, so long as sufficient space is provided for a suture magnet 502 to fit between the grasper magnet 258 and the distal portion 252 of the grasper member 246.

In some embodiments, translation of the retriever tube 224 within the needle lumen 216 is limited to a straight path as the translation of the retriever tube 224 causes the grasper member 246 to move between the first position 254 and the second positions 256. As noted above, in some embodiments, the suture retrieval needle 202 includes a curve at or near its distal end 206 but otherwise is straight. Limiting translation of the retriever tube 224 within the needle lumen 216 to a straight path as the translation of the retriever tube 224 causes the grasper member 246 to move between the first position 254 and the second positions 256 can be advantageous because it allows use of a retriever tube 224 that is made of a rigid material, such as stainless steel, while also allowing use of a suture retrieval needle 202 that includes a curve at or near its distal end 206 but otherwise is straight. In accordance with these embodiments, the grasper member 246 and the magnet wire 260 can be made to sufficient lengths and with sufficient flexibilities to pass through the needle lumen 216 at the curve of the suture retrieval needle 202 without the retriever tube 224 needing to do so.

As noted above, the grasper ferrule 232 is fixedly disposed within the retriever tube 224. Also as noted, the grasper member 246 extends distally from the grasper ferrule 232, for example based on the proximal portion 248 of the grasper member 246 being fixedly disposed within the grasper ferrule 232, or based on the grasper member 246 being integral to the grasper ferrule 232. Also as noted, the proximal portion 262 of the magnet wire 260 is fixedly disposed within the grasper ferrule 232. Thus, the grasper member 246 and the magnet wire 260 are translationally and rotationally fixed to the retriever tube 224 via the grasper ferrule 232.

With reference to FIGS. 29-40, the grasper ferrule 232 can be used to fixedly attach the grasper member 246 and the magnet wire 260 to the retriever tube 224 by various approaches.

Figure 33:
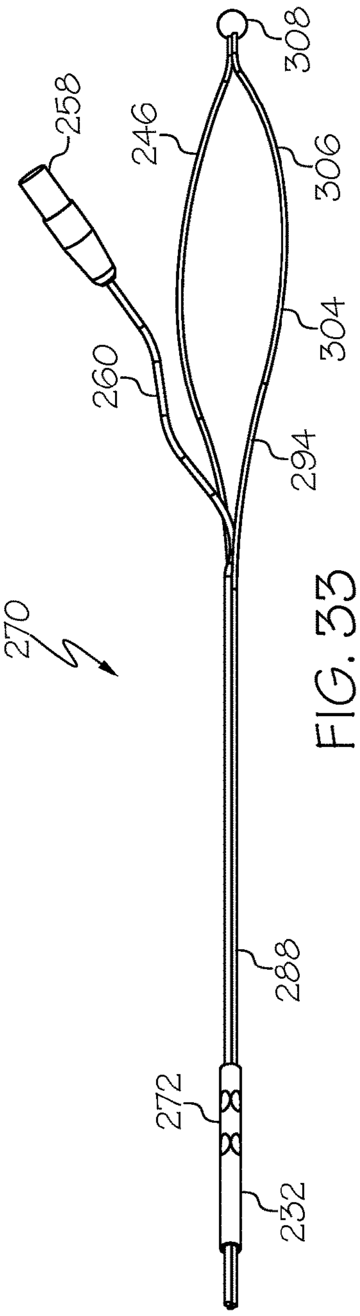
FIG. 33 is a perspective view of the grasper ferrule, the grasper member, the grasper magnet, and the magnet wire of the magnet-assisted suture grasper of FIG. 1, in which the grasper ferrule has been crimped onto the grasper member and the magnet wire.
Figure 34:
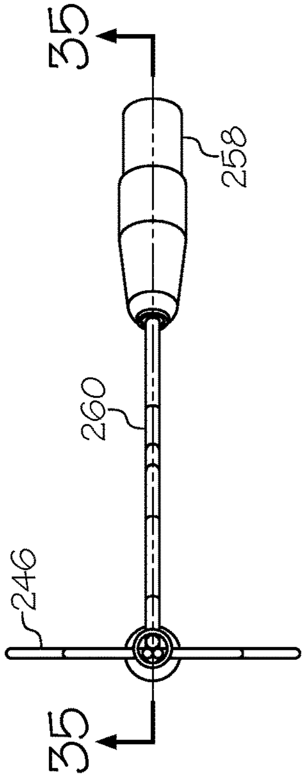
FIG. 34 is a back view of the grasper ferrule, the grasper member, the grasper magnet, and the magnet wire of FIG. 33.
Figure 35:
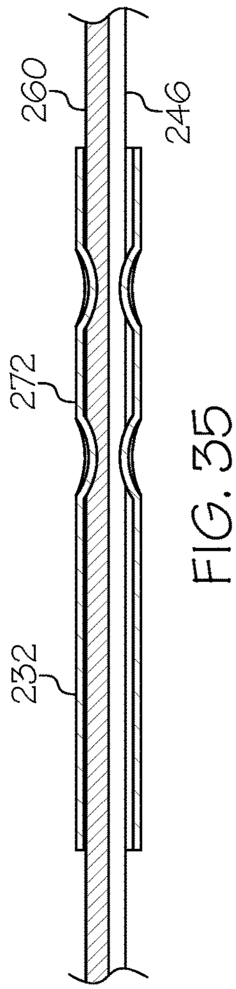
FIG. 35 is an expanded sectional view of the grasper ferrule, the grasper member, and the magnet wire of FIG. 33, viewed along the cutting plane shown in FIG. 32.

In some approaches, for embodiments in which the grasper member 246 and the magnet wire 260 extend distally from the grasper ferrule 232 based on the proximal portion 248 of the grasper member 246 and the proximal portion 262 of the magnet wire 260 being fixedly disposed within the grasper ferrule 232, a grasper ferrule subassembly 270 including the grasper member 246, the magnet wire 260, and the grasper ferrule 232 can be assembled as follows. The proximal portion 248 of the grasper member 246 and the proximal portion 262 of the magnet wire 260 are inserted into the ferrule lumen 244 of the grasper ferrule 232 via the distal hole 242 of the grasper ferrule 232, as shown with reference to FIGS. 29-32. The grasper ferrule 232 is crimped onto the proximal portion 248 of the grasper member 246 and the proximal portion 262 of the magnet wire 260, elastically and plastically deforming the grasper ferrule 232, the proximal portion 248 of the grasper member 246, and the proximal portion 262 of the magnet wire 260. This creates an inner crimp joint 272, as shown in FIGS. 33-35.

The inner crimp joint 272 is a permanent mechanical joint. This provides advantages relative to an adhesive joint. The advantages include greater speed and throughput, as a crimp joint takes approximately 10 to 95% less time to complete than a comparable adhesive joint, with timing depending on the adhesive used. Moreover, a crimp joint provides strong attachment immediately upon completion of crimping, whereas an adhesive joint may require special handling until the adhesive cures. The advantages also include greater chemical compatibility. Since a crimp joint is an entirely mechanical joint, it does not rely on intermolecular bonds of an adhesive to keep the parts attached, and thus will not lose strength when exposed to environmental agents that can cause the intermolecular bonds to fail. In addition, regarding metal crimp joints in particular, e.g., for a grasper ferrule 232, a grasper member 246, and a magnet wire 260 that are each made from metals, advantages also include increased stability and shelf life. As polymeric materials age, macroscopic changes in the physical and chemical properties of the polymeric materials occur over time due to molecular-level relaxations of the polymer chains and continued chemical reactions. These changes tend to negatively affect the strength and toughness of an adhesive joint. Metals exhibit far less structural changes than polymers over the same time and temperature ranges. Therefore, a crimp joint such as the one described, which consists entirely of metallic components, with no polymeric interface, will generally be more stable over time and will thus be less-susceptible to age-related degradation.

Figure 36:
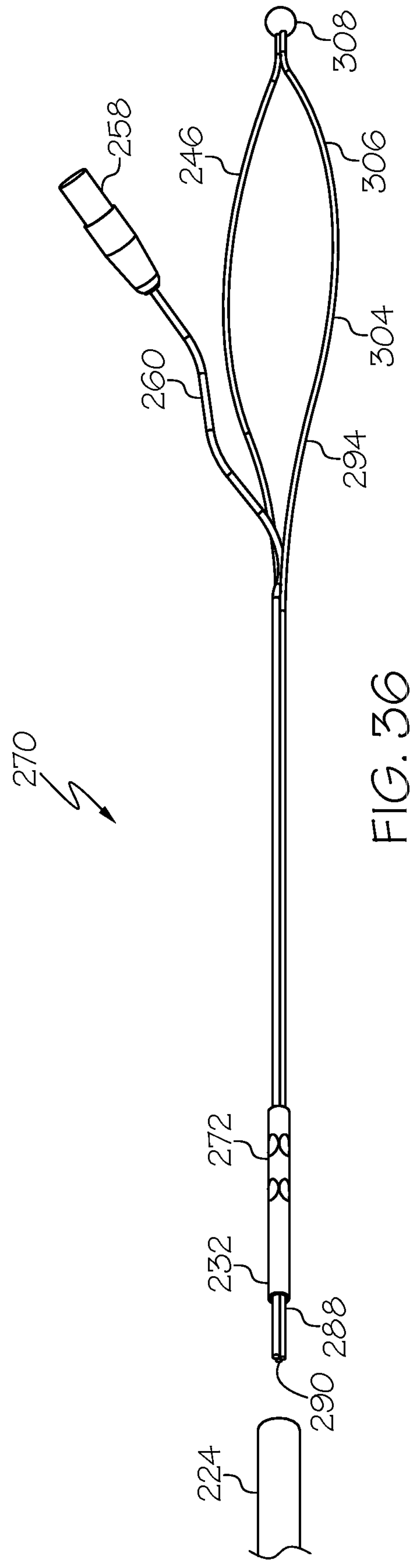
FIG. 36 is an exploded perspective view of the retriever tube, the grasper ferrule, the grasper member, the grasper magnet, and the magnet wire of the magnet-assisted suture grasper of FIG. 1, in which the grasper ferrule has been crimped onto the grasper member and the magnet wire.
Figure 37:
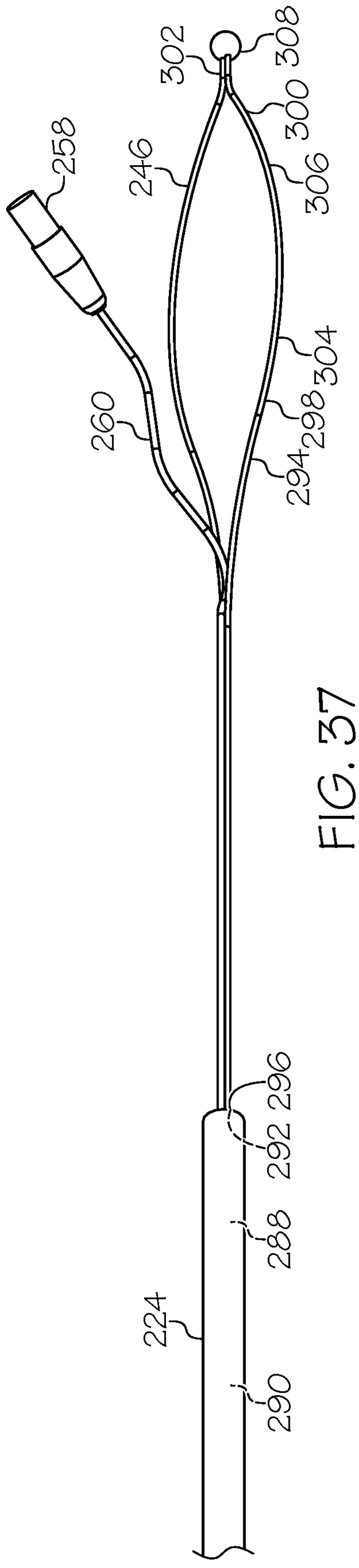
FIG. 37 is a perspective view of the retriever tube, the grasper ferrule, the grasper member, the grasper magnet, and the magnet wire of the magnet-assisted suture grasper of FIG. 1, in which the grasper ferrule has been crimped onto the grasper member and the magnet wire.
Figure 39:
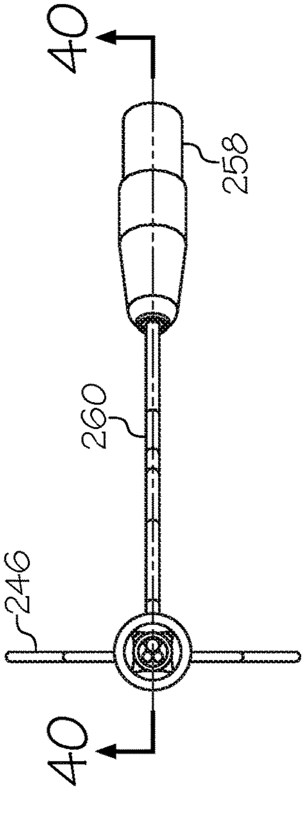
FIG. 39 is a back view of the retriever tube, the grasper ferrule, the grasper member, the grasper magnet, and the magnet wire of FIG. 38.
Figure 40:
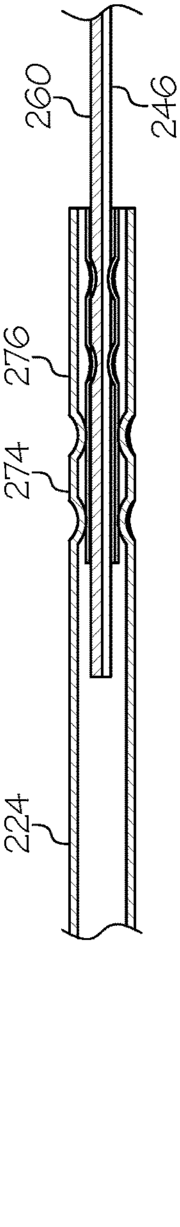
FIG. 40 is an expanded side sectional view of the retriever tube, the grasper ferrule, the grasper member, and the magnet wire of FIG. 38, viewed along the cutting plane shown in FIG. 39.

The grasper ferrule subassembly 270 is then inserted into the retriever tube lumen 230 of the retriever tube 224 via the distal hole 228 of the retriever tube 224, as shown with reference to FIG. 36 and FIG. 37. The grasper ferrule subassembly 270 can be inserted such that the grasper ferrule 232 is disposed entirely within the retriever tube lumen 230, with the distal end 236 of the grasper ferrule 232 being adjacent the distal hole 228 of the retriever tube 224. The retriever tube 224 is crimped onto the grasper ferrule 232. This creates an outer crimp joint 274, as shown in FIGS. 38-40.

The outer crimp joint 274 permanently joins the grasper member 246, the magnet wire 260, and the grasper ferrule 232 to the retriever tube 224, with similar advantages as described above regarding the inner crimp joint 272 of the grasper ferrule subassembly 270.

Figure 38:
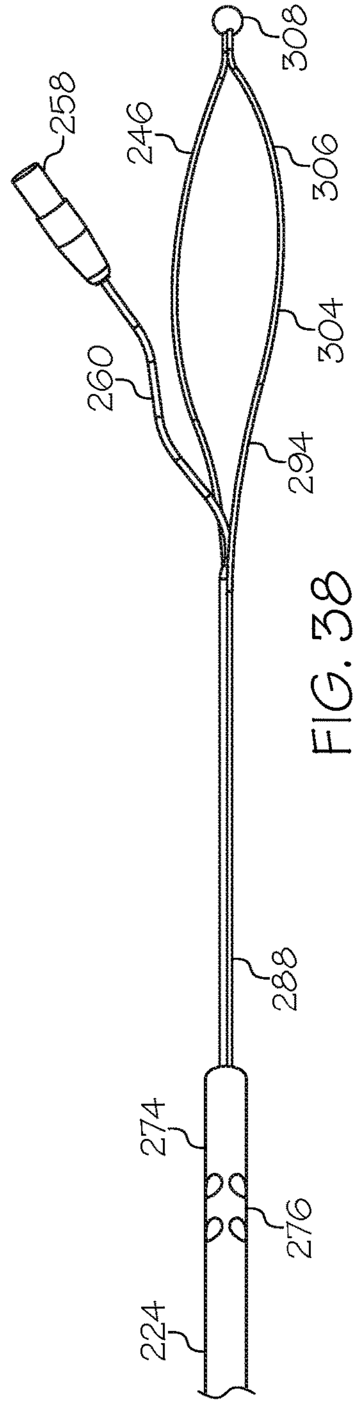
FIG. 38 is a perspective view of the retriever tube, the grasper ferrule, the grasper member, the grasper magnet, and the magnet wire of FIG. 37, in which the retriever tube has been crimped onto the grasper ferrule.
Figure 41:
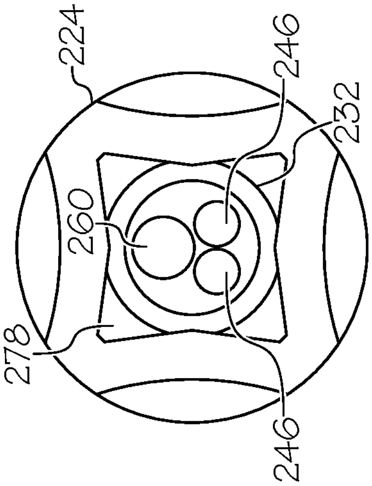
FIG. 41 is cross-sectional view of the retriever tube, the grasper ferrule, the grasper member, and the magnet wire of FIG. 38.
Figure 42:
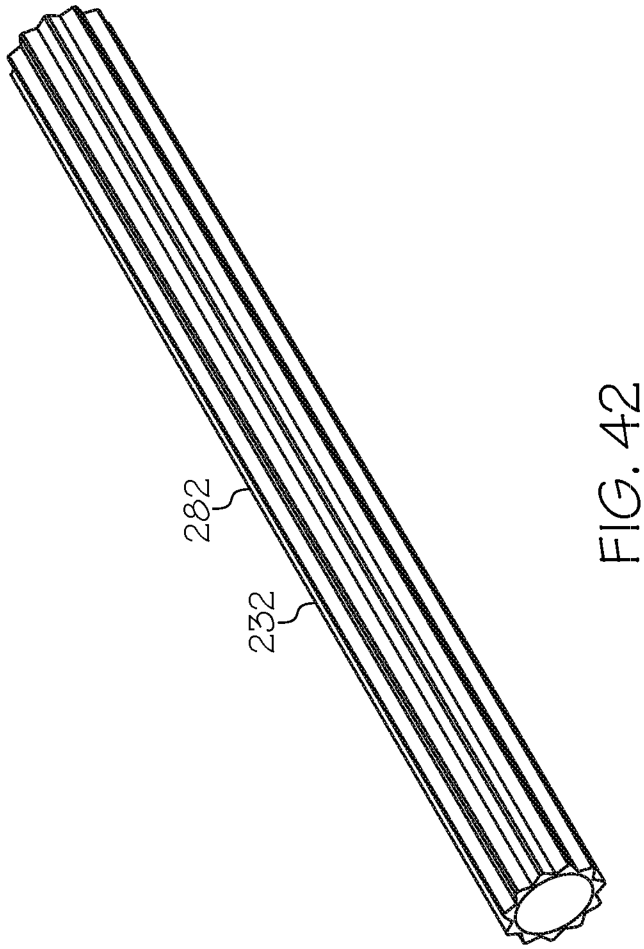
FIG. 42 is a side view of an alternative embodiment of a grasper ferrule of the magnet-assisted suture grasper of FIG. 1, in which the grasper ferrule is a knurled grasper ferrule.
Figure 43:
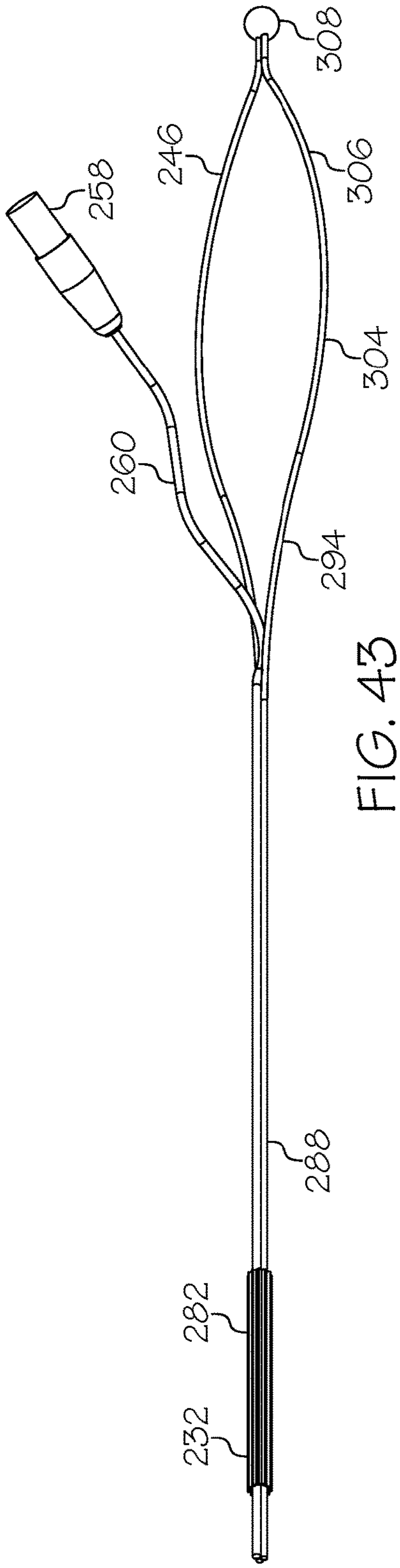
FIG. 43 is a perspective view of the knurled grasper ferrule and the grasper member, the grasper magnet, and the magnet wire of the magnet-assisted suture grasper of FIG. 1.
Figure 44:
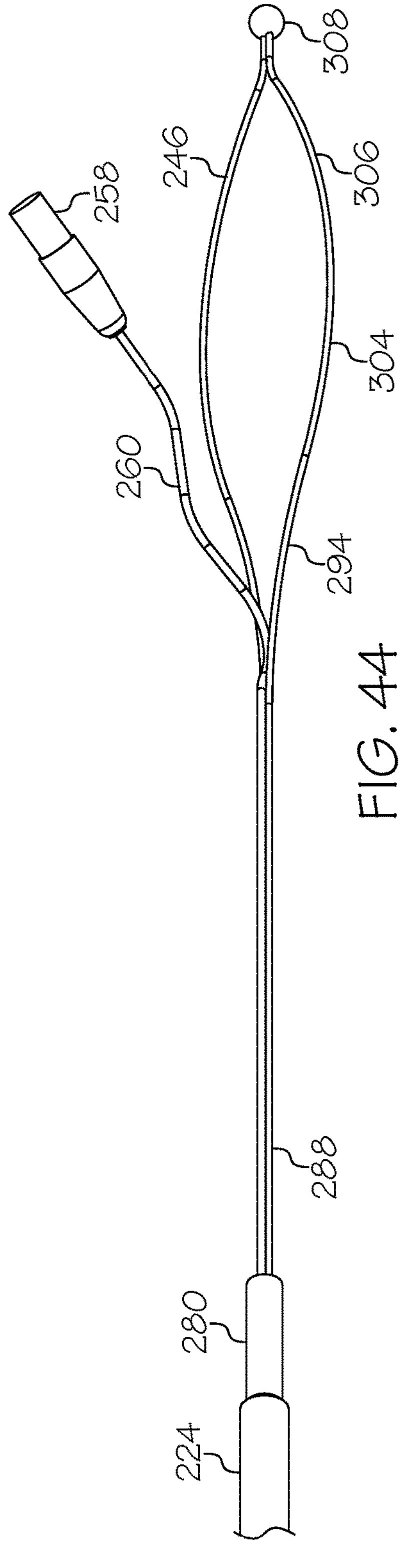
FIG. 44 is a perspective view of the knurled grasper ferrule and the retriever tube, the grasper member, the grasper magnet, and the magnet wire of the magnet-assisted suture grasper of FIG. 1.
Figure 45:
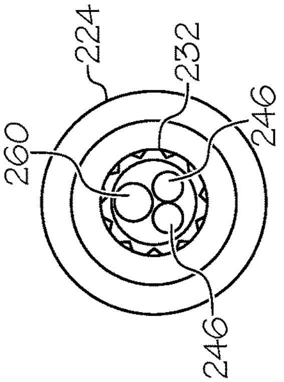
FIG. 45 is cross-sectional view of the knurled grasper ferrule and the retriever tube, the grasper member, the grasper magnet, and the magnet wire of FIG. 44.
Figure 46:
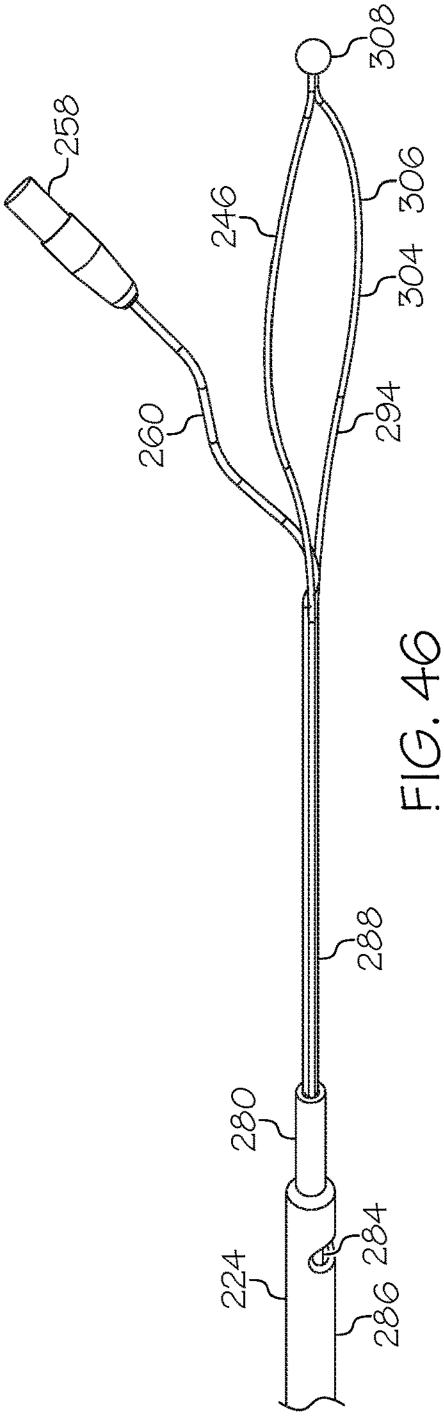
FIG. 46 is a perspective view of an alternative embodiment of a retriever tube of the magnet-assisted suture grasper of FIG. 1, in which the retriever tube is a retriever tube including a retriever tube intermediate hole, and the grasper ferrule, the grasper member, the grasper magnet, and the magnet wire of the magnet-assisted suture grasper of FIG. 1.
Figure 47:
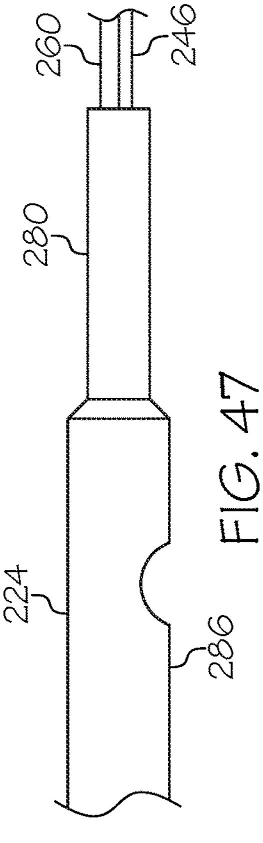
FIG. 47 is a side view of the retriever tube including a retriever tube intermediate hole and the grasper ferrule, the grasper member, and the magnet wire of FIG. 46.
Figure 48:
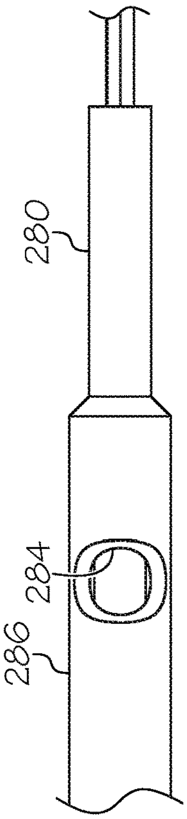
FIG. 48 is a bottom view of the retriever tube including a retriever tube intermediate hole and the grasper ferrule, the grasper member, and the magnet wire of FIG. 46.
Figure 49:
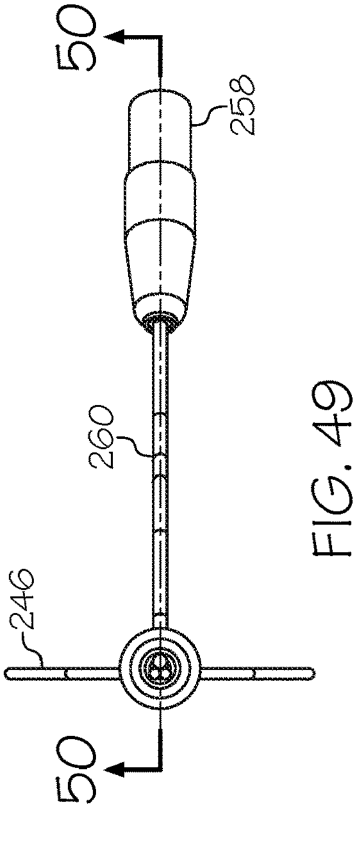
FIG. 49 is a back view of the retriever tube including a retriever tube intermediate hole and the grasper ferrule, the grasper member, and the magnet wire of FIG. 46.
Figure 50:
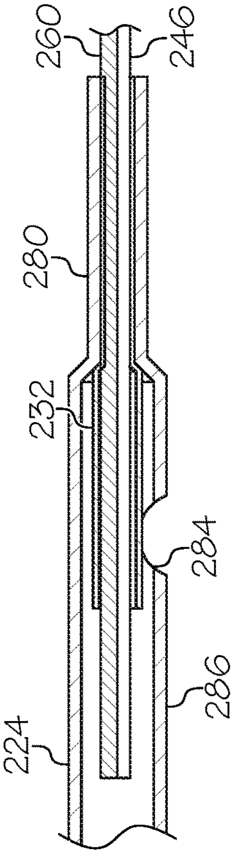
FIG. 50 is an expanded side sectional view of the retriever tube including a retriever tube intermediate hole and the grasper ferrule, the grasper member, and the magnet wire of FIG. 46, viewed along the cutting plane shown in FIG. 49.
Figure 51:
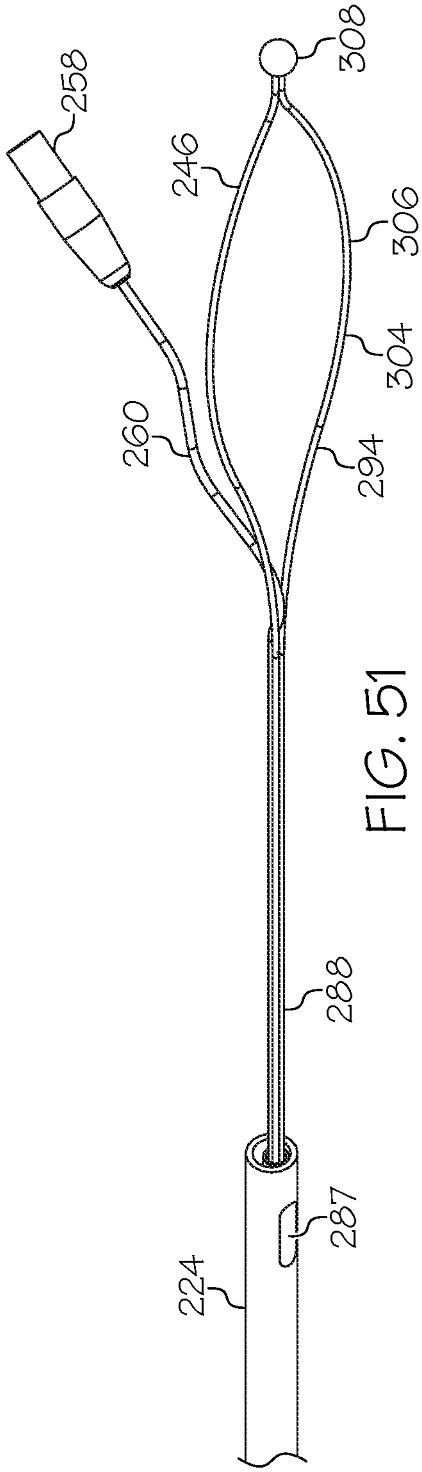
FIG. 51 is a perspective view of the retriever tube, the grasper ferrule, the grasper member, the grasper magnet, and the magnet wire of the magnet-assisted suture grasper of FIG. 1, in which the grasper ferrule has been crimped onto the grasper member and the magnet wire, and the grasper ferrule has been welded to the retriever tube.
Figure 52:
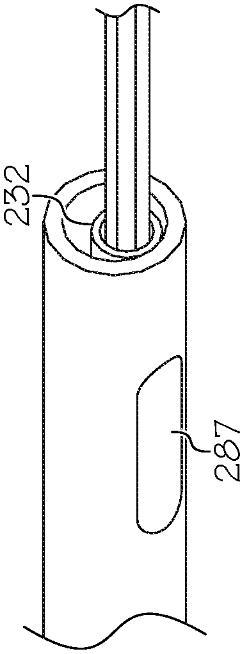
FIG. 52 is an expanded perspective view of the retriever tube, the grasper ferrule, the grasper member, and the magnet wire of FIG. 51.
Figure 53:
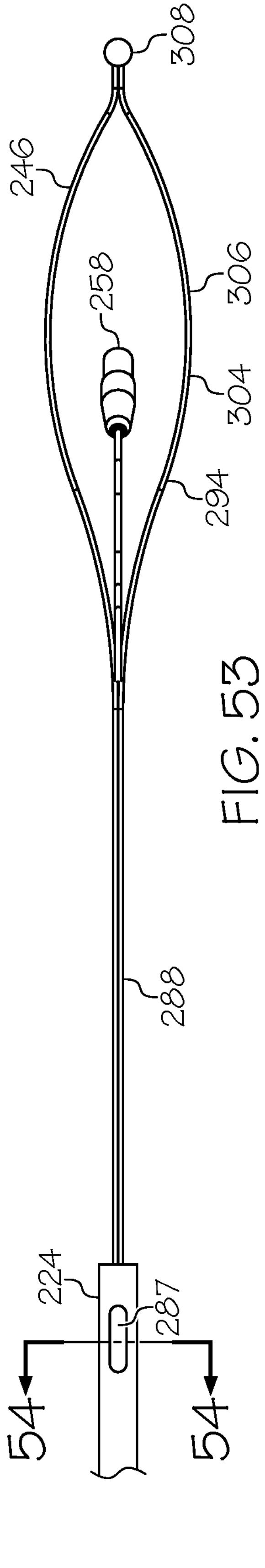
FIG. 53 is a bottom view of the retriever tube, the grasper ferrule, the grasper member, the grasper magnet, and the magnet wire of FIG. 52.
Figure 54:
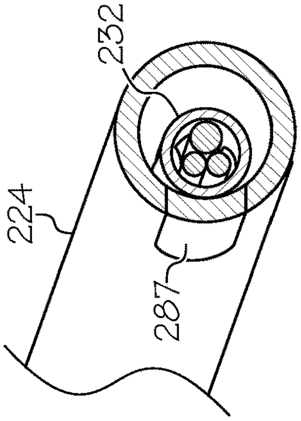
FIG. 54 is a perspective sectional view of the retriever tube, the grasper ferrule, the grasper member, and the magnet wire of FIG. 51, viewed along the cutting plane shown in FIG. 53.

The outer crimp joint 274 can be made with an interrupted crimping pattern 276, as shown in FIG. 38. This can be accomplished by use of a crimp tool including one or more distinct segments, also termed teeth, with gaps therebetween. The resulting outer crimp joint 274 with the interrupted crimping pattern 276 includes gaps 278 between locally yielded areas of the grasper ferrule 232 and the retriever tube 224 that provide paths to allow liquids and gasses to flow through the crimp joint, as shown in FIG. 41.

In other approaches, for embodiments in which the grasper member 246 and the magnet wire 260 extend distally from the grasper ferrule 232 based on the proximal portion 248 of the grasper member 246 and the proximal portion 262 of the magnet wire 260 being disposed adjacent the grasper ferrule 232 and not within the ferrule lumen 244 of the grasper ferrule 232, the grasper ferrule 232, the proximal portion 248 of the grasper member 246, and the proximal portion 262 of the magnet wire 260 can be inserted into the retriever tube lumen 230 of a retriever tube 224 with the proximal portion 248 of the grasper member 246 and the proximal portion 262 of the magnet wire 260 being disposed adjacent the grasper ferrule 232 and not within the ferrule lumen 244 of the grasper ferrule 232. The retriever tube 224 is then crimped onto the grasper ferrule 232, the proximal portion 248 of the grasper member 246, and the proximal portion 262 of the magnet wire 260 to form an outer crimp joint 274. In these embodiments, no inner crimp joint 272 is formed. The grasper ferrule 232 is included to help control the depth of the crimp. The inner crimp joint 272 may be omitted when the outer crimp joint 274 is made with a depth of crimp sufficient to deform the grasper ferrule 232 deeply enough to capture the grasper member 246 and magnet wire 260. This allows for assembly of the relevant parts in a single step, followed by crimping of the retriever tube 224 onto the grasper ferrule 232 to join all relevant parts by the outer crimp joint 274. This also advantageously maintains a relatively larger open cross-sectional area within the outer crimp joint.

In other approaches, for embodiments in which the grasper member 246 extends distally from the grasper ferrule 232 based on the grasper member 246 being integral to the grasper ferrule 232, the proximal portion 262 of the magnet wire 260 is inserted into the ferrule lumen 244 of the grasper ferrule 232 via the distal hole 242 of the grasper ferrule 232, followed by crimping to create an inner crimp joint 272, as described above. Then the grasper ferrule subassembly 270 is inserted into the retriever tube lumen 230 of the retriever tube 224 via the distal hole 228 of the retriever tube 224. Again, the grasper ferrule subassembly 270 can be inserted such that the grasper ferrule 232 is disposed entirely within the retriever tube lumen 230, with the distal end 236 of the grasper ferrule 232 being adjacent the distal hole 228 of the retriever tube 224. This is followed by crimping to create an outer crimp joint 274, again as described above, including the outer crimp joint 274 being made with an interrupted crimping pattern 276 providing gaps 278 as described above. Alternatively, for these embodiments, the grasper ferrule 232 and the proximal portion 262 of the magnet wire 260 can be inserted into the retriever tube lumen 230 of a retriever tube 224 with the proximal portion 262 of the magnet wire 260 being disposed adjacent the grasper ferrule 232 and not within the ferrule lumen 244 of the grasper ferrule 232. The retriever tube 224 is then crimped onto the grasper ferrule 232 and the proximal portion 262 of the magnet wire 260 to form an outer crimp joint 274, without forming an inner crimp joint 272, also as discussed above.

In other approaches, applicable to embodiments in which the grasper member 246 and the magnet wire 260 extend distally from the grasper ferrule 232 based on the proximal portion 248 of the grasper member 246 and the proximal portion 262 of the magnet wire 260 being fixedly disposed within the grasper ferrule 232 or based on the grasper member 246 being integral to the grasper ferrule 232, the inner crimp joint 272 may be omitted when the outer crimp joint 274 is made with a depth of crimp sufficient to deform the grasper ferrule 232 deeply enough to capture the grasper member 246 and magnet wire 260 or the magnet wire 260 alone. As described above, this allows for assembly of the relevant parts in a single step, followed by crimping of the retriever tube 224 onto the grasper ferrule 232 to join all relevant parts by the outer crimp joint 274.

With reference to FIGS. 42-45, also in other approaches, also applicable to embodiments in which the grasper member 246 and the magnet wire 260 extend distally from the grasper ferrule 232 based on the proximal portion 248 of the grasper member 246 and the proximal portion 262 of the magnet wire 260 being fixedly disposed within the grasper ferrule 232 or based on the grasper member 246 being integral to the grasper ferrule 232, a radially swaged joint 280 or uninterrupted crimp joint may allow for a heavier depth of crimp, with less undesirable deformation, i.e. off-axis deflection, than can be achieved with an interrupted crimping pattern 276. The benefit of a heavier depth of crimp is that it generally provides for a stronger joint, up to a point, as there is limit to how much the metal can stretch before tears and/or cracks begin to form.

By applying one or more grooves or projections to the inner diameter of the retriever tube 224 or outer diameter of the grasper ferrule 232, a flow path can be created through the swaged joint 280.

For example, in some embodiments a knurl 282, such as a straight-patterned knurl, is applied to the outer diameter of the grasper ferrule 232. As the retriever tube 224 is swaged onto the grasper ferrule 232, the inner diameter of the retriever tube 224 contacts the peaks of the knurl 282, and the resulting local yielding of both the grasper ferrule 232 and retriever tube 224 completes the mechanical joint. After assembly, the valleys created by the knurl 282 on the grasper ferrule 232 provide the paths for liquids and/or gasses to flow through the swaged joint 280.

Also for example, in some embodiments the knurl 282 may be applied to the inner diameter of the retriever tube 224, rather than the outer diameter of the grasper ferrule 232. Also alternatively, a different knurl pattern, such as a helical knurl pattern or a diamond knurl pattern, may be used instead of a straight-patterned knurl. Also alternatively, a series of one or more grooves may be created by milling, scraping, grinding, or broaching the grasper ferrule 232 and/or the retriever tube 224. A screw thread with one or more leads may be considered a special case of a helical knurl, and the thread may be applied to the male grasper ferrule 232 or female retriever tube 224 component.

As shown in FIGS. 46-50, also for example, in some embodiments the retriever tube 224 has a retriever tube intermediate hole 284 through a wall 286 of the retriever tube 224, proximal to a swaged joint 280. The retriever tube intermediate hole 284 can provide a path for liquid and/or gasses to exit the retriever tube 224.

As shown in FIGS. 51-54, also in other approaches, applicable to embodiments in which the grasper member 246 and the magnet wire 260 extend distally from the grasper ferrule 232 based on the proximal portion 248 of the grasper member 246 and the proximal portion 262 of the magnet wire 260 being fixedly disposed within the grasper ferrule 232 or based on the grasper member 246 being integral to the grasper ferrule 232, the grasper ferrule subassembly 270 can be made by creating an inner crimp joint 272 as described above, the grasper ferrule subassembly 270 can be inserted into the retriever tube lumen 230 also as described above, and then the grasper ferrule 232 can be fixedly attached to the retriever tube 224 by approaches other than crimping, such as welding, to form a welded site 287.

Thus, in some embodiments, the grasper ferrule 232 has been crimped onto the grasper member 246 and the magnet wire 260 with the proximal portion 248 of the grasper member 246 and the proximal portion 262 of the magnet wire 260 being disposed within the ferrule lumen 244 of the grasper ferrule 232, and the retriever tube 224 has been crimped onto the grasper ferrule 232 with the grasper ferrule 232, the proximal portion 248 of the grasper member 246, and the proximal portion 262 of the magnet wire 260 being disposed within the retriever tube lumen 230.

Also, in some embodiments, the retriever tube 224 has been crimped onto the grasper ferrule 232, the proximal portion 248 of the grasper member 246, and the proximal portion 262 of the magnet wire 260, with the grasper ferrule 232, the proximal portion 248 of the grasper member 246, and the proximal portion 262 of the magnet wire 260 being disposed within the retriever tube lumen 230, and with the proximal portion 248 of the grasper member 246 and the proximal portion 262 of the magnet wire 260 being disposed adjacent the grasper ferrule 232 and not within the ferrule lumen 244 of the grasper ferrule 232.

Considering the grasper member 246 in more detail, as shown in FIG. 24 and FIG. 84, in some embodiments, the grasper member 246 comprises: (i) a grasper wire 288 having a proximal end 290 and a distal end 292, and (ii) a grasper arm 294 comprising a proximal end 296, a proximal-to-intermediate portion 298, a distal portion 300, and a distal end 302.

In accordance with these embodiments, the grasper wire 288 can be, for example, a metal wire, such as a Nitinol wire or a stainless steel wire, or a plastic wire, among other types of wire. The grasper wire 288 can be formed, for example, as a solid wire, a stranded wire, or a braided wire. The grasper wire 288 can have a shape, for example, based on being a shaped wire and/or a stamped wire. The grasper wire 288 can comprise, for example, one or more wires joined together at one or more common points, for example, by welding, soldering, braiding, crimping, adhesive, or other means.

Also in accordance with these embodiments, the grasper arm 294 also can be, for example, a wire, although other structures, such as a tube or other elongated member can be suitable too. Regarding the grasper arm 294 being a wire, the grasper arm 294 can be, for example, a metal wire, such as a Nitinol wire or a stainless steel wire, or a plastic wire, and can be formed, for example, as a solid wire, a stranded wire, or a braided wire, and can have a shape, for example, based on being a shaped wire and/or a stamped wire, and can comprise, for example, one or more wires joined together at one or more common points, for example, by welding, soldering, braiding, crimping, adhesive, or other means.

Also, in accordance with these embodiments, the grasper wire 288 is fixedly disposed within the grasper ferrule 232, or adjacent the grasper ferrule 232 and not within the ferrule lumen 244 of the grasper ferrule 232.

Also, in accordance with these embodiments, the grasper wire extends distally from the ferrule lumen.

Also in accordance with these embodiments, the grasper arm 294 extends from the distal end 292 of the grasper wire 288 and is reversibly moveable between the first position 254 and the second position 256.

As shown in FIG. 24 and FIG. 84, in some of these embodiments, the grasper arm 294 is integral to the grasper wire 288. By this it is meant that the grasper arm 294 and the grasper wire 288 can be adjacent portions of a single segment of wire, e.g., a solid, stranded, or braided wire segment from which the grasper wire 288 and the grasper arm 294 have been formed. In such examples the grasper arm 294 extends from the distal end 292 of the grasper wire 288 based on the grasper arm 294 and the grasper wire 288 forming a continuous wire segment through the distal end 292 of the grasper wire 288. Also in some of these embodiments, the only grasper member 246 that the magnet-assisted suture grasper 200 comprises is the grasper arm 294 that is integral to the grasper wire 288, i.e., the magnet-assisted suture grasper 200 comprises only one grasper arm 294 and only one grasper wire 288, and the one grasper arm 294 is integral to the one grasper wire 288.

Alternatively, the grasper arm 294 can be attached to the grasper wire 288 other ways, such as based on direct adhesion or through one, two, or more intermediate parts, such as a ferrule, a ring, or a sleeve, among other intermediate parts. For example, the grasper arm 294 can extend distally from the distal end 292 of the grasper wire 288 based on direct adhesion of the grasper arm 294 to the distal end 292 of the grasper wire 288 or through one, two, or more intermediate parts.

For a grasper arm 294 that is integral to a grasper wire 288, the distal end 292 of the grasper wire 288 is the portion of the grasper wire 288 adjacent the distal hole 228 of the retriever tube 224, and the grasper arm 294 begins and extends distally from this distal end 292 of the grasper wire 288, as shown in FIG. 36 and FIG. 37. For a grasper arm 294 that otherwise extends from the distal end 292 of the grasper wire 288 based on attachment that is direct or indirect, the distal end 292 of the grasper wire 288 is the part of the grasper wire 288 at which the grasper arm 294 is attached.

Also in accordance with these embodiments, the grasper magnet 258 is disposed adjacent the proximal-to-intermediate portion 298 of the grasper arm 294.

The grasper member 246 comprising the grasper wire 288 and the grasper arm 294 can be provided in various configurations.

One exemplary grasper member configuration is a trap wire 304. One example of a trap wire 304 configuration is a loop-style trap wire 304 that comprises a grasper arm loop 306, as shown in FIG. 24, with reference to FIGS. 1-17. In this configuration, the magnet-assisted suture grasper 200 can include a first grasper arm 294 that is integrally attached to a first grasper wire 288 and a second grasper arm 294 that is integrally attached to a second grasper wire 288, with the first and second grasper arms 294 being connected at their distal ends 302, thereby forming the grasper arm loop 306. The first and second grasper arms 294 can comprise an enlarged distal terminus 308 at their distal ends 302.

The trap wire 304 comprising the grasper arm loop 306 is thus formed from two free ends of wire which meet at a single point at the distal end, i.e., first and second grasper arms 294 extending from first and second grasper wires 288, respectively, and connected at their distal ends 302, at which point a large spheroid feature, i.e., an enlarged distal terminus 308, is located.

The enlarged distal terminus 308 is sized to allow contact between the grasper magnet 258 and a suture magnet 502 of a magnetic suture 500 attracted thereto when the grasper arm loop 306 is in the second position 256 outside the needle lumen 216. The enlarged distal terminus 308 also is sized such that when the grasper arm loop 306 is in the first position 254 inside the needle lumen 216, a suture 504 of the magnetic suture 500 can pass by the enlarged distal terminus 308, but the suture magnet 502 of the magnetic suture 500 cannot. For example, for a magnet-assisted suture grasper 200 that includes an extra-thin-wall 17 gauge suture retrieval needle 202, having a nominal inner diameter of 0.050 inches (1.27 mm) and a loop of 3-0 suture 504, having a mean diameter of 0.0079 to 0.0098 inches (0.20 to 0.25 mm), with a magnetic suture ferrule 506 having a major outer diameter of 0.040 inches (1.0 mm), the preferred size for this spheroid member is between 0.016 to 0.040 inches (0.41 to 1.0 mm), nominally. More generally, the enlarged distal terminus 308 can have a size corresponding to about 10% to about 90% of the inner diameter of the needle lumen 216, preferably about 20% to about 80% of the inner diameter of the needle lumen 216, and more preferably about 30% to about 60% of the inner diameter of the needle lumen 216. For example, for an enlarged distal terminus 308 corresponding to a spheroid feature, the enlarged distal terminus 308 can have a diameter of about 10% to about 90%, about 20% to about 80%, or about 30% to about 60% of the inner diameter of the needle lumen 216. Also for example, for an enlarged distal terminus 308 corresponding to an alternative shape, the enlarged distal terminus 308 can have a width transverse to the needle body axis 210 of about 10% to about 90%, about 20% to about 80%, or about 30% to about 60% of the inner diameter of the needle lumen 216. An enlarged distal terminus 308 within this size range will generally be sufficiently small to allow contact between the grasper magnet 258 and a suture magnet 502 of a magnetic suture 500 attracted thereto when the grasper arm loop 306 is outside the needle lumen 216. An enlarged distal terminus 308 within this size range also will generally be sufficiently small to allow a suture 504 of a magnetic suture 500, even a suture 504 having a relatively large mean diameter, to pass by the enlarged distal terminus 308, and sufficiently large to prevent the suture magnet 502 of the magnetic suture 500, even a suture magnet 502 of a relatively small size, from passing by the enlarged distal terminus 308.

Additionally, in this configuration the two strands of wire of the grasper arm loop 306, i.e., the first grasper arm 294 that is integrally attached to the first grasper wire 288 and the second grasper arm 294 that is integrally attached to the second grasper wire 288, flare out before coming back together at the distal ends 302. This flare is sized so that the width measured across the outer diameter of the wires at this point exceeds the inner diameter of the suture retrieval needle 202. For example, for an extra-thin-wall 17 gauge suture retrieval needle 202, the flare is sized so that the width measured across the outer diameter of the wires is greater than 0.050 inches (greater than 1.27 mm). This creates an interference fit between the grasper arm loop 306 and the suture retrieval needle 202, which results in the wires being squeezed together as they are drawn into the needle lumen 216. The elastic deformation of the wires generates a reaction force which pushes back against the inner surface of the needle lumen 216. Because the inner surface of the needle lumen 216 is round, the translation of this force vector by the curved surface acts to push the wires towards the hemisphere of the needle lumen 216, i.e. the wires are disposed across a center line of the distal hole 214 of the needle body 208. This self-centering action helps prevent the spheroid feature from being caught in the crotch of distal hole 214 that is created by the bevel at the sharp tip 218 of the suture retrieval needle 202.

The grasper arm loop 306 can have a length and shape such that the grasper arm loop 306 circumscribes an area sufficiently large to allow contact between the grasper magnet 258 and a suture magnet 502 of a magnetic suture 500 attracted thereto when the grasper arm loop 306 is in the second position 256. For example, the grasper arm loop 306 can have a length and shape such that the corresponding circumscribed area is sufficiently large to fit both the grasper magnet 258 and the suture magnet 502 when the grasper magnet 258 and the suture magnet 502 are in contact at their respective poles.

The grasper arm loop 306 also can be sized such that the grasper arm loop 306 has a thickness, e.g., a mean diameter, sufficiently great to block the suture magnet 502 of the magnetic suture 500 from exiting the needle lumen 216 through the distal hole 214 of the suture retrieval needle 202 when the grasper arm loop 306 is in the first position 254. The grasper arm loop 306 can be thinner than the enlarged distal terminus 308 and still block a suture magnet 502 from exiting a needle lumen 216 based on the grasper arm loop 306 being disposed across a center line of the distal hole 214 of the needle body 208 due to an interference fit between the grasper arm loop 306 and the suture retrieval needle 202 as discussed above. Suitable thicknesses, e.g., mean diameters, for the grasper arm loop 306 otherwise can be determined similarly as for the enlarged distal terminus 308. For example, for a magnet-assisted suture grasper 200 that includes an extra-thin-wall 17 gauge suture retrieval needle 202, having a nominal inner diameter of 0.050 inches (1.27 mm) and a loop of 3-0 suture 504, having a mean diameter of 0.0079 to 0.0098 inches (0.20 to 0.25 mm), with a magnetic suture ferrule 506 having a major outer diameter of 0.040 inches (1.0 mm), the preferred mean diameter for the wire is about 0.0060 inches (0.15 mm). More generally, the grasper arm loop 306 can have a mean diameter, for example, corresponding to about 0.5% to about 10% of the inner diameter of the needle lumen 216, preferably about 2% to about 4% of the inner diameter of the needle lumen 216, and more preferably about 2.3% to about 3.5% of the inner diameter of the needle lumen 216. A grasper arm loop 306 within this size range generally will have a thickness, e.g., a mean diameter, sufficiently great to block a suture magnet 502 of a magnetic suture 500 from exiting the needle lumen 216 through the distal hole 214 of the suture retrieval needle 202 when the grasper arm loop 306 is in the first position 254.

The preferred material for the first grasper arm 294 that is integrally attached to the first grasper wire 288 and the second grasper arm 294 that is integrally attached to the second grasper wire 288 is Nitinol. This is due to the pseudo-elastic nature of Nitinol, which allows wires made from Nitinol to recover their shape after relatively large deformations. The preferred method of manufacture is to hold the two corresponding strands of wire together with the distal ends 302 of their corresponding grasper arms 294 aligned flush, and apply sufficient energy to melt the distal ends 302. The resulting molten metal at the distal ends 302 thereby pools together, and surface tension pulls the liquid metal into a spheroidal shape. As the metal cools, this shape is naturally maintained, resulting in an autogenous weld between the two strands of wire that is terminated by a spheroidal member.

The trap wire 304 serves as a mechanical plug, creating a blockage within the needle lumen 216 by which the suture magnet 502 of the magnetic suture 500 cannot pass. This can be accomplished various additional trap wire 304 configurations too. For example, rather than comprising a grasper arm loop 306, the trap wire 304 can be a single-wire-style trap wire 304 that comprises a single grasper arm 294 that is integrally attached to a single grasper wire 288. This is shown in FIGS. 84-87. The single grasper arm 294 can comprise an enlarged distal terminus 308 at its distal end 302. In some examples, the integral grasper wire 288 and grasper arm 294 can be a Nitinol wire having a mean diameter of about 0.0080 inches (0.20 mm). This provides an advantage of being simpler to manufacture than a grasper arm loop 306. This also provides an advantage of improved flow properties through the retriever tube lumen 230 due to the presence of only one grasper wire 288 being disposed in the retriever tube lumen 230 instead of two grasper wires 288 being disposed there. Alternatively, more than two grasper arms 294 could be employed. This provides an advantage that multiple grasper arms 294 of a smaller cross-section could be employed to obtain an equivalent strength to a single grasper arm 294 of a larger cross-section, but the multiple grasper arms 294 would not intrude as far into the needle lumen 216, allowing for maximization of the diameter of the grasper magnet 258. A similar effect could be achieved by using a grasper arm 294 with a non-round profile for the grasper arm 294. Also alternatively, the plug element does not need to be melt-formed. A separate component may be attached, such as by swaging, or by employing an adhesive. The plug element also does not need to be spheroid, as its shape is not critical to its function. Thus the plug element alternatively could be shaped as, for example, an elongated cylinder, or a pyramid, or a toroid. Also alternatively, the grasper arm 294 could simply terminate in a pig-tailed coil, forming a basket-like shape.

Accordingly, in some of these embodiments, the grasper member 246 further comprises an enlarged distal terminus 308 at the distal end 302 of the grasper arm 294. In these embodiments, the grasper arm 294 is reversibly moveable between the first position 254 and the second position 256 based on translation of the grasper arm 294 from inside of the needle lumen 216 to outside of the needle lumen 216 through the distal hole 214 of the needle body 208. In these embodiments, the enlarged distal terminus 308 has a size sufficiently small to allow contact between the grasper magnet 258 and a suture magnet 502 of a magnetic suture 500 attracted thereto when the grasper arm 294 is in the second position 256 and to allow a suture 504 of the magnetic suture 500 to pass when the grasper arm 294 is in the first position 254. Also, the enlarged distal terminus 308 has a size sufficiently large to block the suture magnet 502 of the magnetic suture 500 from exiting the needle lumen 216 through the distal hole 214 of the needle body 208 when the grasper arm 294 is in the first position 254. In these embodiments, the enlarged distal terminus 308 prevents the magnetic suture 500 from being pulled out of the needle lumen 216. Accordingly, such a grasper arm 294 only needs to be advanced so far as to free the enlarged distal terminus 308 from the constraint of the suture retrieval needle 202. If a force is then applied to the magnetic suture 500, and if the magnetic suture 500 includes a magnetic-suture ferrule 506 that is tapered, then the enlarged distal terminus 308 will ride up the tapered magnetic-suture ferrule 506, which will deflect the grasper arm 294 away from the tapered magnetic-suture ferrule 506, and allow the magnetic suture 500 to pass from the needle lumen 216. This can be advantageous for suturing at sites within a patient in which space is limited, since it is not necessary for the entire grasper arm 294 to travel beyond the distal end 206 of the suture retrieval needle 202 in order to release the magnetic suture 500. In some examples of these embodiments, the size of the enlarged distal terminus 308 is about 10% to about 90%, preferably about 20% to about 80%, more preferably about 30% to about 60% of the inner diameter of the needle lumen 216. For example, the enlarged distal terminus 308 can have a diameter that is about 10% to about 90%, preferably about 20% to about 80%, more preferably about 30% to about 60% of the inner diameter of the needle lumen 216.

Also in some embodiments, the grasper member 246 is a first grasper member 246, the grasper wire 288 is a first grasper wire 288, and the grasper arm 294 is a first grasper arm 294. In these embodiments, the magnet-assisted suture grasper 200 further comprises a second grasper member 246 comprising: (a) a second grasper wire 288 having a proximal end 290 and a distal end 292, being fixedly disposed within the retriever tube 224, and extending distally therefrom, and (b) a second grasper arm 294 comprising a proximal end 296, a proximal-to-intermediate portion 298, a distal portion 300, and a distal end 302, the second grasper arm 294 extending from the distal end 292 of the second grasper wire 288 and being reversibly moveable between the first position 254 and the second position 256. In these embodiments, the first and second grasper arms 294 are connected at their distal ends 302, thereby forming a grasper arm loop 306. Also, the first and second grasper members 246 further comprise an enlarged distal terminus 308 at the distal ends 302 of the first and second grasper arms 294. The grasper arm loop 306 is reversibly moveable between the first position 254 and the second position 256 based on translation of the grasper arm loop 306 from inside of the needle lumen 216 to outside of the needle lumen 216 through the distal hole 214 of the needle body 208. The grasper arm loop 306 circumscribes an area sufficiently large, and the enlarged distal terminus 308 has a size sufficiently small, to allow contact between the grasper magnet 258 and a suture magnet 502 of a magnetic suture 500 attracted thereto when the grasper arm loop 306 is in the second position 256. The enlarged distal terminus 308 has a size sufficiently small to allow a suture 504 of the magnetic suture 500 to pass when the grasper arm loop 306 is in the first position 254. The enlarged distal terminus 308 has a size sufficiently large to block the suture magnet 502 of the magnetic suture 500 from exiting the needle lumen 216 through the distal hole 214 of the needle body 208 when the grasper arm loop 306 is in the first position 254. These embodiments are advantageous for allowing use of grasper arms 294 having relatively smaller diameters. In some examples of these embodiments, the size of the enlarged distal terminus 308 is about 10% to about 90%, preferably about 20% to about 80%, more preferably about 30% to about 60% of the inner diameter of the needle lumen 216. For example, the enlarged distal terminus 308 can have a diameter that is about 10% to about 90%, preferably about 20% to about 80%, more preferably about 30% to about 60% of the inner diameter of the needle lumen 216. Also in some of these embodiments the mean diameter of the grasper arm loop 306 is about 0.5% to about 10%, preferably about 2% to about 4%, more preferably about 2.3% to about 3.5% of the inner diameter of the needle lumen 216.

Figure 94:
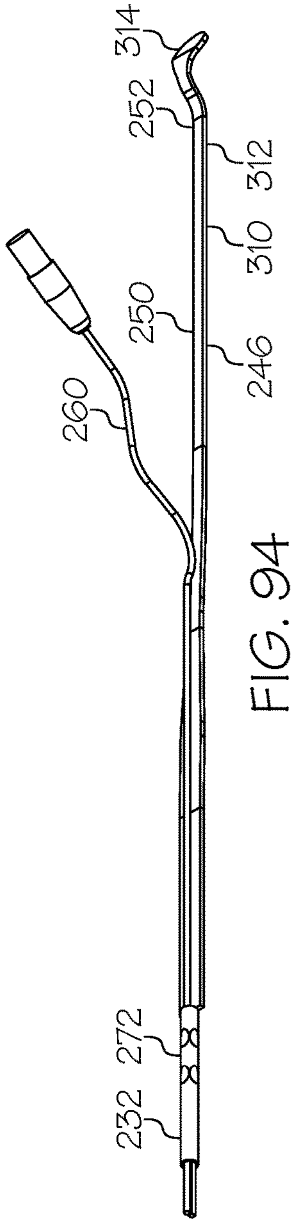
FIG. 94 is a perspective view of an alternative embodiment of the grasper member of FIG. 1, in which the grasper member is a flat-wire grasper member having an angled distal terminus, and the grasper ferrule, the grasper magnet, and the magnet wire of the magnet-assisted suture grasper of FIG. 1. As shown, the grasper ferrule has been crimped onto the grasper member and the magnet wire.
Figure 102:
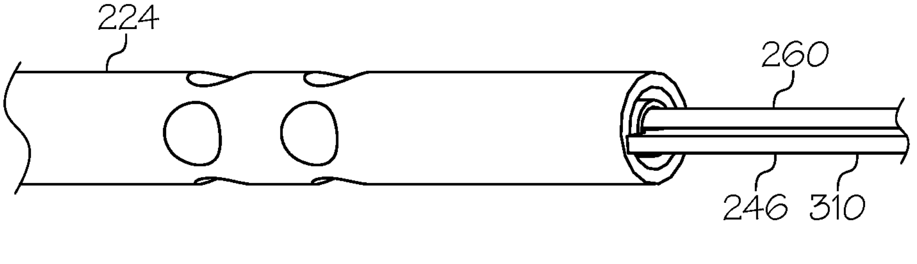
FIG. 102 is a perspective view of the flat-wire grasper member having an angled distal terminus of FIG. 94 and the retriever tube, the grasper ferrule, and the magnet wire of the magnet-assisted suture grasper of FIG. 1, during assembly. The retriever tube has been crimped onto the grasper ferrule.
Figure 103:
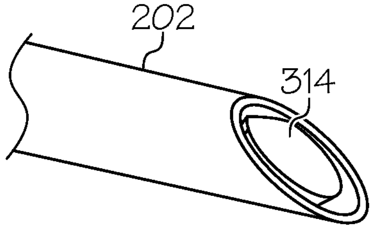
FIG. 103 is a perspective view of the flat-wire grasper member having an angled distal terminus of FIG. 94 and a distal portion of the suture retrieval needle of the magnet-assisted suture grasper of FIG. 1. The flat-wire grasper member is in the first position.
Figure 104:
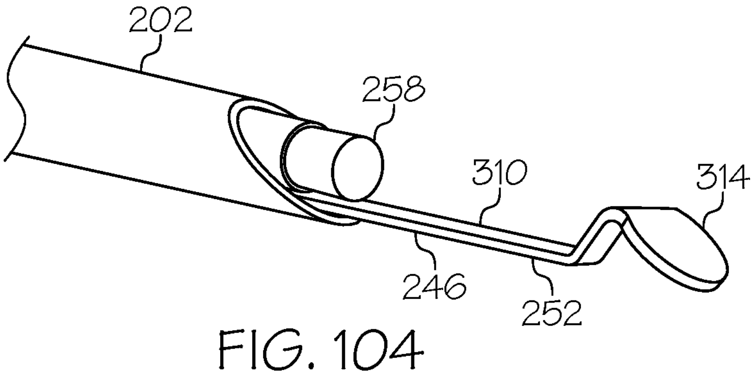
FIG. 104 is a perspective view of the flat-wire grasper member having an angled distal terminus of FIG. 94 and the suture retrieval needle and the grasper magnet of the magnet-assisted suture grasper of FIG. 1. The flat-wire grasper member is in a position between the first position and the second position.
Figure 105:
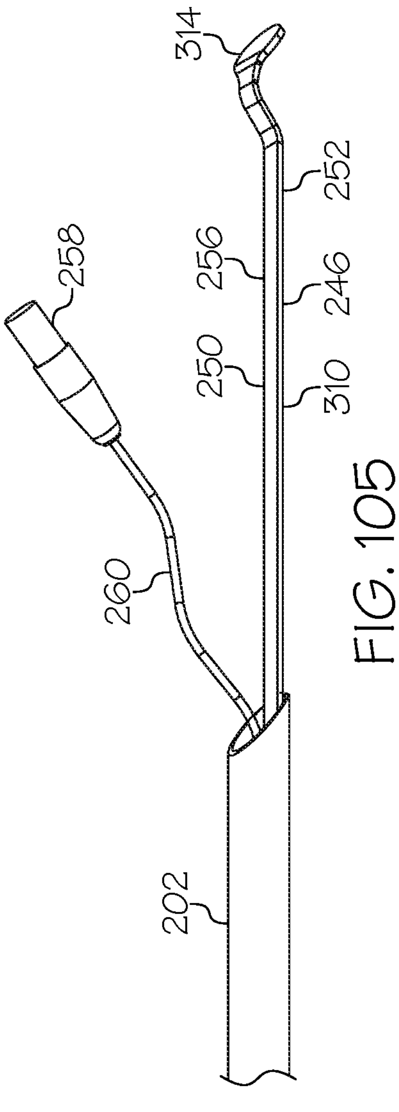
FIG. 105 is a perspective view of the flat-wire grasper member having an angled distal terminus of FIG. 94 and the suture retrieval needle and the grasper magnet of the magnet-assisted suture grasper of FIG. 1. The flat-wire grasper member is in the second position.
Figure 106:
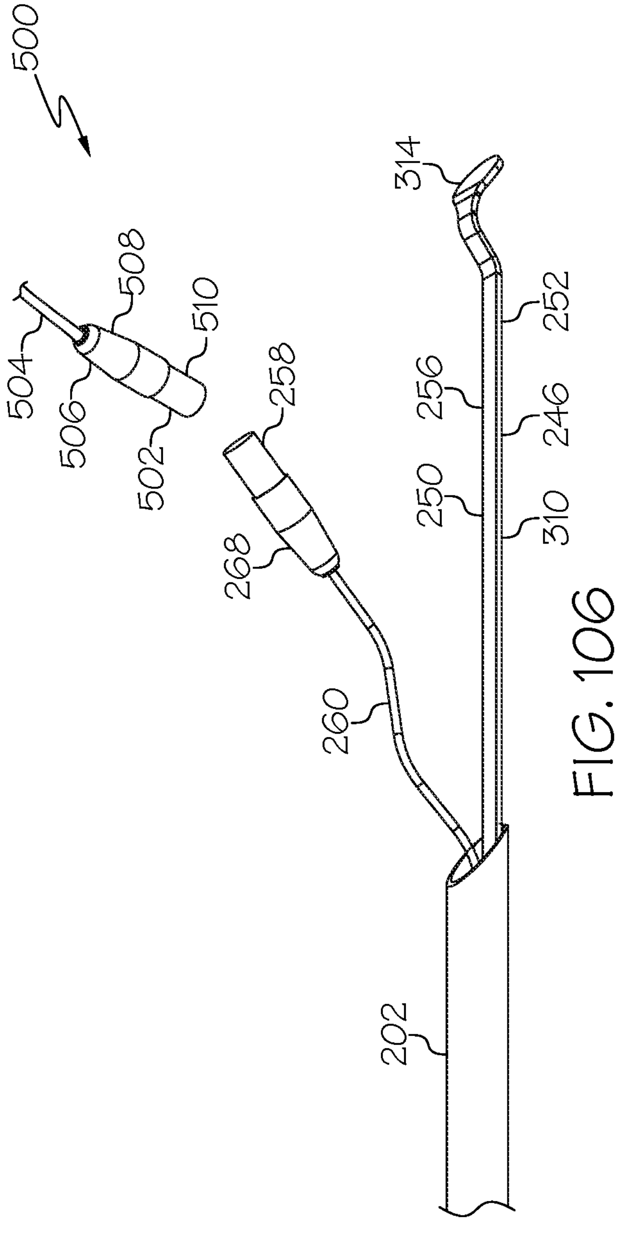
FIG. 106 is a perspective view of the flat-wire grasper member having an angled distal terminus of FIG. 94 and the suture retrieval needle and the grasper magnet of the magnet-assisted suture grasper of FIG. 1. The grasper magnet is attracting a magnetic suture.
Figure 107:
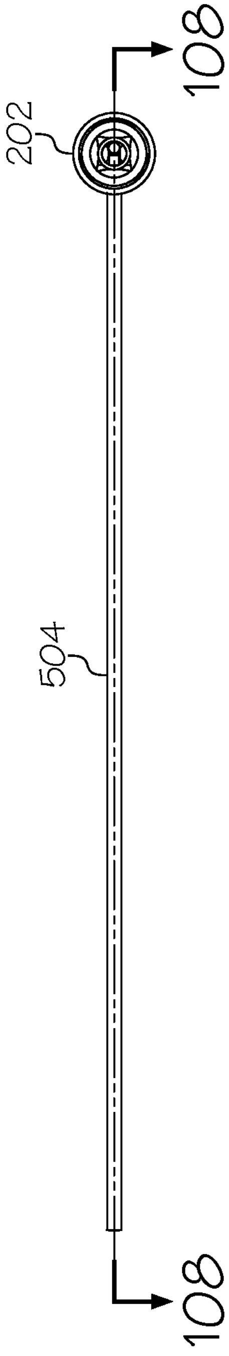
FIG. 107 is a front view of the flat-wire grasper member having an angled distal terminus of FIG. 94, the suture retrieval needle and the grasper magnet of the magnet-assisted suture grasper of FIG. 1, and a magnetic suture.
Figure 108:
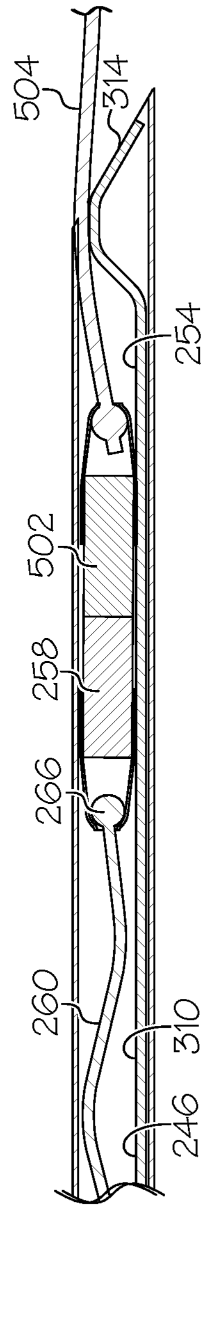
FIG. 108 is a side sectional view of the flat-wire grasper member having an angled distal terminus of FIG. 94, the suture retrieval needle and the grasper magnet of the magnet-assisted suture grasper of FIG. 1, and a magnetic suture, viewed along the cutting plane shown in FIG. 107. The advancer assembly is in a locked retracted position sequestering the grasper magnet within the suture retrieval needle, and the grasper magnet is attracting a magnetic suture and in contact with the magnetic suture, such that the magnetic suture has been captured within the needle lumen of the suture retrieval needle of the magnet-assisted suture grasper.
Figure 109:
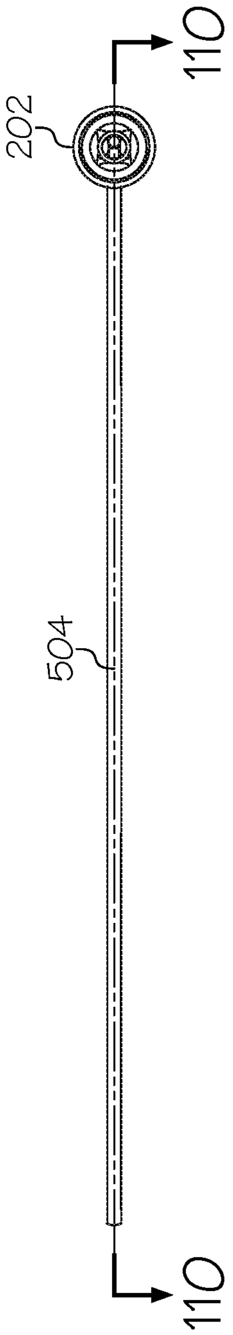
FIG. 109 is a front view of the flat-wire grasper member having an angled distal terminus of FIG. 94, the suture retrieval needle and the grasper magnet of the magnet-assisted suture grasper of FIG. 1, and a magnetic suture.
Figure 110:
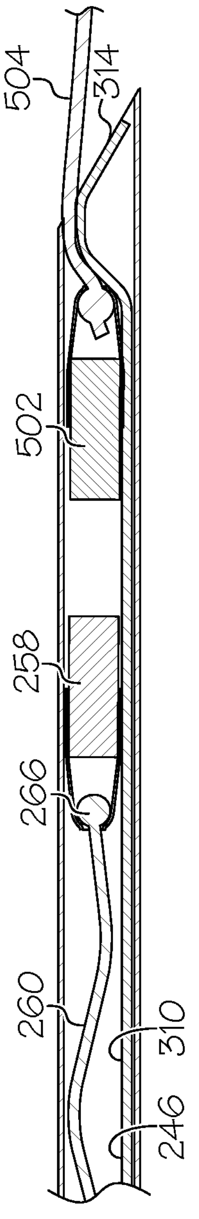
FIG. 110 is a side sectional view of the flat-wire grasper member having an angled distal terminus of FIG. 94, the suture retrieval needle and the grasper magnet of the magnet-assisted suture grasper of FIG. 1, and a magnetic suture, viewed along the cutting plane shown in FIG. 109. The advancer assembly is in a locked retracted position. The angled distal terminus of the flat-wire grasper member is grasping the magnetic suture, such that the magnetic suture remains captured within the needle lumen of the suture retrieval needle of the magnet-assisted suture grasper.
Figure 111:
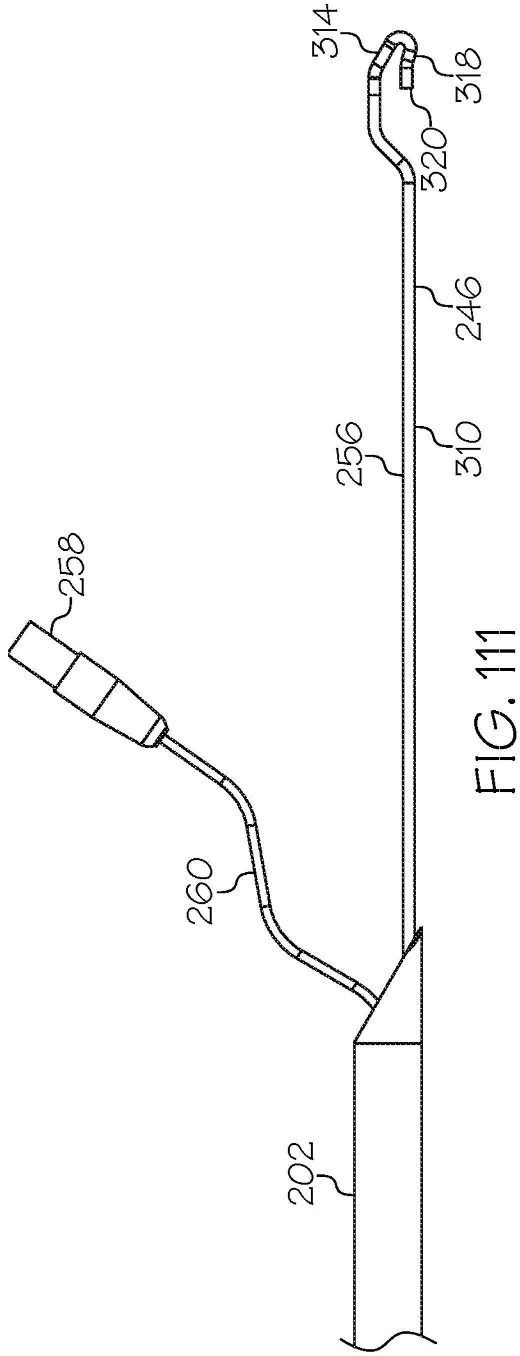
FIG. 111 is a side view of a first alternative embodiment of a flat-wire grasper member having an angled distal terminus including a hook and the suture retrieval needle, the grasper magnet, and the magnet wire of the magnet-assisted suture grasper of FIG. 1. The flat-wire grasper member is in the second position.
Figure 112:
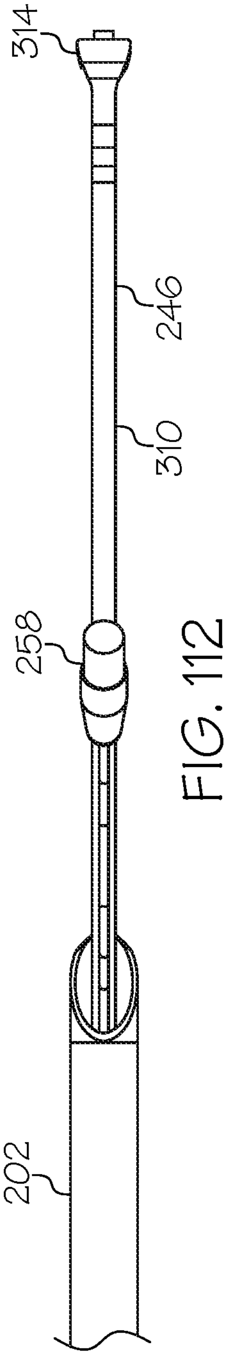
FIG. 112 is a top view of the first alternative embodiment of the flat-wire grasper member having an angled distal terminus including a hook, the suture retrieval needle, the grasper magnet, and the magnet wire of FIG. 111.
Figure 113:
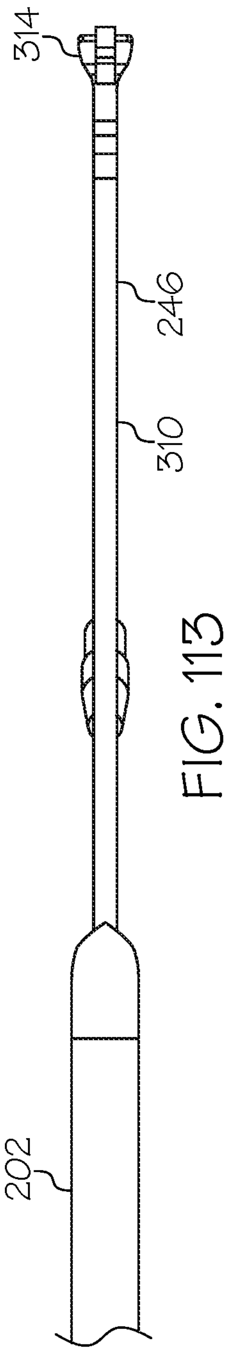
FIG. 113 is a bottom view of the first alternative embodiment of the flat-wire grasper member having an angled distal terminus including a hook, the suture retrieval needle, the grasper magnet, and the magnet wire of FIG. 111.
Figure 114:
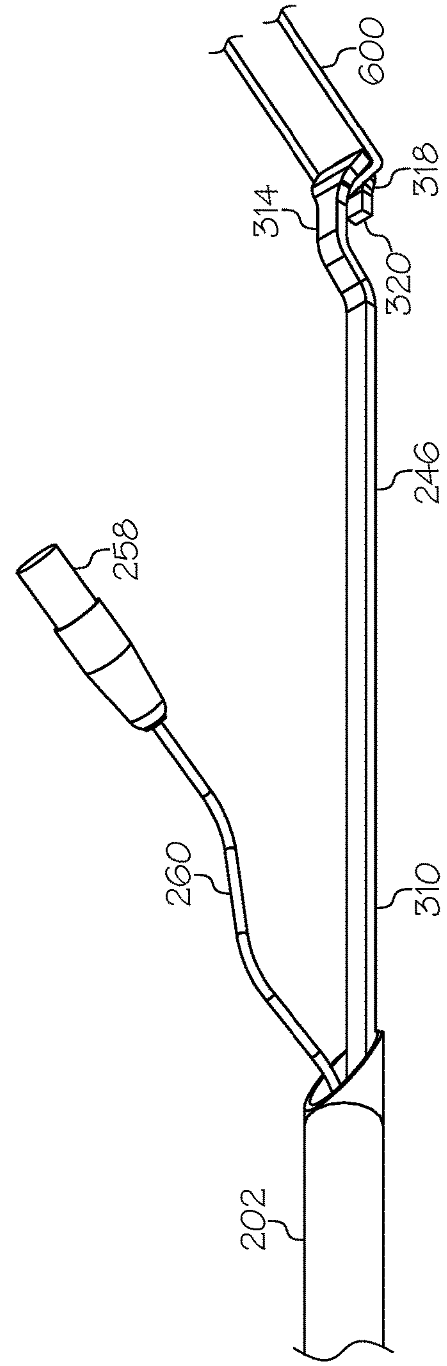
FIG. 114 is a perspective view of the first alternative embodiment of the flat-wire grasper member having an angled distal terminus including a hook, the suture retrieval needle, the grasper magnet, and the magnet wire of FIG. 111, in which a suture has been captured on the hook of the flat-wire grasper member.
Figure 115:
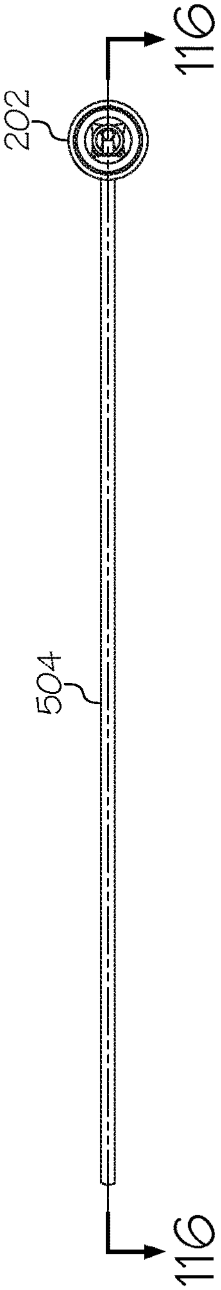
FIG. 115 is a front view of a first alternative embodiment of a flat-wire grasper member having an angled distal terminus including a hook and the suture retrieval needle, the grasper magnet, and the magnet wire of the magnet-assisted suture grasper of FIG. 1, and a magnetic suture. The flat-wire grasper member is in the first position.
Figure 116:
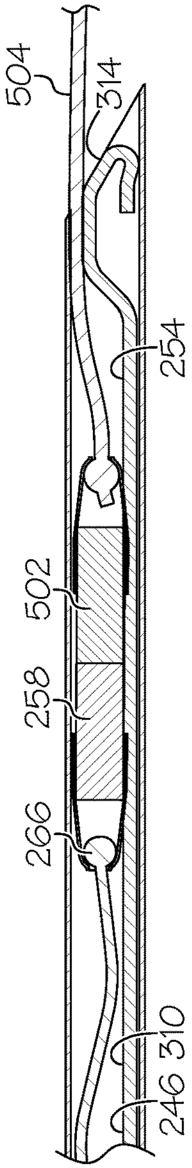
FIG. 116 is a side sectional view of the first alternative embodiment of the flat-wire grasper member having an angled distal terminus including a hook, the suture retrieval needle, the grasper magnet, and the magnet wire of FIG. 115, and a magnetic suture, viewed along the cutting plane shown in FIG. 115. The grasper magnet is attracting a magnetic suture and in contact with the magnetic suture, such that the magnetic suture has been captured within the needle lumen of the suture retrieval needle of the magnet-assisted suture grasper.
Figure 117:
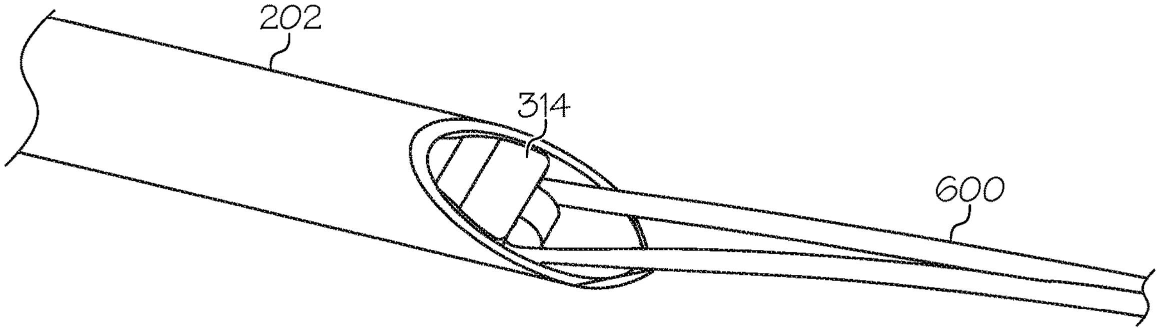
FIG. 117 is a perspective view of the first alternative embodiment of a flat-wire grasper member having an angled distal terminus including a hook and the suture retrieval needle, the grasper magnet, and the magnet wire of the magnet-assisted suture grasper of FIG. 1. The flat-wire grasper member is in the first position. A suture has been captured on the hook.
Figure 118:
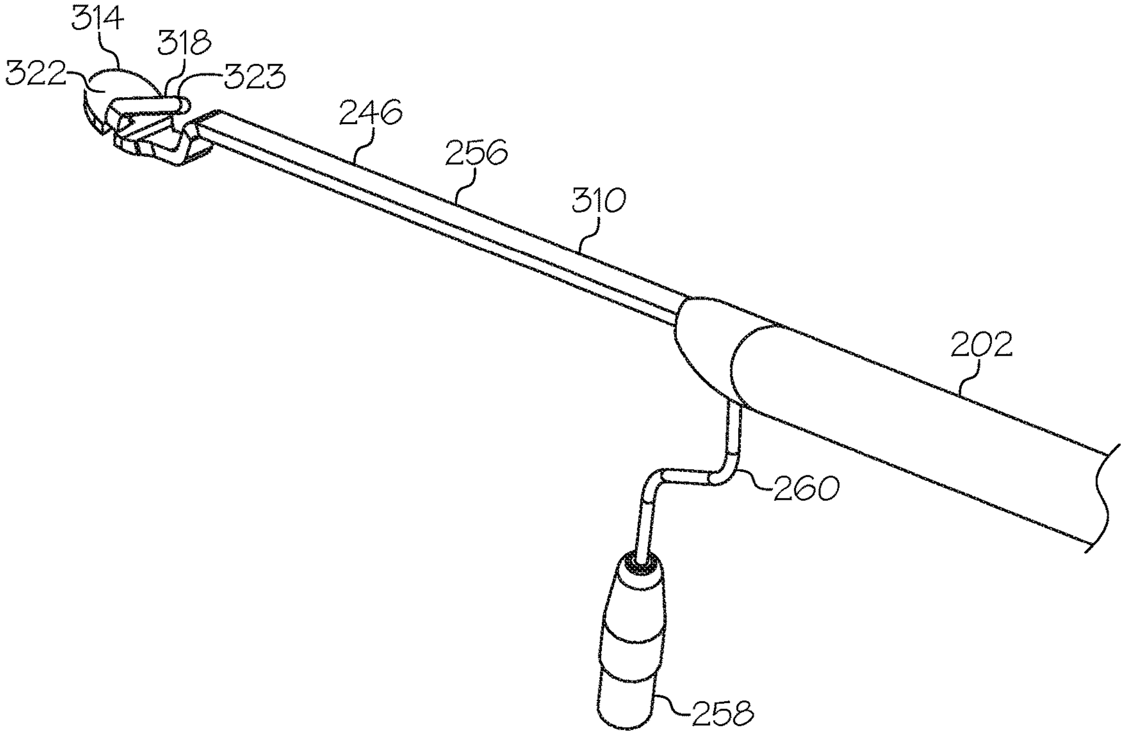
FIG. 118 is a perspective view of a second alternative embodiment of the flat-wire grasper member having an angled distal terminus including a hook and the suture retrieval needle, the grasper magnet, and the magnet wire of the magnet-assisted suture grasper of FIG. 1. The flat-wire grasper member is in the second position.
Figure 119:
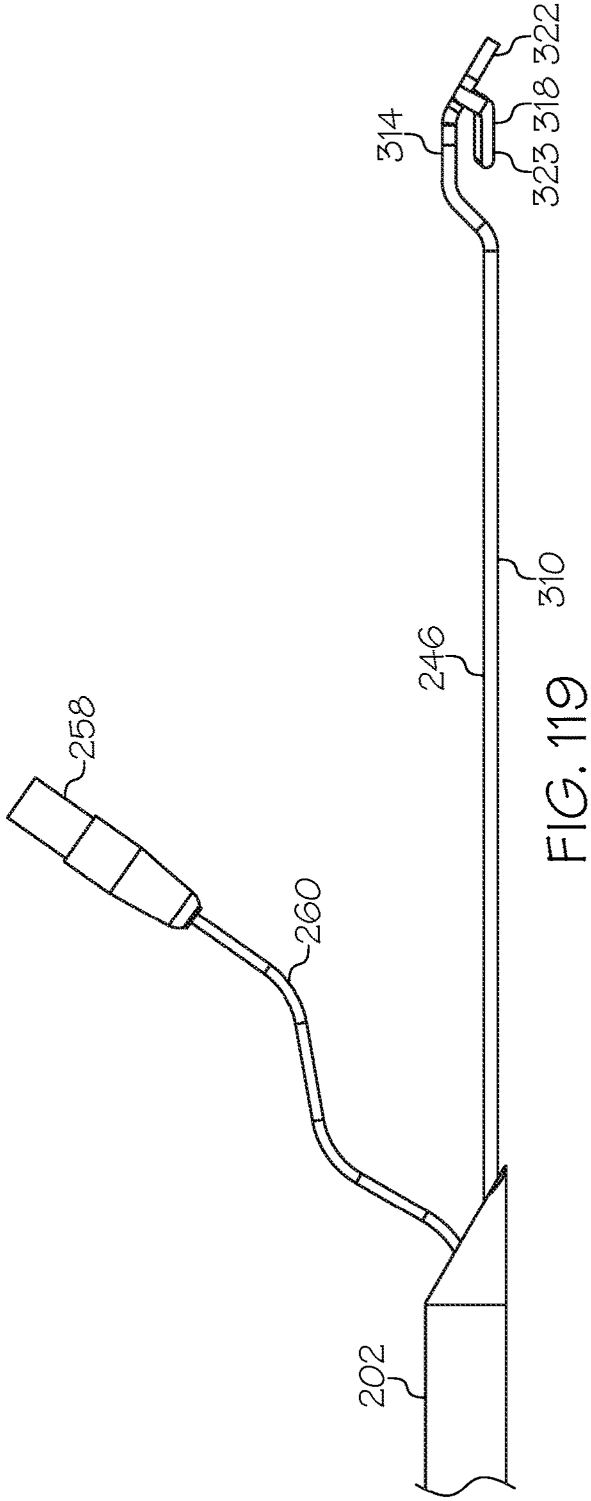
Figure 120:
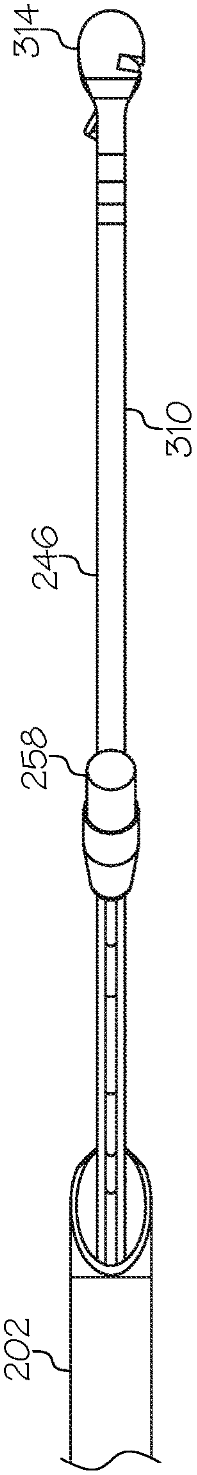
Figure 121:
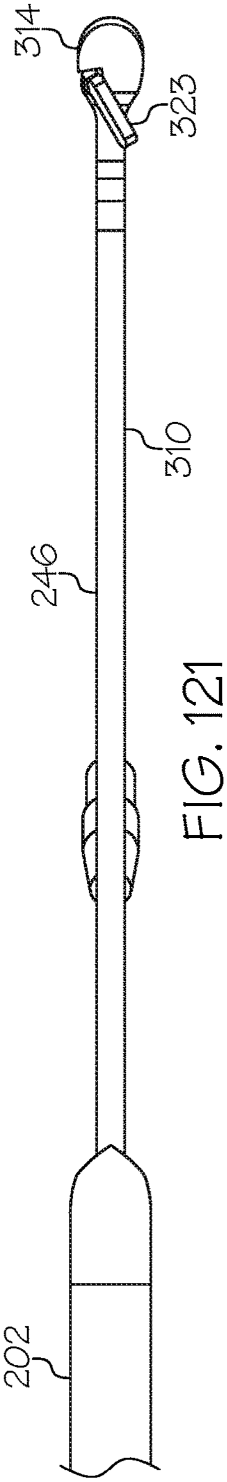
Figure 122:
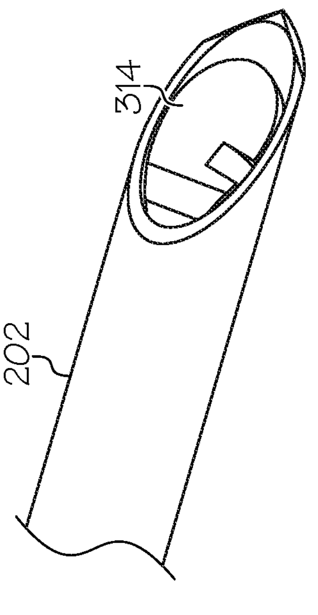
Figure 123:
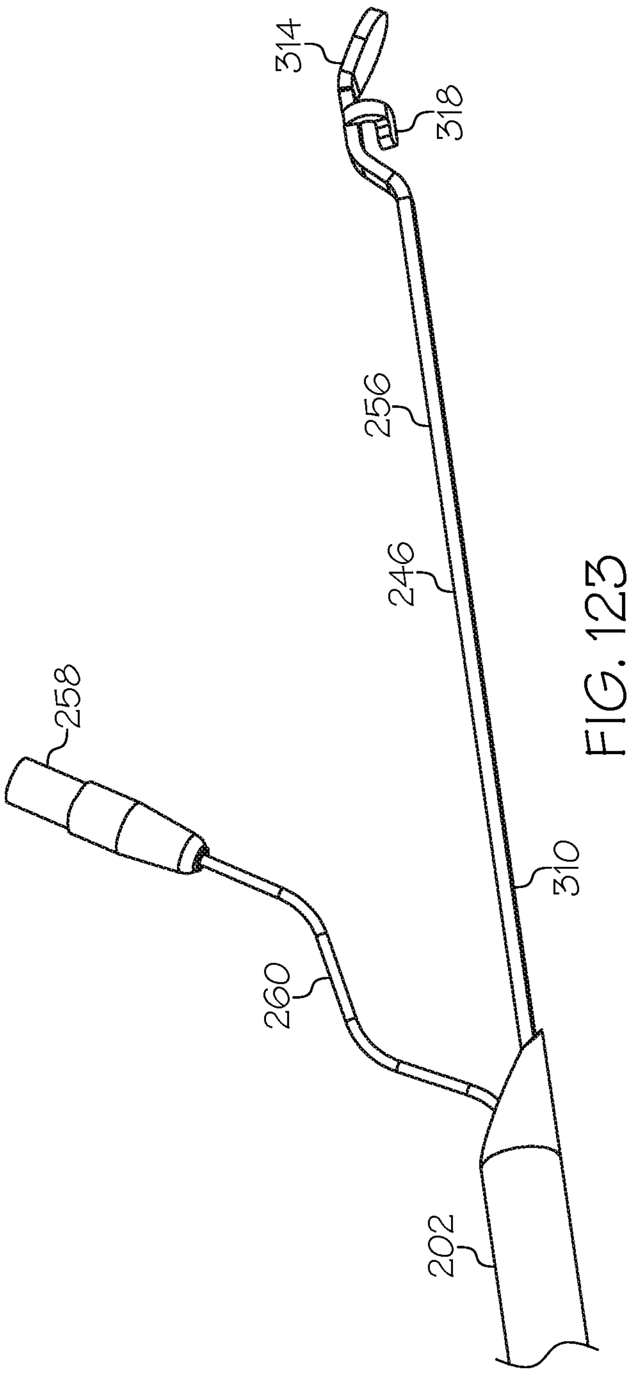
Figure 124:
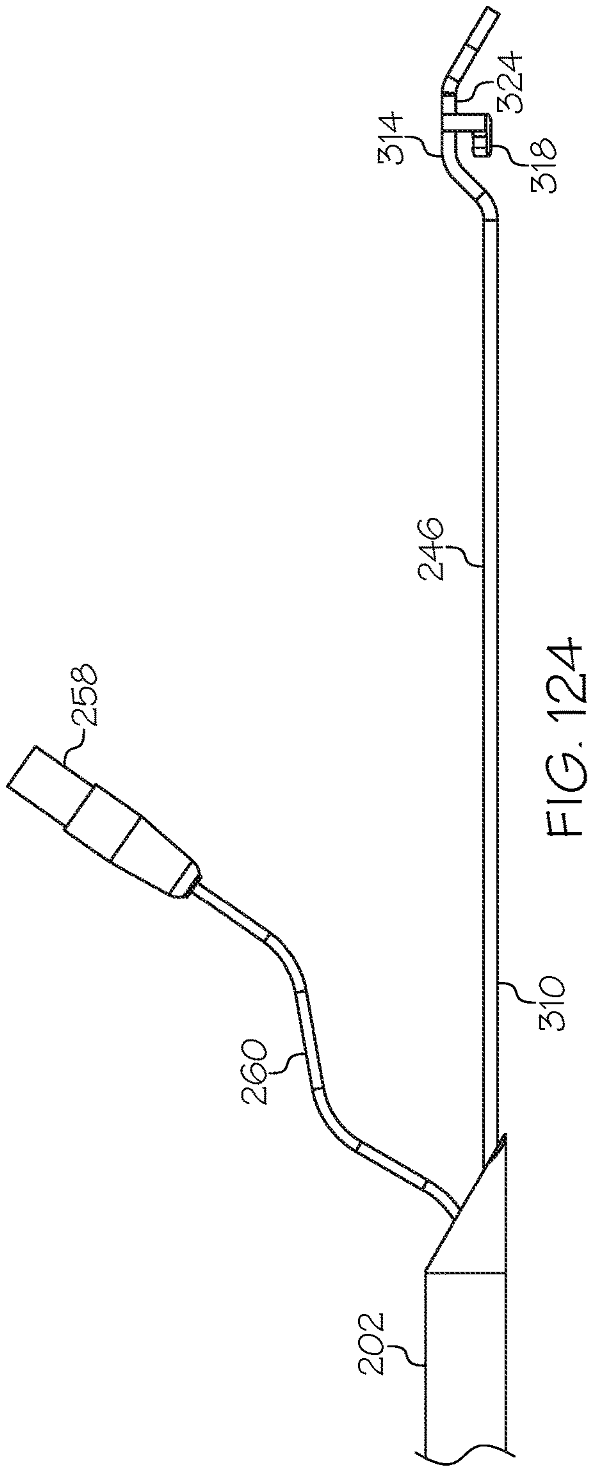
Figure 125:
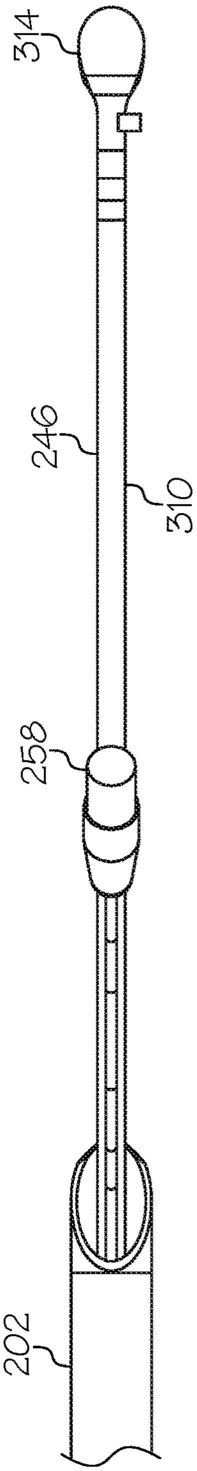
Figure 126:
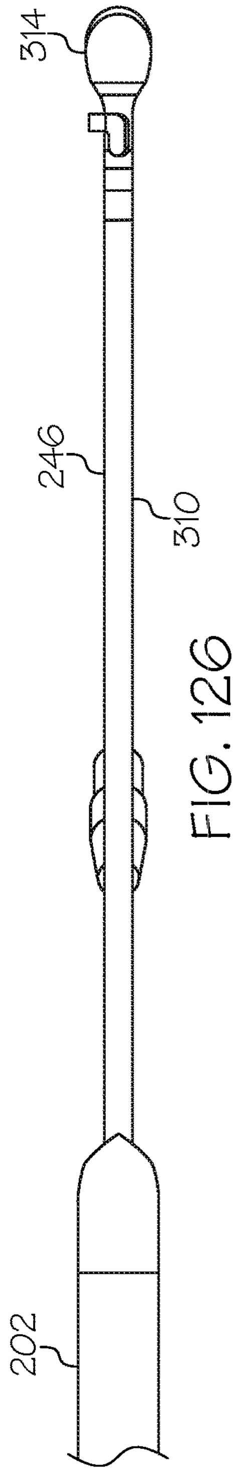
Figure 127:
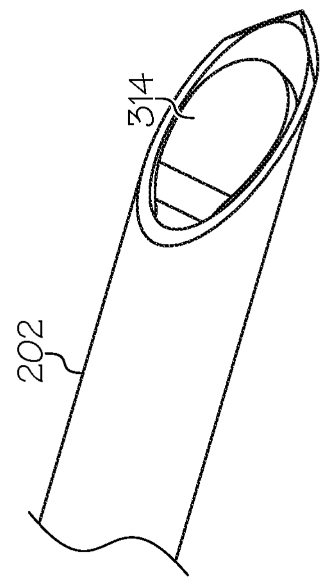

As shown in FIGS. 94-110, another exemplary grasper member configuration is a flat-wire grasper member 310. As shown in FIG. 94, in this configuration, the magnet-assisted suture grasper 200 can include a grasper member 246 that is formed from a flat wire 312 having a rectangular cross-section. The grasper arm 294 of the flat wire 312 is folded at its distal end to form an angled distal terminus 314. As shown in FIG. 103 and FIG. 108, the angled distal terminus 314 is shaped to occlude the needle lumen 216 of the suture retrieval needle 202. As shown in FIG. 110, this blocks the suture magnet 502 of a magnetic suture 500 from exiting the needle lumen 216 when the grasper arm 294 is in the first position 254.

The angled distal terminus 314 of the grasper arm 294 of the flat-wire grasper member 310 may be shaped to fit the distal hole 214 of the needle body 208 of the suture retrieval needle 202. This can be advantageous by helping to prevent coring of soft tissue during needle passage. This is analogous in purpose to stylets that are included in spinal needles.

The flat-wire grasper member 310 provides advantages including low manufacturing cost, an ability to incorporate advanced shapes and datum features to with assembly, an ability to tune stiffness of the grasper member 246 anisotropically through independent adjustment of the width and thickness dimensions of the grasper member 246, and an ability to further tune stiffness by incorporating geometries such as dimples and/or creases.

A flat-wire grasper member 310 may be formed by various precision metal cutting processes, such as such as laser cutting, electro-discharge machining, micro-waterjet cutting, or die cutting, or metal forming processes, such as bending, die stamping, or coining.

Figure 99:
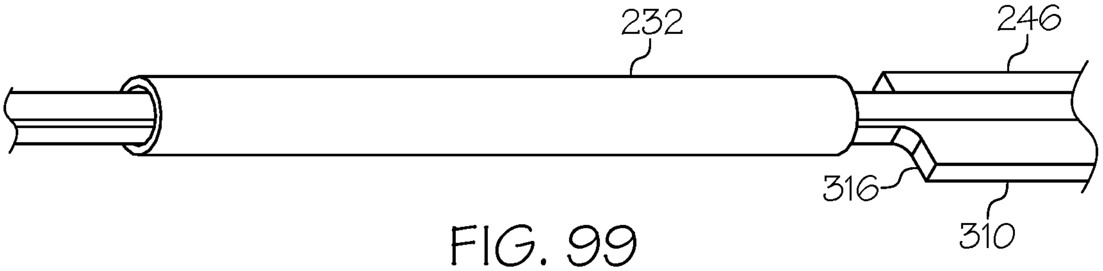
FIG. 99 is a perspective view the flat-wire grasper member having an angled distal terminus of FIG. 94 and the grasper ferrule and the magnet wire of the magnet-assisted suture grasper of FIG. 1, during assembly.
Figure 100:
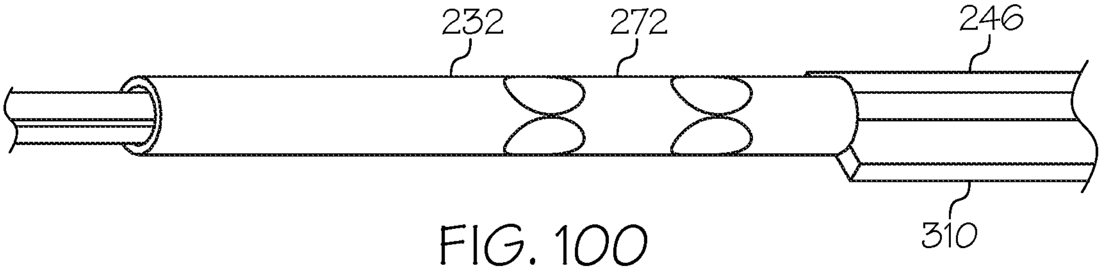
FIG. 100 is a perspective view of the flat-wire grasper member having an angled distal terminus of FIG. 94 and the grasper ferrule and the magnet wire of the magnet-assisted suture grasper of FIG. 1. The grasper ferrule has been crimped onto the flat-wire grasper member and the magnet wire.
Figure 101:
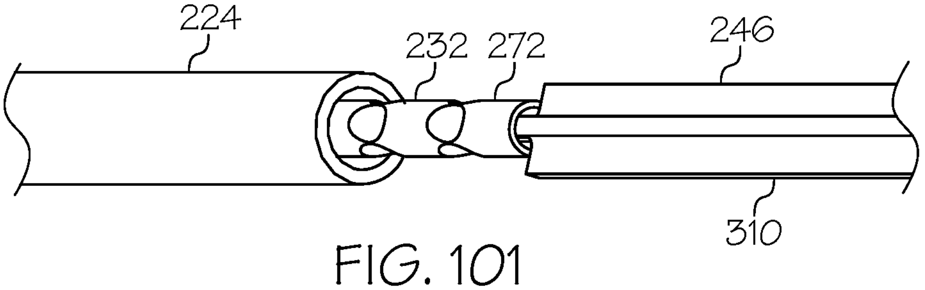
FIG. 101 is a perspective view of the flat-wire grasper member having an angled distal terminus of FIG. 94 and the retriever tube, the grasper ferrule, and the magnet wire of the magnet-assisted suture grasper of FIG. 1, during assembly.

With reference to FIGS. 95-100, assembly of a grasper ferrule subassembly 270 including the flat-wire grasper member 310 can be accomplished by use of a grasper ferrule 232 as described above. With reference to FIG. 101 and FIG. 102, the resulting grasper ferrule subassembly 270 can be joined to the retriever tube 224 also as described above.

Figure 95:
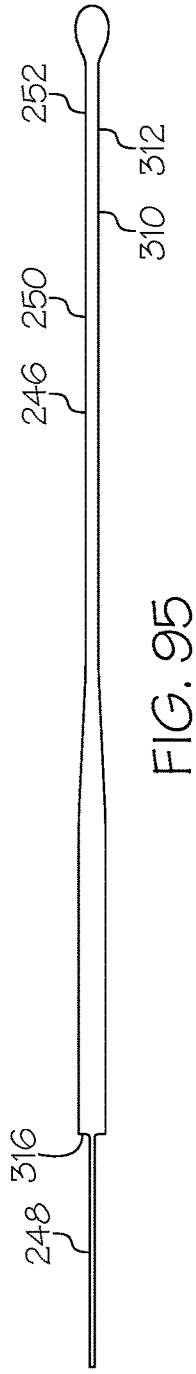
FIG. 95 is a top view of a flat-wire grasper member having a flat distal terminus.
Figure 96:
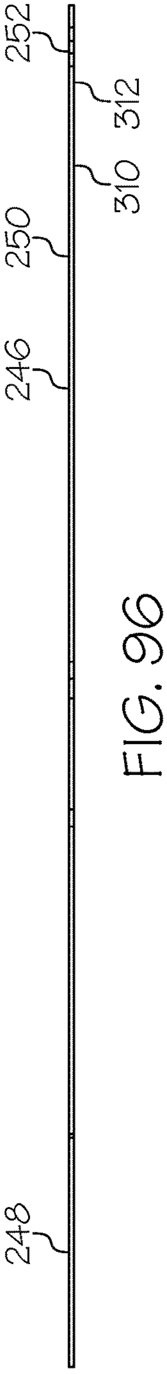
FIG. 96 is a side view of the flat-wire grasper member of FIG. 95.
Figure 97:
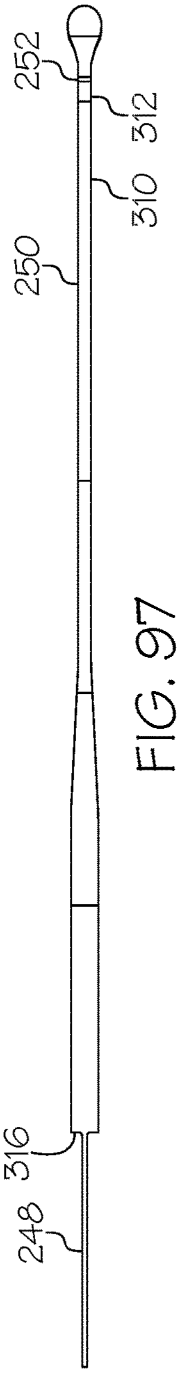
FIG. 97 is a top view of the flat-wire grasper member having an angled distal terminus of FIG. 94.
Figure 98:
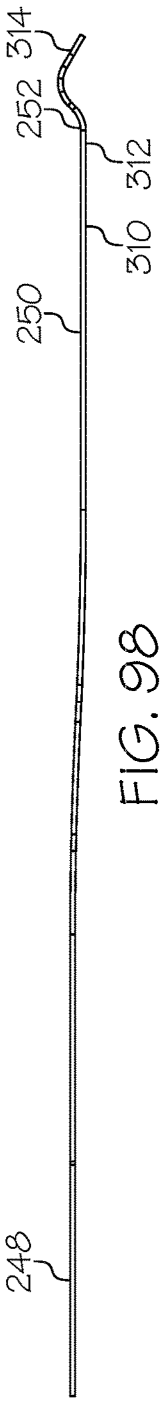
FIG. 98 is a side view of the flat-wire grasper member of FIG. 97.

A profile cutting process provides added design flexibility, allowing datum features to be formed on the flat-wire grasper member 310 that simplify assembly. For example, a locating feature can be added to aid with assembly. The locating feature can be, for example, a depth stop 316 for the retriever tube 224, as shown in FIG. 95, FIG. 99, and FIG. 100, which helps to reduce variance in the assembled length dimensions.

As shown in FIGS. 111-132, the angled distal terminus 314 of the grasper arm 294 of the flat-wire grasper member 310 can be modified to include a hook 318.

For example, as shown in FIGS. 111-117, the angled distal terminus 314 can have a distal end 320 that is formed as a hook 318. This can be advantageous for allowing the magnet-assisted suture grasper 200 to be used for medially grabbing a non-magnetic suture 600. This expands usefulness of the magnet-assisted suture grasper 200, allowing it to be used also in procedures involving non-magnetic sutures 600.

Also for example, as shown in FIGS. 118-122, the angled distal terminus 314 can comprise a distal face 322, and the hook 318 can be formed by folding a portion 323 of the angled distal terminus 314 proximally at the distal face 322. The resulting angled distal terminus 314 retains more planar surface that acts to fill the distal hole 214 of the needle body 208 of the suture retrieval needle 202. This can be advantageous by allowing the angled distal terminus 314 to fill a greater percentage of the distal hole 214 of the needle body 208, thereby retaining more anti-coring benefit.

Also for example, as shown in FIGS. 123-127, the angled distal terminus 314 can comprise a lower face 324, and the hook 318 can extend from the lower face 324. The resulting angled distal terminus 314 retains even more planar surface, thus allowing the angled distal terminus 314 to fill an even greater percentage of the distal hole 214 of the needle body 208, thereby retaining even more anti-coring benefit.

Also for example, as shown in FIGS. 128-132, the flat-wire grasper member 310 can be folded to form a hook 318 proximal to the angled distal terminus 314. The resulting angled distal terminus 314 similarly retains even more planar surface, thereby retaining even more anti-coring benefit.

Accordingly, in some of these embodiments, the grasper arm 294 is formed from a flat wire 312 having a rectangular cross-section. In these embodiments, the grasper member 246 further comprises an angled distal terminus 314 at the distal end 302 of the grasper arm 294. In these embodiments, the grasper arm 294 is reversibly moveable between the first position 254 and the second position 256 based on translation of the grasper arm 294 from inside of the needle lumen 216 to outside of the needle lumen 216 through the distal hole 214 of the needle body 208. The angled distal terminus 314 has a size sufficiently small to allow contact between the grasper magnet 258 and a suture magnet 502 of a magnetic suture 500 attracted thereto when the grasper arm 294 is in the second position 256 and to allow a suture 504 of the magnetic suture 500 to pass when the grasper arm 294 is in the first position 254, and sufficiently large to block the suture magnet 502 of the magnetic suture 500 from exiting the needle lumen 216 through the distal hole 214 of the needle body 208 when the grasper arm 294 is in the first position 254.

In some examples of these embodiments, the angled distal terminus 314 comprises a hook 318.

Also in some examples of these embodiments, the angled distal terminus 314 fills 80% or more of an area of the distal hole 214 of the needle body 208 when the grasper arm 294 is in the first position 254, e.g., 85%, 90%, 95% or more of an area of the distal hole 214 of the needle body 208 when the grasper arm 294 is in the first position 254.

As shown in FIGS. 133-135, another exemplary grasper member configuration is an integral ferrule 326. In this configuration, the magnet-assisted suture grasper 200 can include a grasper member 246 that comprises a grasper arm 294 comprising a proximal end 296, a proximal-to-intermediate portion 298, a distal portion 300, and a distal end 302. In the integral ferrule 326, the grasper arm 294 is integral to the grasper ferrule 232.

The increased flexibility in shapes that can be created allows using a flat wire 312 for formation of the integral ferrule 326. The integral ferrule 326 provides an advantage in terms of a decreased part-count in the magnet-assisted suture grasper 200. This simplifies assembly and reduces the complexity of the supply chain for the device.

The integral ferrule 326 can be formed using the same metal forming techniques described above. The flat wire 312 is altered slightly to provide opposing first and second portions 328 at a proximal portion 330 of the flat wire 312 that are folded inward to form the grasper ferrule 232. The remaining flat portion 332 corresponds to the grasper arm 294.

Assembly of a grasper ferrule subassembly 270 including the integral ferrule 326 can be accomplished by inserting the magnet wire 260 into the ferrule lumen 224 of the integral ferrule 326, then crimping the integral ferrule 326 onto the magnet wire 260 as described above. The resulting grasper ferrule subassembly 270 can be joined to the retriever tube 224 as described above. Alternatively, the retriever tube 224 can be crimped onto the grasper ferrule 232 and the proximal portion 262 of the magnet wire 260, with the grasper ferrule 232 and the proximal portion 262 of the magnet wire 260 being disposed within the retriever tube lumen 230, and with the proximal portion 262 of the magnet wire 260 being disposed adjacent the grasper ferrule 232 and not within the ferrule lumen 244 of the grasper ferrule 232, also as described above.

The integral ferrule 326 can also be formed using other approaches.

For example, as shown in FIGS. 136-138, in a first alternate approach the integral ferrule 326 can be formed from a cut tube 334. A cut portion 336 of the cut tube 334 has been removed. This can be accomplished by use of a precision metal cutting process, such as such as laser cutting, electro-discharge machining, micro-waterjet cutting, or CNC machining. A tube is cut, and the cut portion 336 is discarded, leaving a cylindrical portion 338 and a semi-cylindrical portion 340, comprising a single member. The grasper arm 294 is formed from the semi-cylindrical portion 340 of the cut tube 334. This can be accomplished by use of a metal forming process, such as bending, die stamping, or coining. The remaining cylindrical portion 338 of the cut tube 334 corresponds to the grasper ferrule 232.

Accordingly, in some of these embodiments, the grasper member 246 comprises a grasper arm 294 comprising a proximal end 296, a proximal-to-intermediate portion 298, a distal portion 300, and a distal end 302. The grasper arm 294 is integral to the grasper ferrule 232. The grasper magnet 258 is disposed adjacent the proximal-to-intermediate portion 296 of the grasper arm 294.

In some of these embodiments, the grasper ferrule 232 and the grasper arm 294 are formed from a flat wire 312 having a rectangular cross-section. In these embodiments, the grasper ferrule 232 comprises opposing first and second portions 328 of the flat wire 312 that have been folded inwardly toward each other, thereby forming the grasper ferrule 232. The grasper member 246 further comprises an angled distal terminus 314 at the distal end 302 of the grasper arm 294. The grasper arm 294 is reversibly moveable between the first position 254 and the second position 256 based on translation of the grasper arm 294 from inside of the needle lumen 216 to outside of the needle lumen 216 through the distal hole 214 of the needle body 208. The angled distal terminus 314 has a size sufficiently small to allow contact between the grasper magnet 258 and a suture magnet 502 of a magnetic suture 500 attracted thereto when the grasper arm 294 is in the second position 256 and to allow a suture 504 of the magnetic suture 500 to pass when the grasper arm 294 is in the first position 254, and sufficiently large to block the suture magnet 502 of the magnetic suture 500 from exiting the needle lumen 216 through the distal hole 214 of the needle body 208 when the grasper arm 294 is in the first position 254.

In some examples of these embodiments, the angled distal terminus 314 comprises a hook 318.

Also in some examples of these embodiments, the angled distal terminus 314 fills 80% or more of an area of the distal hole 214 of the needle body 208 when the grasper arm 294 is in the first position 254, e.g., 85%, 90%, 95% or more of an area of the distal hole 214 of the needle body 208 when the grasper arm 294 is in the first position 254.

Also in some of these embodiments, the grasper ferrule 232 and the grasper arm 294 are formed from a cut tube 334 comprising a cylindrical portion 338 and a semi-cylindrical portion 340. In these embodiments, the cylindrical portion 338 of the cut tube 334 comprises the grasper ferrule 232. The semi-cylindrical portion 340 of the cut tube 334 comprises the grasper arm 294. The grasper member 246 further comprises an angled distal terminus 314 at the distal end 302 of the grasper arm 294. The grasper arm 294 is reversibly moveable between the first position 254 and the second position 256 based on translation of the grasper arm 294 from inside of the needle lumen 216 to outside of the needle lumen 216 through the distal hole 214 of the needle body 208. The angled distal terminus 314 has a size sufficiently small to allow contact between the grasper magnet 258 and a suture magnet 502 of a magnetic suture 500 attracted thereto when the grasper arm 294 is in the second position 256 and to allow a suture 504 of the magnetic suture 500 to pass when the grasper arm 294 is in the first position 254, and sufficiently large to block the suture magnet 502 of the magnetic suture 500 from exiting the needle lumen 216 through the distal hole 214 of the needle body 208 when the grasper arm 294 is in the first position 254.

In some examples of these embodiments, the angled distal terminus 314 comprises a hook 318.

Also in some examples of these embodiments, the angled distal terminus 314 fills 80% or more of an area of the distal hole 214 of the needle body 208 when the grasper arm 294 is in the first position 254, e.g., 85%, 90%, 95% or more of an area of the distal hole 214 of the needle body 208 when the grasper arm 294 is in the first position 254.

Also in some of these embodiments, the grasper ferrule 232 has been crimped onto the magnet wire 260 with the proximal portion 262 of the magnet wire 260 being disposed within the ferrule lumen 244 of the grasper ferrule 232; and the retriever tube 224 has been crimped onto the grasper ferrule 232 with the grasper ferrule 232 and the proximal portion 262 of the magnet wire 260 being disposed within the retriever tube lumen 230.

Also in some of these embodiments, the retriever tube 224 has been crimped onto the grasper ferrule 232 and the proximal portion 262 of the magnet wire 260, with the grasper ferrule 232 and the proximal portion 262 of the magnet wire 260 being disposed within the retriever tube lumen 230, and with the proximal portion 262 of the magnet wire 260 being disposed adjacent the grasper ferrule 232 and not within the ferrule lumen 244 of the grasper ferrule 232.

Figure 55:
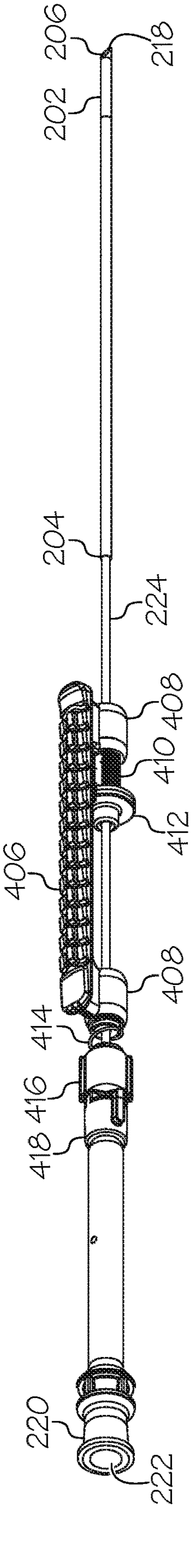
FIG. 55 is a perspective view of the advancer assembly of the magnet-assisted suture grasper of FIG. 1, in which the advancer assembly is in an unlocked fully retracted position.
Figure 56:
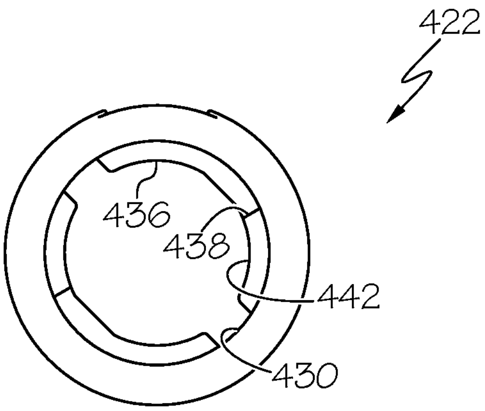
FIG. 56 is a proximal end view of a barrel of the magnet-assisted suture grasper of FIG. 1.
Figure 57:
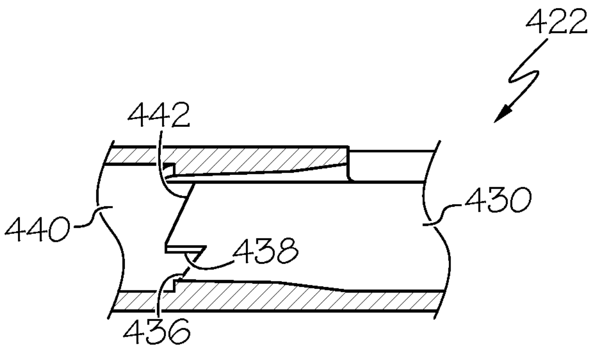
FIG. 57 is a partial longitudinal view of the barrel of FIG. 56.
Figure 58:
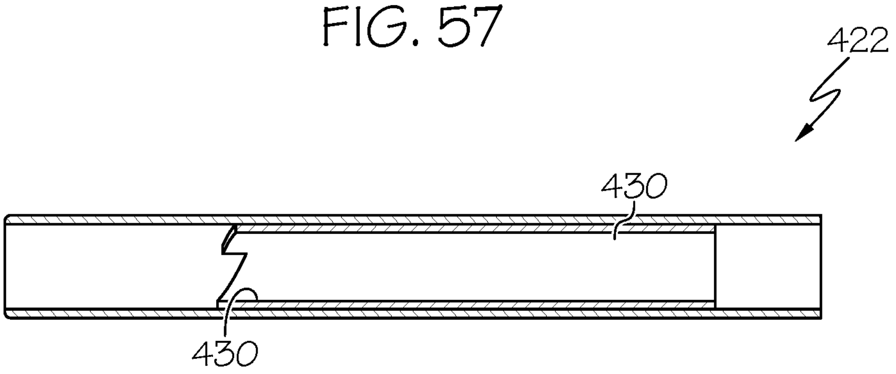
FIG. 58 is a partial sectional view of the barrel of FIG. 56 through guide channels of the barrel.
Figure 59:
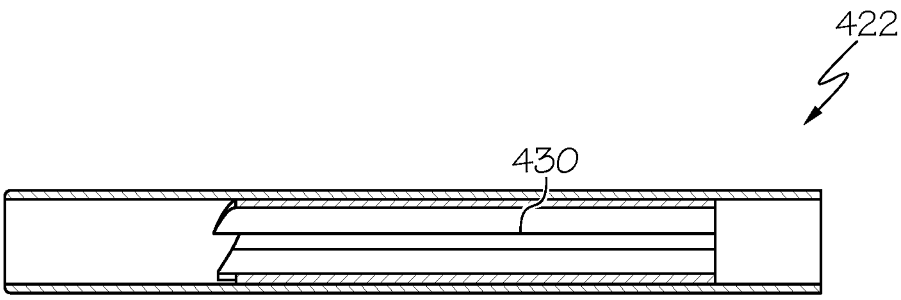
FIG. 59 is a partial sectional view of the barrel of FIG. 56 perpendicular to guide channels of the barrel.
Figure 60:
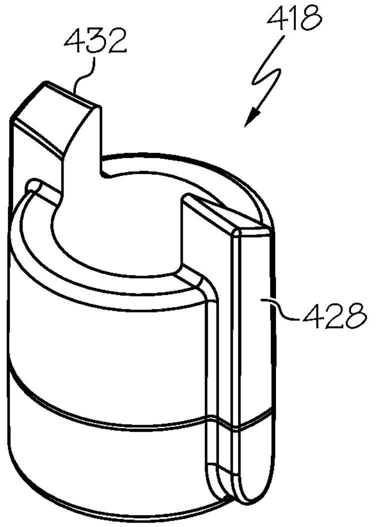
FIG. 60 is a perspective view of a lock cam of the magnet-assisted suture grasper of FIG. 1.
Figure 61:
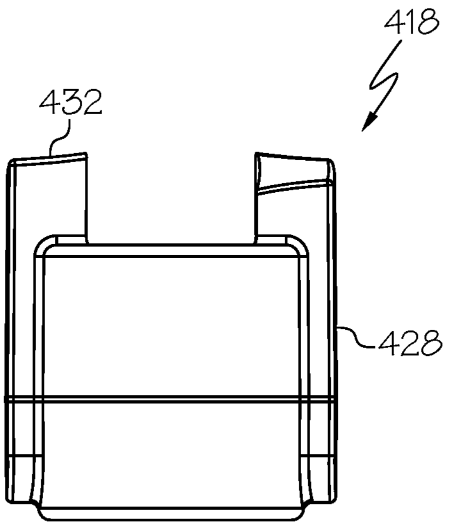
FIG. 61 is a side view of the lock cam of FIG. 60.
Figure 62:
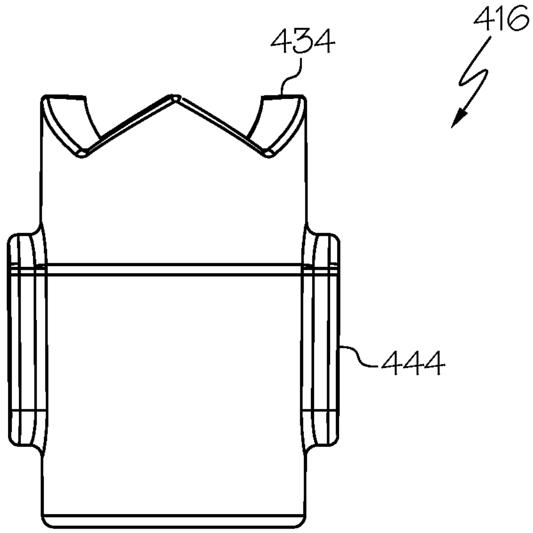
FIG. 62 is a side view of a drive cam of the magnet-assisted suture grasper of FIG. 1.
Figure 63:
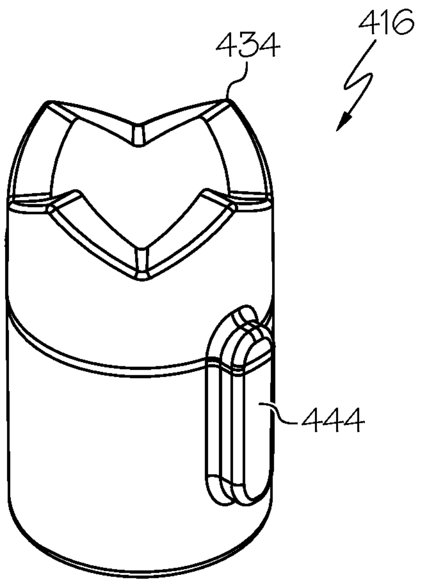
FIG. 63 is a perspective view of the drive cam of FIG. 62.
Figure 64:
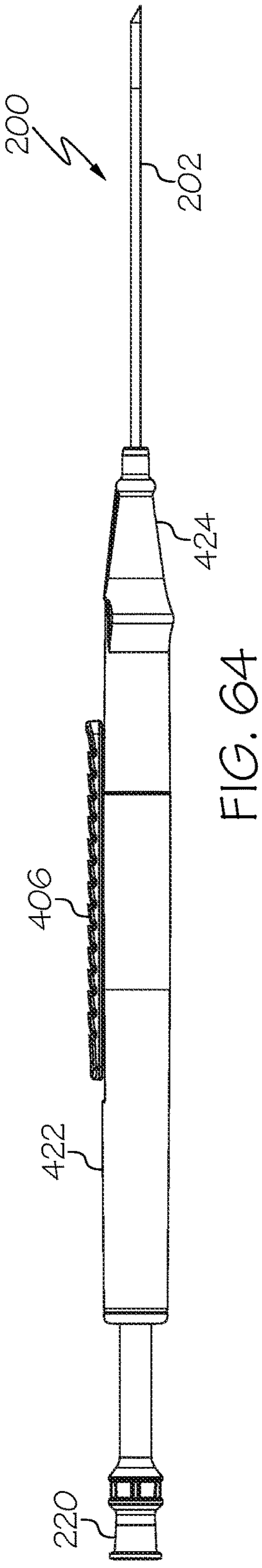
FIG. 64 is a side view of the magnet-assisted suture grasper of FIG. 1, in which the advancer assembly is in a locked partially retracted position and the grasper member is in the first position.
Figure 65:
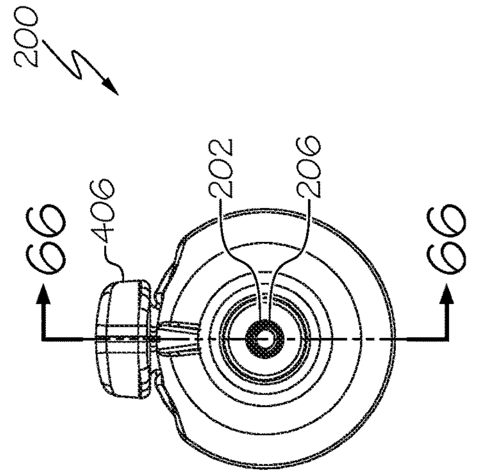
FIG. 65 is a front view of the magnet-assisted suture grasper of FIG. 64.
Figure 66:
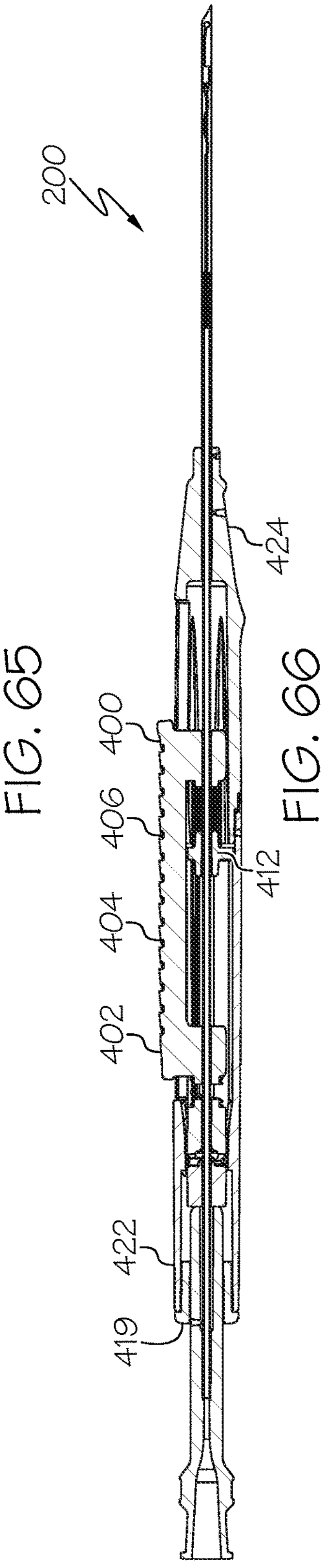
FIG. 66 is a side sectional view of the magnet-assisted suture grasper of FIG. 64, viewed along the cutting plane shown in FIG. 65.
Figure 67:
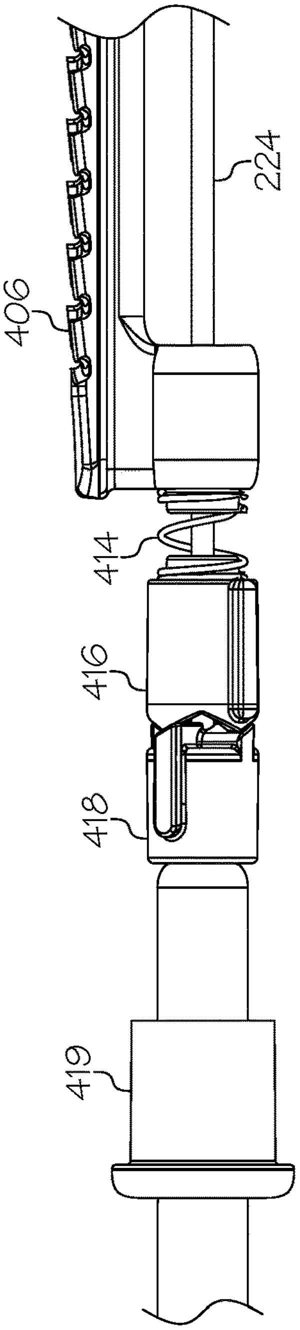
FIG. 67 is a side view of a lock cam, a drive cam, a cam spring, a carrier, a luer, a cap bushing, and the retriever tube of the magnet-assisted suture grasper of FIG. 64.
Figure 68:
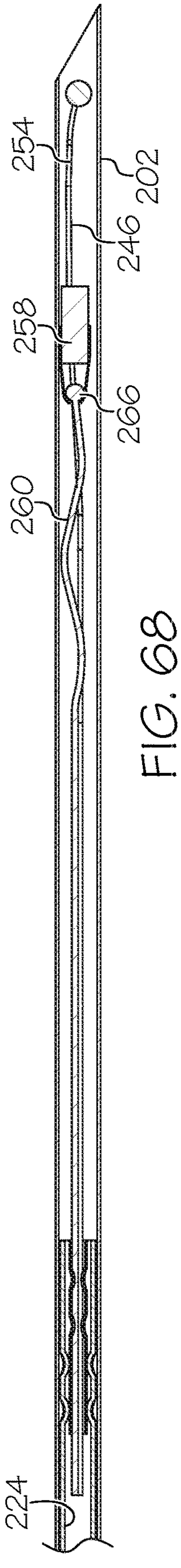
FIG. 68 is an expanded side sectional view of the suture retrieval needle, the retriever tube, the grasper ferrule, the grasper member, the grasper magnet, and the magnet wire of the magnet-assisted suture grasper of FIG. 64, viewed along the cutting plane shown in FIG. 65.
Figure 69:
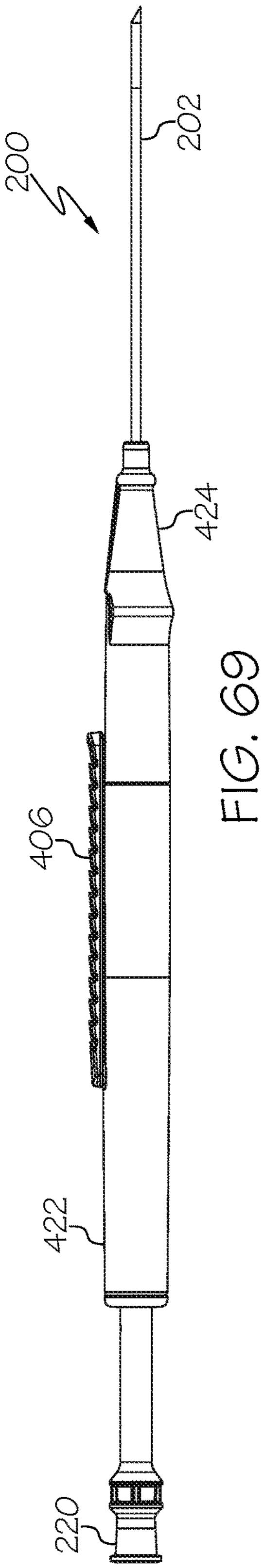
FIG. 69 is a side view of the magnet-assisted suture grasper of FIG. 1, in which the advancer assembly is in a fully retracted position.
Figure 70:
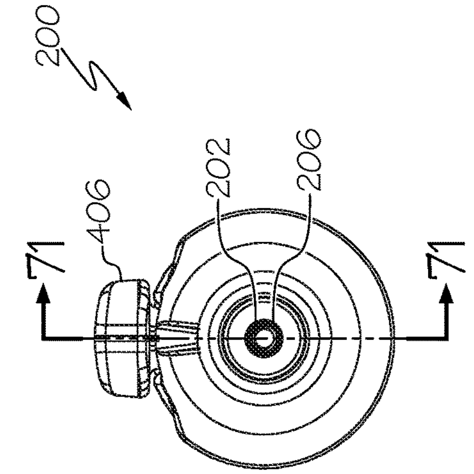
FIG. 70 is a front view of the magnet-assisted suture grasper of FIG. 69.
Figure 71:
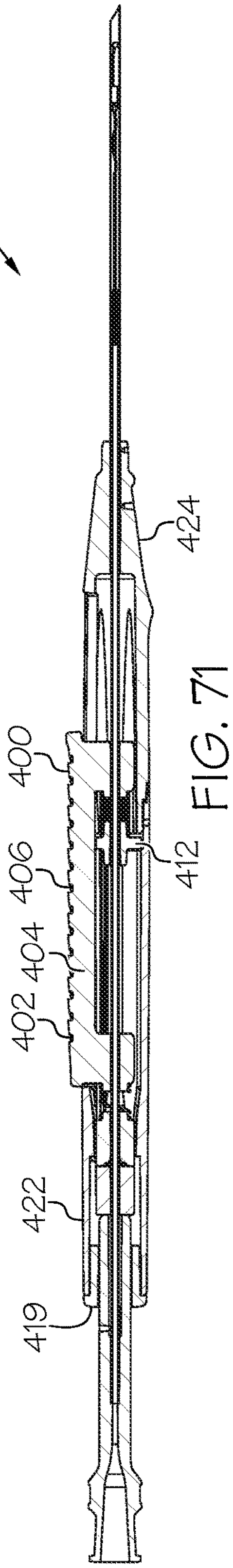
FIG. 71 is a side sectional view of the magnet-assisted suture grasper of FIG. 69, viewed along the cutting plane shown in FIG. 70.
Figure 72:
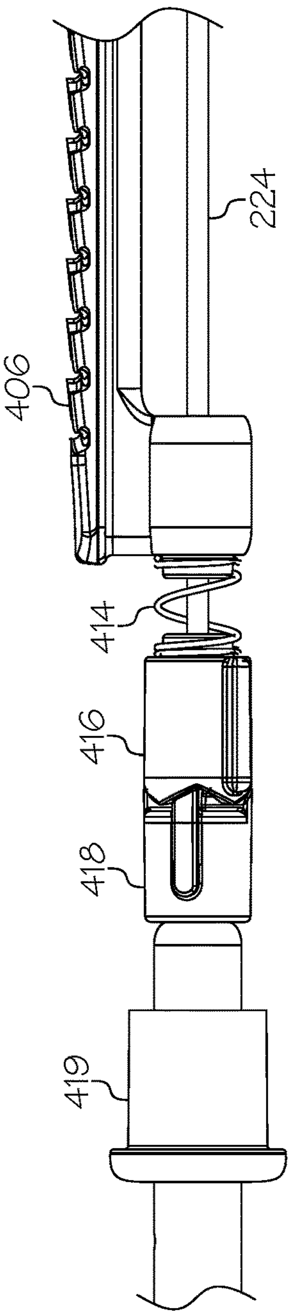
FIG. 72 is a side view of a lock cam, a drive cam, a cam spring, a carrier, a luer, a cap bushing, and the retriever tube of the magnet-assisted suture grasper of FIG. 69.
Figure 73:
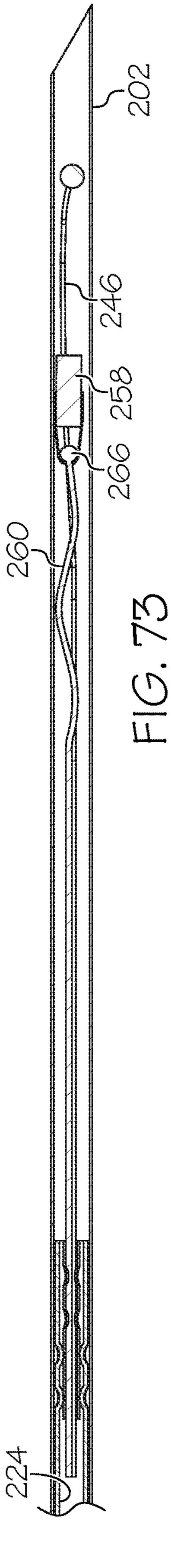
FIG. 73 is an expanded side sectional view of the suture retrieval needle, the retriever tube, the grasper ferrule, the grasper member, the grasper magnet, and the magnet wire of the magnet-assisted suture grasper of FIG. 69, viewed along the cutting plane shown in FIG. 70.

As shown in FIGS. 1-7 and FIG. 9-15, in some embodiments, the magnet-assisted suture grasper 200 further comprises a proximal hub 220. The proximal hub 220 is located at a proximal end of the magnet-assisted suture grasper 200. As shown in FIG. 55, the proximal hub 220 can have an open lumen 222. In some embodiments, the proximal hub 220 is rigidly fixed to the retriever tube 224. In some embodiments, the proximal hub 220 is rigidly fixed to the suture retrieval needle 220.

In some embodiments the magnet-assisted suture grasper 200 further comprises the proximal hub 220 and a handle attached to the retriever tube 224. This is advantageous for improving the ergonomics of the magnet-assisted suture grasper 200 by allowing for single-handed operation. The handle would preferentially include a non-axisymmetric design so as to rotationally fix the handle and the retriever tube 224.

Also in some embodiments the magnet-assisted suture grasper 200 further comprises a return mechanism, such as a spring. In these embodiments, the retriever tube 224 can be attached directly to the handle, so that when the handle is depressed, the retriever tube 224 is advanced, which in turn advances the grasper member 246 and the grasper magnet 258 from the needle lumen 216. When the handle is released, the spring returns the handle to the original position. This returns the grasper member 246 and the grasper magnet 258 to the needle lumen 216.

A description of operation of an exemplary magnet-assisted suture grasper 200 follows. In this description, the grasper member 246 of the magnet-assisted suture grasper 200 comprises a grasper wire 288 and a grasper arm 294.

After a magnetic suture 500 has been deposited inside a patient, the suture retrieval needle 202 is introduced into the patient to gain access to the site of the magnetic suture 500. The retriever tube 224 is used to advance the grasper arm 294 and the grasper magnet 258 through the needle lumen 216 of the suture retrieval needle 202 until the grasper arm 294 and the grasper magnet 258 exit the needle lumen 216, extending past the distal hole 214 of the needle body 208. The grasper arm 294 and the grasper magnet 258 are brought near the suture magnet 502 of the magnetic suture 500, so that the magnetic fields of the grasper magnet 258 and the suture magnet 502 can interact. The attractive force between the grasper magnet 258 and the suture magnet 502 pulls the suture magnet 502 towards the grasper magnet 258 and brings them into contact and axial alignment.

Then the retriever tube 224 is used to pull the grasper arm 294 and the grasper magnet 258 back inside the needle lumen 216 of the suture retrieval needle 202. The attractive force between the grasper magnet 258 and the suture magnet 502 allows the grasper magnet 258 to tow the suture magnet 502, and the attached suture 504, along with it. The retriever tube 224 is pulled back until the grasper magnet 258 and the suture magnet 502 are brought entirely inside the needle lumen 216. At this point, the magnetic suture 500 cannot escape the suture retrieval needle 202, because the distal end 302 of the grasper arm 294 blocks the exit path. The proximal end of the grasper arm 294 is attached to the retriever tube 224, so the grasper arm 294 is not moved by the magnetic suture 500.

Once the magnetic suture 500 has been captured, the magnet-assisted suture grasper 200 can be used to pull or push the magnetic suture 500 to a new location. The grasper arm 294 allows the magnet-assisted suture grasper 200 to hold the magnetic suture 500 securely, even when the magnetic suture 500 is heavily loaded to the point that the load exceeds the attractive force between grasper magnet 258 and the suture magnet 502. The grasper arm 294 prevents the suture magnet 502 of the magnetic suture 500 from being pulled back out of the needle lumen 216, even when the force applied exceeds the strength of attraction between the grasper magnet 258 and the suture magnet 502.

Once the magnetic suture 500 has been passed to the desired location, the magnetic suture 500 can be released from the magnet-assisted suture grasper 200. To release the magnetic suture 500, the retriever tube 224 is used to advance the grasper arm 294, the grasper magnet 258, and the suture magnet 502 out of the needle lumen 216, and the suture 504 can then be pulled to disconnect the grasper magnet 258 and the suture magnet 502.

As shown in FIGS. 1-17, in some embodiments, the magnet-assisted suture grasper 200 further comprises a lock mechanism 400 that can be reversibly engaged to prevent translation of the retriever tube 224 within the needle lumen 216 in the first direction and/or the second direction. The lock mechanism 400 can be advantageous for bearing fully a tensile load applied to a magnetic suture 500 in the same direction.

In some of these embodiments, the lock mechanism 400 can be reversibly engaged in a first setting that prevents translation of the retriever tube 224 within the needle lumen 216 in the first direction but not the second direction when the distal end 302 of the grasper arm 294 is inside the needle lumen 216 and reversibly engaged in a second setting that prevents translation of the retriever tube 224 within the needle lumen 216 in the first direction but not the second direction when the grasper magnet 258 is outside of the needle lumen 216. In some examples of these embodiments, maintaining the lock mechanism 400 in the first setting or the second setting does not require energy input.

A magnet-assisted suture grasper 200 comprising an exemplary lock mechanism 400 and a trap wire 304 comprising a grasper arm loop 306 is shown in FIGS. 1-17, with reference to FIGS. 55-63. The magnet-assisted suture grasper 200 comprises an advancer assembly 402 comprising the retriever tube 224, an advancer frame 404 including proximal and distal guide bushings 408, an advancer pad 406, a return spring 410, a spring keeper 412, a cam spring 414, a drive cam 416, a lock cam 418, a cap bushing 419, a proximal hub 220, and an end effector 420 comprising the trap wire 304 and the magnet wire 260 with the grasper magnet 258 attached. In accordance with these examples, the end effector 420 is rigidly fixed to the retriever tube 224. The retriever tube 224 passes through the proximal and distal guide bushings 408 of the advancer frame 404, the spring keeper 412, the drive cam 416, and the lock cam 418, terminating within the body of the proximal hub 220. The proximal hub 220 and the advancer frame 404 are rigidly fixed to the retriever tube 224, and the advancer pad 406 is rigidly fixed to the advancer frame 404. The spring keeper 412 is not fixed within the advancer assembly 402, but is laterally constrained by a barrel 422 and nose cone 424, such that the spring keeper 412 has a longitudinal position that is fixed relative to these components. The entire advancer assembly 402 slides within the inner channel of the barrel 422 and nose cone 424, such that the return spring 410 compresses between the distal guide bushing 408 of the advancer frame 404 and the spring keeper 412 during this motion. The proximal and distal guide bushings 408 of the advancer frame 404 keep the components aligned axially and moving smoothly during sliding of the advancer assembly 402. The cap bushing 419 also assists in keeping the components axially aligned.

The magnet-assisted suture grasper 200 comprising the lock mechanism 400 and the trap wire 304 can be operated as follows.

Initially, the advancer assembly 402 of the magnet-assisted suture grasper 200 is in a locked partially retracted position and the grasper arm 294 is in the first position 254, as shown in FIGS. 64-68. The system is in a state of equilibrium, such that no external force is required to maintain this position.

To begin operation, the operator briefly pulls the advancer assembly 402 back with sufficient force to compress the return spring 410, until the advancer frame 404 engages the maximal boundary of a travel slot 426, to put the advancer assembly 402 in an unlocked fully retracted position, as shown in FIGS. 69-73, with reference to FIGS. 56-63. During this movement, the lock cam 418 engages the drive cam 416, and the lock cam teeth 432 are rotated into a valley in the crown of the drive cam 416. A continual application of external force, e.g., as applied by the operator, sufficient to overcome the elastic strain that has been loaded into the return spring 410, is required to maintain the advancer assembly 402 in this position.

To continue operation, the operator releases the advancer assembly 402 from this position. The return spring 410 then pushes the advancer assembly 402 forward, and the lock cam teeth 432 engage the channel ramps 442 in the barrel 422. The channel ramps 442 guide the teeth 432 and guide lugs 428 of the lock cam 418 into the linear guide channels 430.

Figure 74:
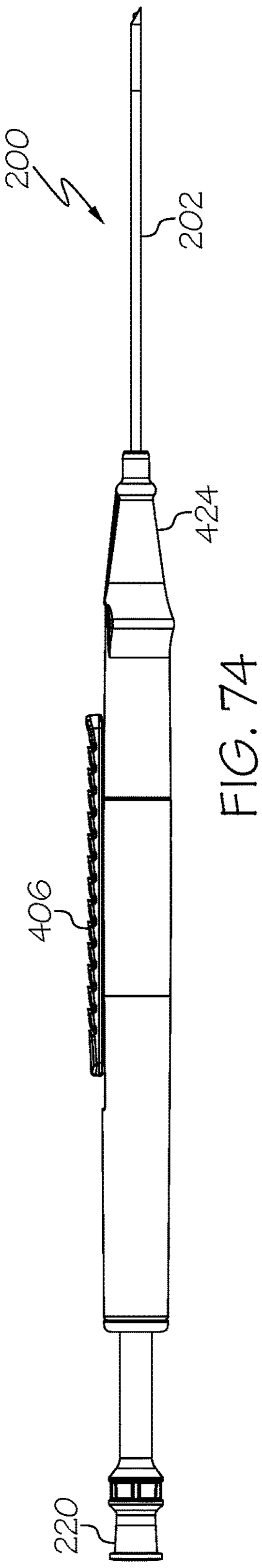
FIG. 74 is a side view of the magnet-assisted suture grasper of FIG. 1, in which the advancer assembly is in an unlocked partially retracted position.
Figure 75:
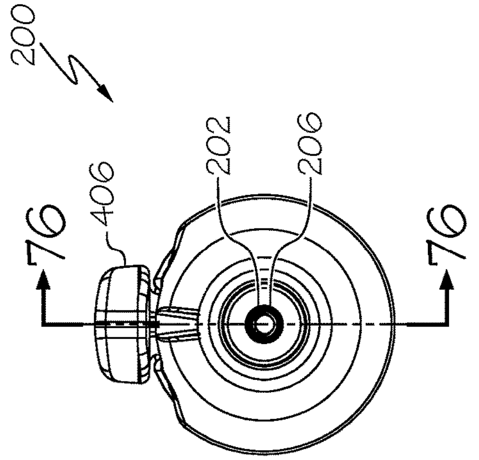
FIG. 75 is a front view of the magnet-assisted suture grasper of FIG. 74.
Figure 76:
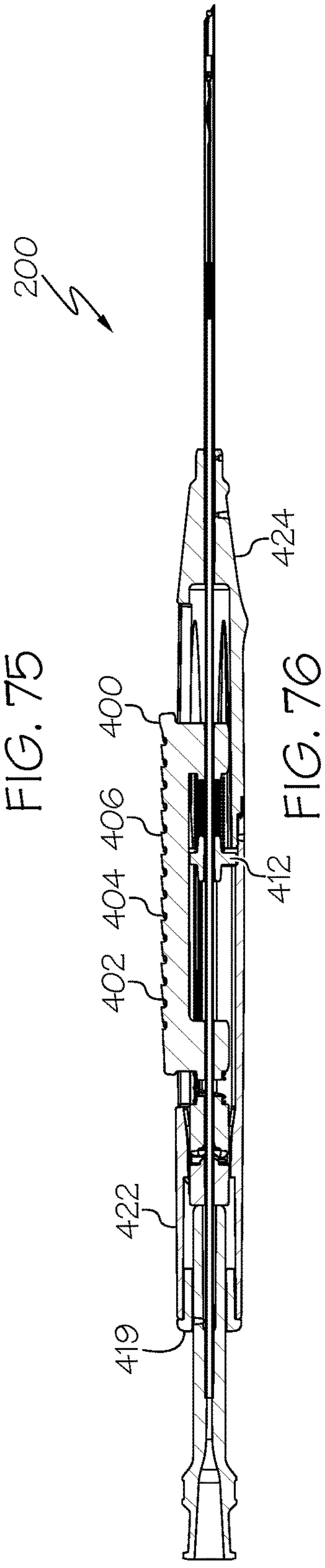
FIG. 76 is a side sectional view of the magnet-assisted suture grasper of FIG. 74, viewed along the cutting plane shown in FIG. 75.
Figure 77:
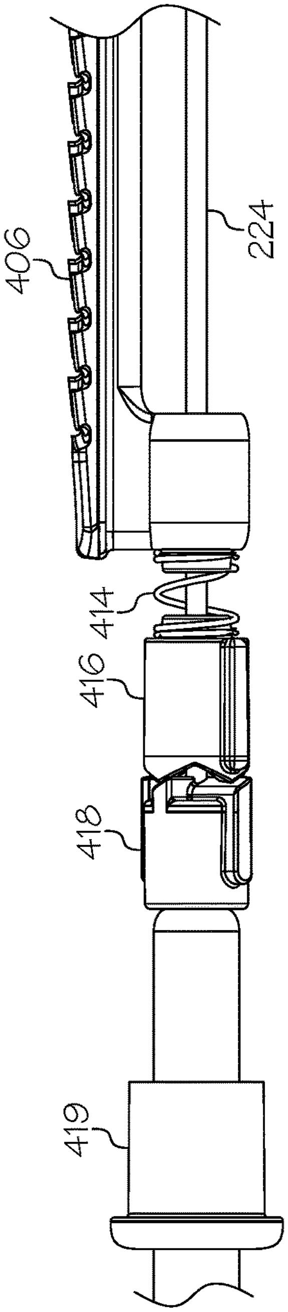
FIG. 77 is a side view of a lock cam, a drive cam, a cam spring, a carrier, a luer, a cap bushing, and the retriever tube of the magnet-assisted suture grasper of FIG. 74.
Figure 78:
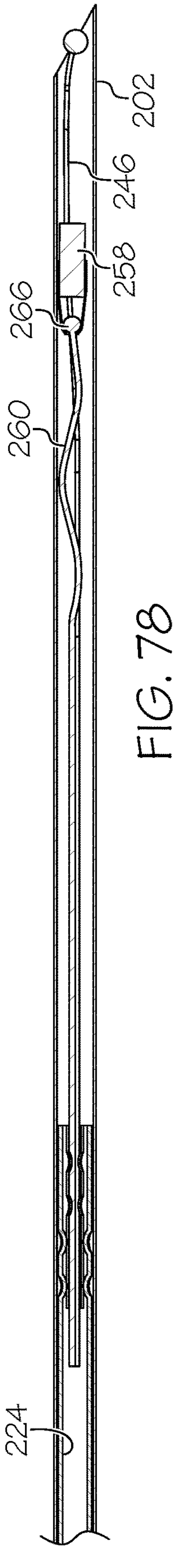
FIG. 78 is an expanded side sectional view of the suture retrieval needle, the retriever tube, the grasper ferrule, the grasper member, the grasper magnet, and the magnet wire of the magnet-assisted suture grasper of FIG. 74, viewed along the cutting plane shown in FIG. 75.
Figure 79:
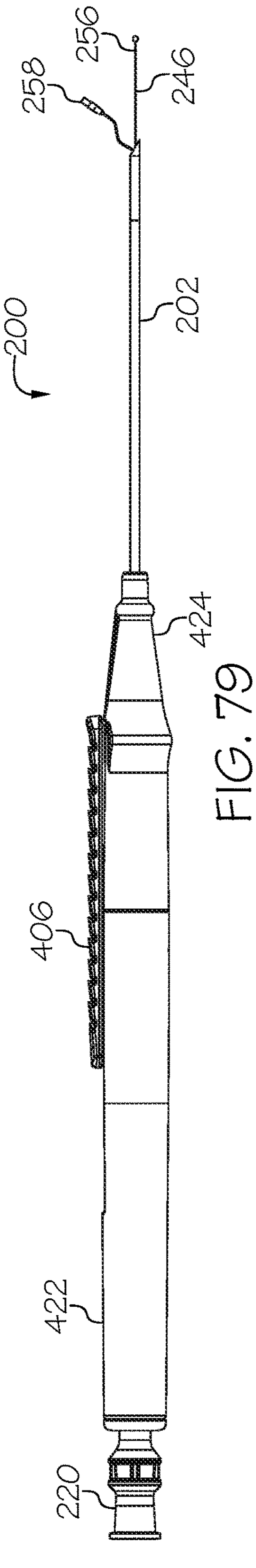
FIG. 79 is a side view of the magnet-assisted suture grasper of FIG. 1, in which the advancer assembly is in a locked fully extended position, the grasper member is in the second position, and the grasper magnet is exposed from the suture retrieval needle.
Figure 80:
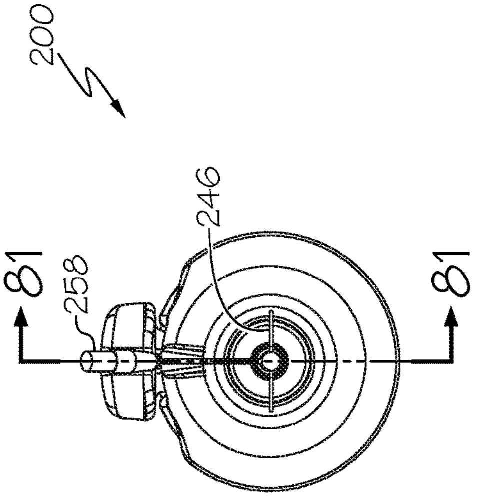
FIG. 80 is a front view of the magnet-assisted suture grasper of FIG. 79.
Figure 81:
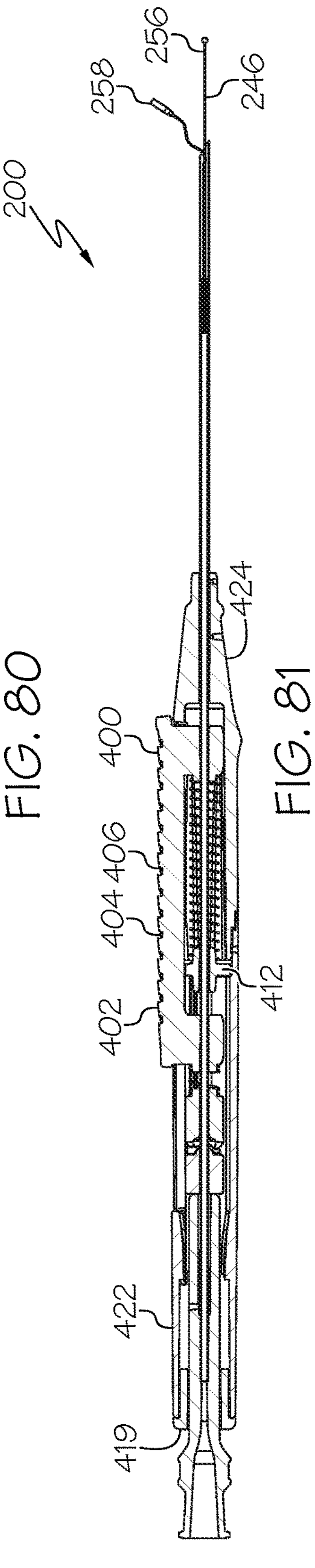
FIG. 81 is a side sectional view of the magnet-assisted suture grasper of FIG. 79, viewed along the cutting plane shown in FIG. 80.
Figure 82:
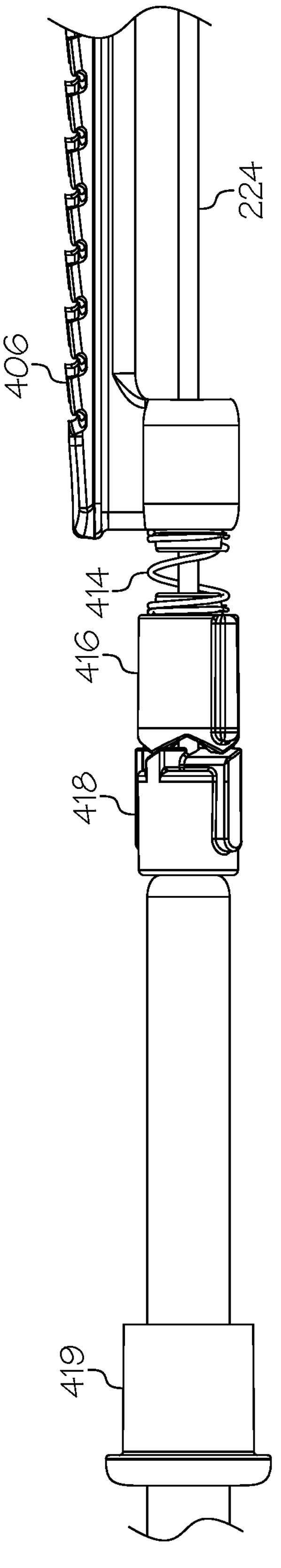
FIG. 82 is a side view of a lock cam, a drive cam, a cam spring, a carrier, a luer, a cap bushing, and the retriever tube of the magnet-assisted suture grasper of FIG. 79.

The return spring 410 pushes the advancer assembly 402 forward through an unlocked partially retracted position, as shown in FIGS. 74-76, and continues to push the advancer assembly 402 forward until the advancer frame 404 engages the minimum boundary of the travel slot 426, pushing the end effector 420 out of the suture retrieval needle 202, as shown in FIGS. 79-83.

At this point, the advancer assembly 402 is in a locked extended position and the grasper arm 294 is in the second position 256. The system is in a state of equilibrium in this position, where no external force is required to maintain this position.

To continue operation, the operator pulls the advancer assembly 402 back, again with sufficient force to compress the return spring 410, through the unlocked partially retracted position, as shown in FIGS. 74-78, to the unlocked fully retracted position as shown in FIGS. 69-73. This pulls the end effector 420 into the needle lumen 216 and pushes the lock cam 418 into a relieved space 440 proximal to the locking features of the barrel 422. With the guide lugs 428 of the lock cam 418 now freed from the rotational constraint imposed by linear guide channels 430 of the barrel 422, the force exerted by the (preloaded) cam spring 414 is translated into a rotational movement of the lock cam 418 by way of mating lock cam teeth 432 and drive cam teeth 434 between the lock cam 418 and drive cam 416. Rotation of the lock cam 418 is halted when crests of the lock cam teeth 432 become nested in valleys between drive cam teeth 434. At this point, the advancer assembly 402 is again in the unlocked fully retracted position. Again, a continual application of external force sufficient to overcome the elastic strain that has been loaded into the return spring 410 is required to maintain the advancer assembly 402 in this position.

To continue operation, the operator releases the advancer assembly 402, which, in the absence of any external force, is pushed forward by the return spring 410, which had been compressed in the previous position. As the advancer assembly 402 moves forward, the lock cam teeth 432 slide along the lock ramps 436 of the barrel 422, resulting in simultaneous linear and rotational translation of the lock cam 418. This continues until the lock cam teeth 432 meet the lock stops 438 in the barrel 422, at which point the advancer assembly 402 becomes mechanically locked against any further movement in this direction. At this point, the advancer assembly 402 has returned to the locked partially retracted position and the grasper arm 294 has returned to the first position 254, as shown in FIGS. 64-68. Again, the system is in a state of equilibrium in this position, such that no external force is required to maintain this position.

Figure 83:
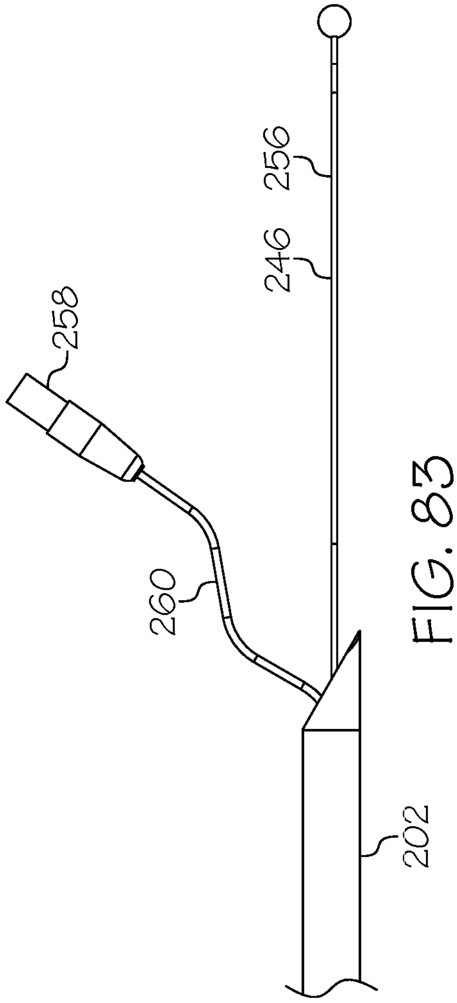
FIG. 83 is a side view of a distal portion of the magnet-assisted suture grasper of FIG. 79.
Figure 85:
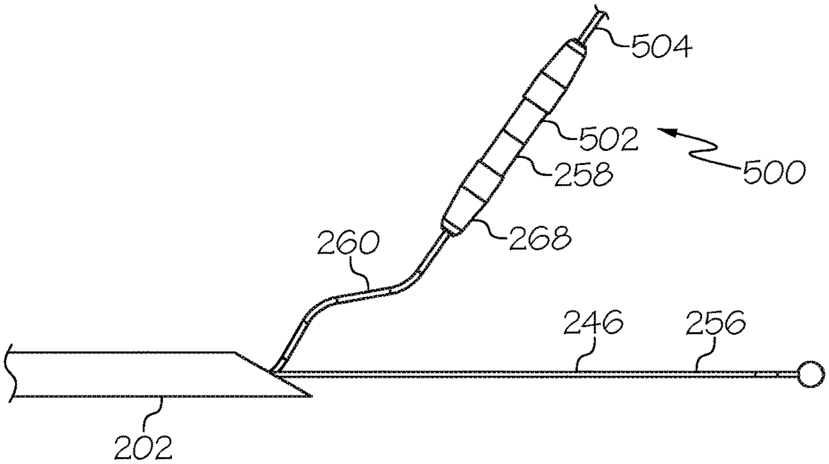
FIG. 85 is a side view of the distal portion of the magnet-assisted suture grasper of FIG. 84, in which the grasper magnet is attracting a magnetic suture and in contact with the magnetic suture.

The magnet-assisted suture grasper 200 comprising the lock mechanism 400 and the trap wire 304 relies on magnetic attraction to establish a steady-state connection between the magnet-assisted suture grasper 200 and a magnetic suture 500 when in the locked extended position. With reference to FIGS. 83-85, the operator moves the advancer assembly 402 forward such that the advancer assembly 402 is in the locked extended position and the grasper arm 294 is in the second position 256. The trap wire 304 and the grasper magnet 258 are brought near the suture magnet 502 of the magnetic suture 500. The trap wire 304 and the grasper magnet 258 do not need to be precisely aligned with the suture magnet 502, but only brought near so that the magnetic fields of the grasper magnet 258 and the suture magnet 502 may interact, allowing the magnetic moments to pull the southern pole of the suture magnet 502 into contact with the northern pole of the grasper magnet 258, thereby establishing a steady-state connection between the magnet-assisted suture grasper 200 and a magnetic suture 500.

Figure 86:
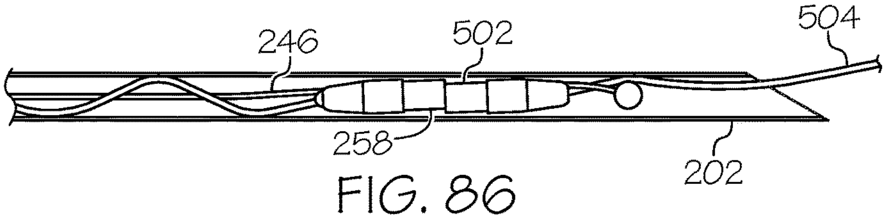
FIG. 86 is a side sectional view of a distal portion of the magnet-assisted suture grasper of FIG. 84, in which the advancer assembly is in an unlocked fully retracted position, the grasper member is sequestering the grasper magnet within the suture retrieval needle, and the grasper magnet is attracting a magnetic suture and in contact with the magnetic suture, such that the magnetic suture has been captured within the needle lumen of the suture retrieval needle of the magnet-assisted suture grasper.

With reference to FIG. 86, the magnet-assisted suture grasper 200 can then accomplish mechanical capture of the magnetic suture 500 by moving from the locked extended position to the unlocked fully retracted position as follows. After initial attraction, the operator briefly pulls the advancer assembly 402 back, thereby bringing the advancer assembly 402 through the unlocked partially retracted position and returning the advancer assembly 402 to the unlocked fully retracted position. The steady-state connection between grasper magnet 258 and the suture magnet 502 allows the grasper magnet 258 to tow the magnetic suture 500 into the needle lumen 216. The length of the trap wire 304 is designed such that the enlarged distal terminus 308 at the end of the trap wire 304 maintains a distal position relative to the suture magnet 502 inside the needle lumen 216. This allows the enlarged distal terminus 308 to act as a plug, creating a physical blockage inside the needle lumen 216 by which the suture magnet 502 of the magnetic suture 500 cannot pass.

Figure 87:
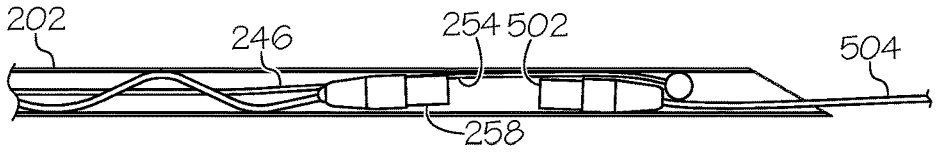
FIG. 87 is a side sectional view of a distal portion of the magnet-assisted suture grasper of FIG. 84, in which the advancer assembly is in a locked partially retracted position, the grasper member is in the first position, and an enlarged distal terminus at the distal portion of the grasper member is grasping the magnetic suture, such that the magnetic suture remains captured within the needle lumen of the suture retrieval needle of the magnet-assisted suture grasper.
Figure 88:
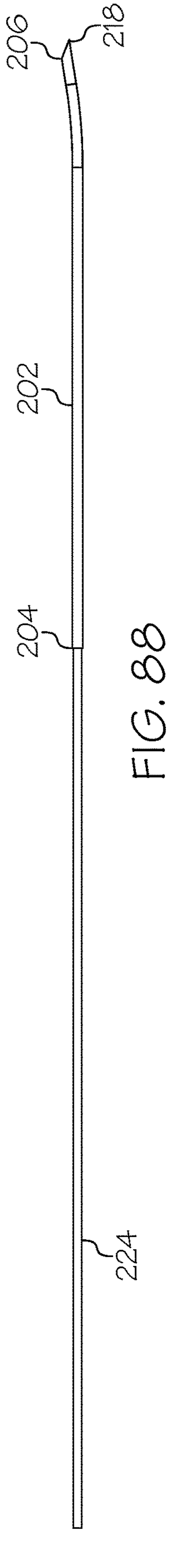
FIG. 88 is a side view of an alternative embodiment of a suture retrieval needle of the magnet-assisted suture grasper of FIG. 1, in which the suture retrieval needle is a curved suture retrieval needle, and the grasper ferrule, the grasper member, the grasper magnet, and the magnet wire of the magnet-assisted suture grasper of FIG. 1, in which the grasper member is in the first position.
Figure 89:
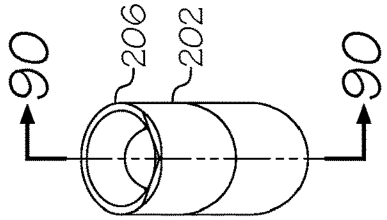
FIG. 89 is a front view of the curved suture retrieval needle and the grasper ferrule, the grasper member, the grasper magnet, and the magnet wire of FIG. 88.
Figure 90:
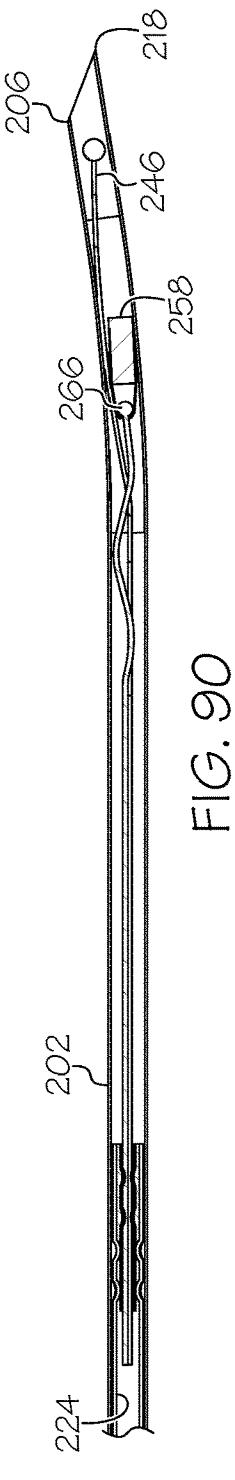
FIG. 90 is an expanded side sectional view of the curved suture retrieval needle and the grasper ferrule, the grasper member, the grasper magnet, and the magnet wire of FIG. 88, viewed along the cutting plane shown in FIG. 89.
Figure 91:
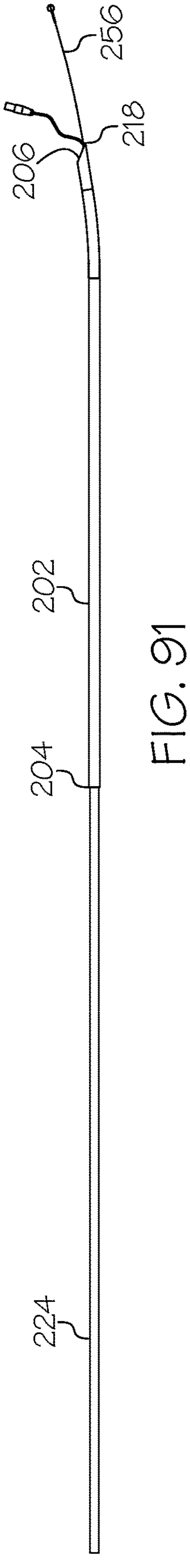
FIG. 91 is a side view of the curved suture retrieval needle and the grasper ferrule, the grasper member, the grasper magnet, and the magnet wire of FIG. 88, in which the grasper member is in the second position.
Figure 92:
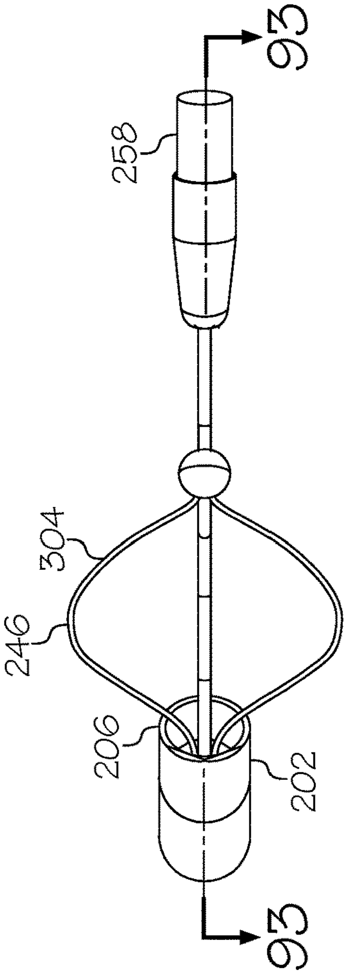
FIG. 92 is a front view of the curved suture retrieval needle and the grasper ferrule, the grasper member, the grasper magnet, and the magnet wire of FIG. 91.
Figure 93:
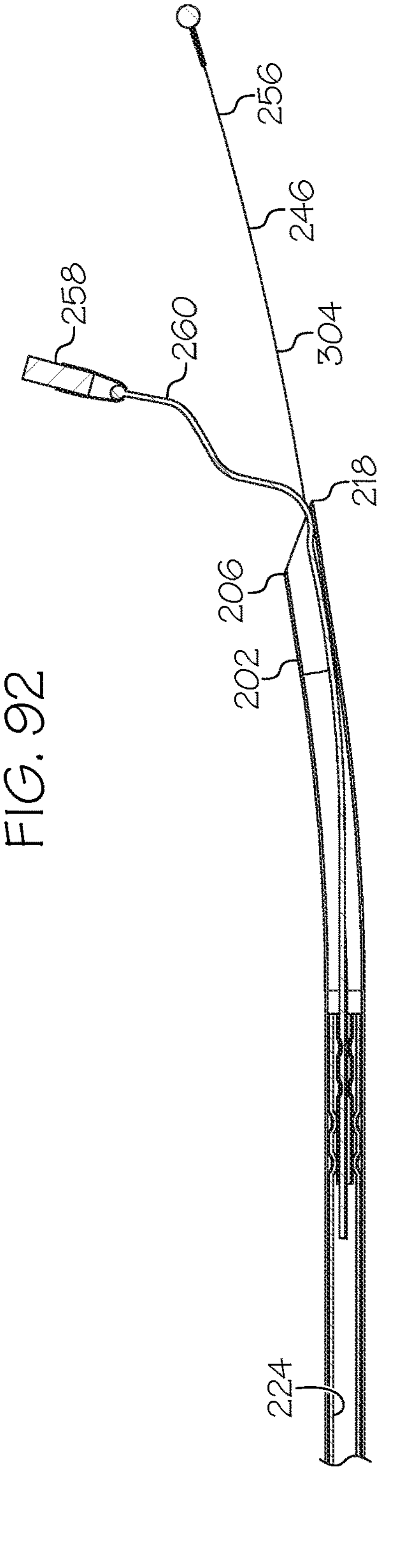
FIG. 93 is an expanded side sectional view of the curved suture retrieval needle and the grasper ferrule, the grasper member, the grasper magnet, and the magnet wire of FIG. 91, viewed along the cutting plane shown in FIG. 92.

With reference to FIG. 87, the magnet-assisted suture grasper 200 can then accomplish mechanical retention of the magnetic suture 500 in the locked partially retracted position as follows. The operator releases the advancer assembly 402, which is pushed forward by the return spring 410, moving the advancer assembly 402 from the unlocked fully retracted position, which is energetically unfavorable, to the locked partially retracted position, which is equipoised. The grasper arm 294 is then in the first position 254. While the advancer assembly 402 remains in the locked partially retracted position, when the magnetic suture 500 is tensely loaded with a force that exceeds the attractive strength between the grasper magnet 258 and the suture magnet 502, the suture magnet 502 will be pulled away from grasper magnet 258, but will be stopped from exiting the needle lumen 216 by the trap wire 304. The tensile load applied to the magnetic suture 500 is thereby borne by the trap wire 304, which is translated through the trap wire 304 into the retriever tube 224 by way of a rigid joint between these two elements, and into the lock cam 418 by way of the proximal hub 220, which is also rigidly joined to the retriever tube 224. As the lock cam 418 is fixedly engaged with mechanical locking features of the barrel 422, this load is ultimately born by the interface between the lock cam 418 and the barrel 422. The ability of the device to resist tensile loading of the magnetic suture 500 is therefore limited by the tensile strength of these individual elements and the joints between them, as well as the shear strength of the lock cam teeth 432 and the lock stops 438 of the barrel 422. The material selections and cross-sectional areas of these elements ultimately define a much higher capacity for load bearing than that of the 3-0 suture this system is designed to work with, so that the suture itself becomes the limiting factor in the system. This is preferable to having another part of the system fail before the magnetic suture 500 because the surgeon is not artificially limited as to the amount of tension that can be applied by way of the magnetic suture 500. Another reason this is preferable is that when the system is overloaded and the magnetic suture 500 breaks, the suture magnet 502 of the magnetic suture 500 remains captured within the needle lumen 216, allowing for safe retrieval and disposal.

The magnet-assisted suture grasper 200 also is designed so that the retriever tube 224 runs centrally through all components. The retriever tube 224 is designed with an open retriever tube lumen 230 that runs the length of the retriever tube 224. The proximal hub 220 at the proximal end of the device is structured with an open lumen 222 that runs the entire length of the proximal hub 220. At the distal end, the needle body 208 is also luminally patent. When assembled, the retriever tube lumen 230 opens to the open lumen 222 of the proximal hub 220 at the proximal end, and the needle lumen 216 of the needle body 208 at the distal end, creating a lumenal path that extends from end to end through the entire device.

Considering the exemplary lock mechanism 400 as shown in more detail, this lock mechanism 400 is formed between three components, the lock cam 418, the drive cam 416, and the barrel 422. The guide lugs 428 of the lock cam 418 and the guide lugs 444 of the drive cam 416 extend from the outer surface of their respective lock cam 418 and drive cam 416 and are disposed 180° apart. The barrel 422 features two guide channels 430, which are relieved into the inner surface and are also disposed 180° apart. When assembled, the guide lugs 428 of the lock cam 418 and the guide lugs 444 of the drive cam 416 fit into and slide within the guide channels 430. The lock cam 418 and drive cam 416 are assembled over the retriever tube 224, distal to the proximal hub 220 and proximal to the advancer frame 404. The cam spring 414 is placed between the advancer frame 404 and the drive cam 416. The cam spring 414 is pre-compressed during assembly so that it exerts a continual force upon the drive cam 416, acting to push the drive cam 416 towards the lock cam 418. The drive cam 416 features a crown of radially disposed V-shaped teeth 434. The lock cam 418 features right-triangle shaped teeth 432 with a matching ramp angle to that of the drive cam teeth 434. The barrel 422 features right angle teeth relieved into the inner surface of the barrel 422, proximal to the guide channels 430, also with ramp angles matching the lock and drive cams 416. The width of the lock cam teeth 432 is wider than the teeth 434 of the drive cam 416, so that the lock cam teeth 432 extend beyond the outer diameter of the drive cam teeth 434. The arrangement of teeth 432 on the lock cam 418 is such that when the lugs 428 of the lock cam 418 and the lugs 444 of the drive cam 416 are aligned, the apexes of the lock cam teeth 432 are slightly aft of the apexes of the nearest drive cam teeth 434. The arrangement of the barrel teeth is such that with the lock cam teeth 432 nested in the valley between drive cam teeth 434, the apexes of the lock cam teeth 432 sit slightly aft to the apex of the barrel teeth 434.

Operationally, the guide lugs 444 of the drive cam 416 remain within the guide channel 430 along all points of linear travel by the sliding assembly. As such, the drive cam 416 is always constrained against rotation about the neutral axis. The lock cam 418 is constrained in the same manner while the guide lugs 428 are positioned within the guide channel 430, but the lock cam 418 fully enters the relieved space 440 created by the barrel teeth 434 at the maximal extent of travel, i.e. the unlocked fully retracted position, which frees the guide lugs 428 of the lock cam 418 from guide channel 430, allowing the lock cam 418 to rotate about the neutral axis. When the guide lugs 428 of the lock cam 418 are freed from the constraints of the guide channel 430, the force exerted by the cam spring 414 drives the drive cam 416 towards the lock cam 418. The ramp angle of the mating lock cam teeth 432 and drive cam teeth 434 causes the lock cam 418 to slide along the drive cam tooth 434 towards the valley between drive cam teeth 434. As the drive cam 416 is rotationally constrained, but the lock cam 418 is not, this movement results in a counter-clockwise rotation of the lock cam 418 (approximately 45°). From this position, the sliding components of the assembly are moved back in the opposite direction, toward the locked extended position, which causes the lock cam teeth 432 to make contact with the lock ramps 436 of the barrel 422. Sliding contact of the lock cam teeth 432 with the lock ramps 436 causes a further counterclockwise rotation of the lock cam 418, until the teeth 432 make contact with the lock stops 438 (approximately 45°). This is the locked position. In this position, further movement from the unlocked fully retracted position to the locked extended position is not possible. The lock is released by the sliding of the moving assembly back to the unlocked fully retracted position, which drives the lock cam teeth 432 beyond the extends of the lock stops 438, at which point the lock cam 418 is rotationally driven further clockwise by the drive cam teeth 434. From this position, the sliding assembly can be driven to locked extended position. As the lock cam 418 advances linearly towards the locked extended position, the lock cam teeth 432 contact the channel ramps 442 in the barrel 422, and the sliding contact results in further counterclockwise rotation of the lock cam 418. At the lower apex of the channel ramps 442 are the guide channels 430, so that as the lock cam teeth 432 slide along the channel ramps 442 the guide lugs 428 are guided into the guide channels 430, allowing the entire sliding assembly to move towards the fully extended position. The rotational nature of this cycle is such that one lock/unlock cycle results in 180° translation of the lock cam 418, and two complete lock/unlock cycles returns the components to their original position (360° rotation). This allows for the lock/unlock cycle to be repeated indefinitely.

As will be appreciated, other lock mechanisms 400 can also be used with the magnet-assisted suture grasper 200. For example, the lock mechanism 400 can include a simple lever arm molded into a proximal hub 220 of the suture retrieval needle 202 and serrations on the outer surface of a retriever tube 224 such that the lever arm can engage with the serrations to lock the retriever tube 224, and thus the grasper wire 288, against translation relative to the suture retrieval needle 202. The lock mechanism 400 also can be a bolt-action lock mechanism in which a simple lever is moved within a J-shaped channel. An off-axis move into the short leg of the J-shaped channel secures the arm against the tensile force applied by the return spring. Another off-axis move repositions the lever into the long leg of the J-shaped channel to return to the original position. The lock mechanism 400 also can be a side button lock mechanism in which a U-shaped flat spring floats within a moving member, and a spring action of the U-shaped flat spring causes the spring to engage with a lip in the moving member to lock the device in an extended position. The U-shaped spring protrudes from the side of the device, forming a button. Pressing the button disengages the U-shaped spring from the lip, allowing a return spring to return the device to a retracted position. The lock mechanism 400 also can be a crossing-path lock mechanism, including a metal pin fixed in a floating carriage. The carriage is longitudinally fixed, but freely rotates, which allows the pin to follow grooves cut in a medial member. The grooves create a crossing path that locks and unlocks the device as the medial member is slidingly translated. The lock mechanism 400 also can be a twist lock mechanism featuring a medial sleeve with a helical cut. When the sleeve is rotated, the helical surface acts upon a rotationally fixed cam follower to create linear motion. The lock mechanism 400 also can be a detent mechanism. Other suitable lock mechanisms 400 also can be used.

As shown in FIGS. 139-144, in some embodiments, the magnet-assisted suture grasper 200 can be made further comprising a stabilizer tube 446. As discussed above, a retriever tube 224 made from a hard metal such as stainless steel is stiffer than a retriever tube 224 made from a polymer such as nylon by about two orders of magnitude, and does not require the added support of a stabilizer tube. Although such a retriever tube 224 does not require the added support of a stabilizer tube, a stabilizer tube 446 can be added, for example to provide support for a retriever tube 224 not made from a hard metal.

As shown in FIGS. 139-141, the stabilizer tube 446 comprises a proximal end 448, a proximal hole 450, a distal end 452, and a distal hole 454. In accordance with these embodiments, the retriever tube 224 passes through a lumen of the stabilizer tube 446, and is rigidly fixed to the stabilizer tube 446.

The magnet-assisted suture grasper 200 comprising the stabilizer tube 446 can be configured and operated similarly as the magnet-assisted suture grasper 200 comprising a lock mechanism 400 and a trap wire 304 comprising a grasper arm loop 306 as described above, with the following modifications. The advancer frame 404 and the proximal and distal guide bushings 408 are provided as separate parts. The retriever tube 224 passes through a lumen of the stabilizer tube 446, and is rigidly fixed to the stabilizer tube 446. The end effector 420 is rigidly fixed to the retriever tube 224. The stabilizer tube 446 passes through ventral rings of the advancer frame 404, the proximal and distal guide bushings 408, the spring keeper 412, the drive cam 416, and the lock cam 418, terminating within the body of the proximal hub 220. The proximal hub 220 and the advancer frame 404 are rigidly fixed to the stabilizer tube 446, and the advancer pad 406 is rigidly fixed to the advancer frame 404. The guide bushings 408 are non-rigidly fixed, but are constrained rotationally and laterally by the advancer frame 404, such that these components move in unison as a single unit. The entire advancer assembly slides within the inner channel of the barrel 422 and nose cone 424, such that the return spring 410 compresses between the distal guide bushing 408 and the spring keeper 412 during this motion. During operation, tensile load applied to the magnetic suture 500 is thereby borne by the trap wire 304, which is translated through the trap wire 304 into the retriever tube 224 by way of a rigid joint between these two elements, into the stabilizer tube 446 by way of the joint between these two elements, and into the lock cam 418 by way of the proximal hub 220, which is also rigidly joined to the stabilizer tube 446. The magnet-assisted suture grasper 200 including the stabilizer tube 446 also is designed so that the retriever tube 224 and stabilizer tube 446 run centrally through all components. The lock cam 418 and drive cam 416 are assembled over the stabilizer tube 446, distal to the proximal hub 220 and proximal to the advancer frame 404.

A system for passing a magnetic suture 500 also is disclosed. The system comprises the magnet-assisted suture grasper 200. The system also comprises a magnetic suture 500 comprising a suture magnet 502 and a suture extending from the suture magnet 502.

The magnet-assisted suture grasper disclosed herein can be used for passing a magnetic suture that includes a suture magnet at an end of the suture. Such a magnetic suture can be made, for example, as described in U.S. Pub. No. 2021/0059667. The magnet-assisted suture grasper disclosed herein also can be used for passing a magnetic suture that is magnetic based on including a magnetic metal within the suture.

The magnet-assisted suture grasper disclosed herein may be useful in procedures including, among others: (1) Inguinal hernia repair through high ligation of the patent processus vaginalis as described above; (2) Laparoscopic port closure (typical suture size 2-0 and larger); (3) Microsurgery (typical suture size 7-0 and smaller); (4) General surgery (typical suture size 2-0 to 0); and (5) Orthopedic surgery (typical suture size 0 and larger).

The magnet-assisted suture grasper also may be modified for use in ultrasound-guided surgical techniques. The magnet-assisted suture grasper would be modified by making the distal end of the suture retrieval needle echogenic. This could be done, for example, by applying an echogenic treatment at the distal tip of the suture retrieval needle. The modified magnet-assisted suture grasper would then be used with a hypodermic needle for introducing a suture wherein the hypodermic needle also is echogenic at its distal end. Optionally the magnets of the magnet-assisted suture grasper and the magnetic suture and/or the magnet ferrules and magnetic-suture ferrules that attach the magnets to the wire of the magnet-assisted suture grasper and to the suture also may be made echogenic, for example by applying an echogenic treatment to the magnets and/or the magnet ferrules.

Use of the modified magnet-assisted suture grasper in ultrasound-guided surgical techniques could result in reductions in operative time and complexity by eliminating the need for suction equipment. Suction equipment currently is needed to pass the suture through the needle.

The modified magnet-assisted suture grasper also may allow an alternative technique whereby the suture is dropped off and retrieved from inside the abdominal cavity. This would allow the repair to be completed entirely through a single needle-access point, which would provide improved cosmesis, and could result in less post-operative pain. Under the current laparoscopic approach (termed the PEAR/PIRS technique), the needle is introduced through the skin and directed medial around the defect, exiting inferior to the defect through the peritoneum into the abdominal cavity. Drop-off and retrieval of the suture occurs in this space inside the abdominal cavity. This is not currently possible under ultrasonic guidance because the suture is not echogenic, so the surgeon would have to retrieve the suture from inside the abdominal cavity completely blind. This would be nearly impossible with the current state of suture passer technology (i.e., snares, graspers, etc.). In contrast, the modified magnet-assisted suture grasper may allow this to work, especially if the needle points and ferrules are echogenic.

The magnet-assisted suture grasper described herein could be integrated as end-of-arm tooling for robot-assisted surgery or into the end of an endoscope for direct manipulation of a suture with the endoscope.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

CLAUSES

1. A magnet-assisted suture grasper for grasping a magnetic suture comprising:
   (a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis;
   (b) a retriever tube having a proximal hole, a distal hole, and a retriever tube lumen extending therebetween, the retriever tube being partially disposed within the needle lumen and translatable therein along the needle body axis, the proximal hole of the retriever tube being in fluid communication with the distal hole of the needle body through the retriever tube lumen and the needle lumen;
   (c) a grasper ferrule comprising a proximal end, a distal end, and a ferrule body extending therebetween, the ferrule body having a proximal hole, a distal hole, and a ferrule lumen extending therebetween, the grasper ferrule being fixedly disposed within the retriever tube;
   (d) a grasper member comprising a proximal portion, an intermediate portion, and a distal portion, the grasper member extending distally from the grasper ferrule and being reversibly moveable with respect to the needle lumen between a first position and a second position;
   (e) a grasper magnet being disposed adjacent the intermediate portion of the grasper member, the magnet-assisted suture grasper sequestering the grasper magnet within the needle lumen when the grasper member is in the first position and exposing the grasper magnet from the needle lumen when the grasper member is in the second position; and
   (f) a magnet wire having a proximal portion and a distal portion, the magnet wire extending distally from the grasper ferrule and the grasper magnet being fixedly attached to the distal portion of the magnet wire, either directly or indirectly, wherein:
   the distal portion of the grasper member extends further distally than the grasper magnet,
   translation of the retriever tube within the needle lumen in a first direction along the needle body axis causes the grasper member to move from the first position to the second position, thereby exposing the grasper magnet and allowing contact between the grasper magnet and a magnetic suture attracted thereto, and
   translation of the retriever tube within the needle lumen in a second direction opposite the first direction along the needle body axis causes the grasper member to move from the second position to the first position, thereby sequestering the grasper magnet and grasping the magnetic suture within the needle lumen.
2. The magnet-assisted suture grasper according to clause 1, wherein the suture retrieval needle is a hypodermic needle.
3. The magnet-assisted suture grasper according to clause 1 or clause 2, wherein the suture retrieval needle is straight, the needle body axis thereby being straight.
4. The magnet-assisted suture grasper according to clause 1 or clause 2, wherein the suture retrieval needle is curved, the needle body axis thereby being curved.
5. The magnet-assisted suture grasper according to any one of clauses 1 to 4, wherein the suture retrieval needle has a sharp tip.
6. The magnet-assisted suture grasper according to any one of clauses 1 to 5, wherein magnet-assisted suture grasper further comprises a proximal hub.
7. The magnet-assisted suture grasper according to any one of clauses 1 to 6, wherein the retriever tube comprises stainless steel.
8. The magnet-assisted suture grasper according to any one of clauses 1 to 7, wherein the retriever tube lumen is the only lumen of the retriever tube.
9. The magnet-assisted suture grasper according to any one of clauses 1 to 8, wherein translation of the retriever tube within the needle lumen is limited to a straight path as the translation of the retriever tube causes the grasper member to move between the first and second positions.
10. The magnet-assisted suture grasper according to any one of clauses 1 to 9, wherein:
    the grasper ferrule has been crimped onto the grasper member and the magnet wire, with the proximal portion of the grasper member and the proximal portion of the magnet wire being disposed within the ferrule lumen of the grasper ferrule; and
    the retriever tube has been crimped onto the grasper ferrule, with the grasper ferrule, the proximal portion of the grasper member, and the proximal portion of the magnet wire being disposed within the retriever tube lumen.
11. The magnet-assisted suture grasper according to any one of clauses 1 to 9, wherein the retriever tube has been crimped onto the grasper ferrule, the proximal portion of the grasper member, and the proximal portion of the magnet wire, with the grasper ferrule, the proximal portion of the grasper member, and the proximal portion of the magnet wire being disposed within the retriever tube lumen, and with the proximal portion of the grasper member and the proximal portion of the magnet wire being disposed adjacent the grasper ferrule and not within the ferrule lumen of the grasper ferrule.

12. The magnet-assisted suture grasper according to any one of clauses 1 to 11, wherein the grasper member is more flexible than the needle body.

13. The magnet-assisted suture grasper according to any one of clauses 1 to 12, wherein:
   the grasper member comprises: (i) a grasper wire having a proximal end and a distal end, and (ii) a grasper arm comprising a proximal end, a proximal-to-intermediate portion, a distal portion, and a distal end;
   the grasper wire is fixedly disposed within the grasper ferrule, or adjacent the grasper ferrule and not within the ferrule lumen of the grasper ferrule;
   the grasper wire extends distally from the ferrule lumen;
   the grasper arm extends from the distal end of the grasper wire and is reversibly moveable between the first position and the second position; and
   the grasper magnet is disposed adjacent the proximal-to-intermediate portion of the grasper arm.

14. The magnet-assisted suture grasper according to clause 13, wherein the grasper arm is integral to the grasper wire.

15. The magnet-assisted suture grasper according to clause 13 or clause 14, wherein:
   the grasper member further comprises an enlarged distal terminus at the distal end of the grasper arm;
   the grasper arm is reversibly moveable between the first position and the second position based on translation of the grasper arm from inside of the needle lumen to outside of the needle lumen through the distal hole of the needle body; and
   the enlarged distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

16. The magnet-assisted suture grasper according to clause 13 or clause 14, wherein:
   the grasper member is a first grasper member;
   the grasper wire is a first grasper wire;
   the grasper arm is a first grasper arm;
   the magnet-assisted suture grasper further comprises a second grasper member comprising: (a) a second grasper wire having a proximal end and a distal end, being fixedly disposed within the retriever tube, and extending distally therefrom; and (b) a second grasper arm comprising a proximal end, a proximal-to-intermediate portion, a distal portion, and a distal end, the second grasper arm extending from the distal end of the second grasper wire and being reversibly moveable between the first position and the second position;
   the first and second grasper arms are connected at their distal ends, thereby forming a grasper arm loop;
   the first and second grasper members further comprise an enlarged distal terminus at the distal ends of the first and second grasper arms;
   the grasper arm loop is reversibly moveable between the first position and the second position based on translation of the grasper arm loop from inside of the needle lumen to outside of the needle lumen through the distal hole of the needle body;
   the grasper arm loop circumscribes an area sufficiently large, and the enlarged distal terminus has a size sufficiently small, to allow contact between the grasper magnet and a suture magnet of a magnetic suture attracted thereto when the grasper arm loop is in the second position;
   the enlarged distal terminus has a size sufficiently small to allow a suture of the magnetic suture to pass when the grasper arm loop is in the first position; and
   the enlarged distal terminus has a size sufficiently large to block the suture magnet of the magnetic suture from exiting the needle lumen through the distal hole of the needle body when the grasper arm loop is in the first position.

17. The magnet-assisted suture grasper according to clause 13 or clause 14, wherein:
   the grasper arm is formed from a flat wire having a rectangular cross-section;
   the grasper member further comprises an angled distal terminus at the distal end of the grasper arm;
   the grasper arm is reversibly moveable between the first position and the second position based on translation of the grasper arm from inside of the needle lumen to outside of the needle lumen through the distal hole of the needle body; and
   the angled distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

18. The magnet-assisted suture grasper according to clause 17, wherein the angled distal terminus comprises a hook.

19. The magnet-assisted suture grasper according to clause 17 or clause 18, wherein the angled distal terminus fills 80% or more of an area of the distal hole of the needle body when the grasper arm is in the first position.

20. The magnet-assisted suture grasper according to any one of clauses 1 to 9, wherein:
   the grasper member comprises a grasper arm comprising a proximal end, a proximal-to-intermediate portion, a distal portion, and a distal end;
   the grasper arm is integral to the grasper ferrule; and
   the grasper magnet is disposed adjacent the proximal-to-intermediate portion of the grasper arm.

21. The magnet-assisted suture grasper according to clause 20, wherein:
   the grasper ferrule and the grasper arm are formed from a flat wire having a rectangular cross-section;
   the grasper ferrule comprises opposing first and second portions of the flat wire that have been folded inwardly toward each other, thereby forming the grasper ferrule;

the grasper member further comprises an angled distal terminus at the distal end of the grasper arm;

the grasper arm is reversibly moveable between the first position and the second position based on translation of the grasper arm from inside of the needle lumen to outside of the needle lumen through the distal hole of the needle body; and the angled distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

22. The magnet-assisted suture grasper according to clause 21, wherein the angled distal terminus comprises a hook.

23. The magnet-assisted suture grasper according to clause 21 or clause 22, wherein the angled distal terminus fills 80% or more of an area of the distal hole of the needle body when the grasper arm is in the first position.

24. The magnet-assisted suture grasper according to clause 20, wherein:

the grasper ferrule and the grasper arm are formed from a cut tube comprising a cylindrical portion and a semi-cylindrical portion;

the cylindrical portion of the cut tube comprises the grasper ferrule;

the semi-cylindrical portion of the cut tube comprises the grasper arm;

the grasper member further comprises an angled distal terminus at the distal end of the grasper arm;

the grasper arm is reversibly moveable between the first position and the second position based on translation of the grasper arm from inside of the needle lumen to outside of the needle lumen through the distal hole of the needle body; and the angled distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

25. The magnet-assisted suture grasper according to clause 24, wherein the angled distal terminus comprises a hook.

26. The magnet-assisted suture grasper according to clause 24 or clause 25, wherein the angled distal terminus fills 80% or more of an area of the distal hole of the needle body when the grasper arm is in the first position.

27. The magnet-assisted suture grasper according to any one of clauses 20 to 26, wherein:

the grasper ferrule has been crimped onto the magnet wire with the proximal portion of the magnet wire being disposed within the ferrule lumen of the grasper ferrule; and the retriever tube has been crimped onto the grasper ferrule with the grasper ferrule and the proximal portion of the magnet wire being disposed within the retriever tube lumen.

28. The magnet-assisted suture grasper according to any one of clauses 20 to 26, wherein:

the retriever tube has been crimped onto the grasper ferrule and the proximal portion of the magnet wire, with the grasper ferrule and the proximal portion of the magnet wire being disposed within the retriever tube lumen, and with the proximal portion of the magnet wire being disposed adjacent the grasper ferrule and not within the ferrule lumen of the grasper ferrule.

27. The magnet-assisted suture grasper according to any one of clauses 1 to 26, wherein the magnet wire further comprises a magnet wire distal terminus, the magnet-assisted suture grasper further comprises a magnet ferrule fixedly attached to the magnet wire distal terminus, and the grasper magnet is fixedly attached to the magnet ferrule.

28. The magnet-assisted suture grasper according to any one of clauses 1 to 27, further comprising a lock mechanism that can be reversibly engaged to prevent translation of the retriever tube within the needle lumen in the first direction and/or the second direction.

29. The magnet-assisted suture grasper according to clause 28, wherein the lock mechanism can be reversibly engaged in a first setting that prevents translation of the retriever tube within the needle lumen in the first direction but not the second direction when the distal end of the grasper arm is inside the needle lumen and reversibly engaged in a second setting that prevents translation of the retriever tube within the needle lumen in the first direction but not the second direction when the grasper magnet is outside of the needle lumen.

30. The magnet-assisted suture grasper according to clause 29, wherein maintaining the lock mechanism in the first setting or the second setting does not require energy input.

31. A system for passing a magnetic suture comprising:

the magnet-assisted suture grasper of any one of clauses 1 to 30; and a magnetic suture comprising a suture magnet and a suture extending from the suture magnet.

What is claimed is:

1. A magnet-assisted suture grasper for grasping a magnetic suture comprising:

(a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis;

(b) a retriever tube having a proximal hole, a distal hole, and a retriever tube lumen extending therebetween, the retriever tube being partially disposed within the needle lumen and translatable therein along the needle body axis, the proximal hole of the retriever tube being in fluid communication with the distal hole of the needle body through the retriever tube lumen and the needle lumen;

(c) a grasper ferrule comprising a proximal end, a distal end, and a ferrule body extending therebetween, the ferrule body having a proximal hole, a distal hole, and a ferrule lumen extending therebetween, the grasper ferrule being fixedly disposed within the retriever tube;

(d) a grasper member comprising a proximal portion, an intermediate portion, and a distal portion, the grasper member extending distally from the grasper ferrule and being reversibly moveable with respect to the needle lumen between a first position and a second position;

(e) a grasper magnet being disposed adjacent the intermediate portion of the grasper member, the magnet-assisted suture grasper sequestering the grasper magnet within the needle lumen when the grasper member is in the first position and exposing the grasper magnet from the needle lumen when the grasper member is in the second position; and (f) a magnet wire having a proximal portion and a distal portion, the magnet wire extending distally from the grasper ferrule and the grasper magnet being fixedly attached to the distal portion of the magnet wire, either directly or indirectly, wherein:

the distal portion of the grasper member extends further distally than the grasper magnet, translation of the retriever tube within the needle lumen in a first direction along the needle body axis causes the grasper member to move from the first position to the second position, thereby exposing the grasper magnet and allowing contact between the grasper magnet and a magnetic suture attracted thereto, and translation of the retriever tube within the needle lumen in a second direction opposite the first direction along the needle body axis causes the grasper member to move from the second position to the first position, thereby sequestering the grasper magnet and grasping the magnetic suture within the needle lumen.

2. The magnet-assisted suture grasper according to claim 1, wherein the suture retrieval needle is a hypodermic needle.

3. The magnet-assisted suture grasper according to claim 1, wherein the suture retrieval needle is straight, the needle body axis thereby being straight.

4. The magnet-assisted suture grasper according to claim 1, wherein the suture retrieval needle is curved, the needle body axis thereby being curved.

5. The magnet-assisted suture grasper according to claim 1, wherein the suture retrieval needle has a sharp tip.

6. The magnet-assisted suture grasper according to claim 1, wherein magnet-assisted suture grasper further comprises a proximal hub.

7. The magnet-assisted suture grasper according to claim 1, wherein the retriever tube comprises stainless steel.

8. The magnet-assisted suture grasper according to claim 1, wherein the retriever tube lumen is the only lumen of the retriever tube.

9. The magnet-assisted suture grasper according to claim 1, wherein translation of the retriever tube within the needle lumen is limited to a straight path as the translation of the retriever tube causes the grasper member to move between the first and second positions.

10. The magnet-assisted suture grasper according to claim 1, wherein:

the grasper ferrule has been crimped onto the grasper member and the magnet wire with the proximal portion of the grasper member and the proximal portion of the magnet wire being disposed within the ferrule lumen of the grasper ferrule; and the retriever tube has been crimped onto the grasper ferrule, with the grasper ferrule, the proximal portion of the grasper member, and the proximal portion of the magnet wire being disposed within the retriever tube lumen.

11. The magnet-assisted suture grasper according to claim 1, wherein the retriever tube has been crimped onto the grasper ferrule, the proximal portion of the grasper member, and the proximal portion of the magnet wire, with the grasper ferrule, the proximal portion of the grasper member, and the proximal portion of the magnet wire being disposed within the retriever tube lumen, and with the proximal portion of the grasper member and the proximal portion of the magnet wire being disposed adjacent the grasper ferrule and not within the ferrule lumen of the grasper ferrule.

12. The magnet-assisted suture grasper according to claim 1, wherein the grasper member is more flexible than the needle body.

13. The magnet-assisted suture grasper according to claim 1, wherein:

the grasper member comprises: (i) a grasper wire having a proximal end and a distal end, and (ii) a grasper arm comprising a proximal end, a proximal-to-intermediate portion, a distal portion, and a distal end;

the grasper wire is fixedly disposed within the grasper ferrule, or adjacent the grasper ferrule and not within the ferrule lumen of the grasper ferrule;

the grasper wire extends distally from the ferrule lumen;

the grasper arm extends from the distal end of the grasper wire and is reversibly moveable between the first position and the second position; and the grasper magnet is disposed adjacent the proximal-to-intermediate portion of the grasper arm.

14. The magnet-assisted suture grasper according to claim 13, wherein the grasper arm is integral to the grasper wire.

15. The magnet-assisted suture grasper according to claim 13, wherein:

the grasper member further comprises an enlarged distal terminus at the distal end of the grasper arm;

the grasper arm is reversibly moveable between the first position and the second position based on translation of the grasper arm from inside of the needle lumen to outside of the needle lumen through the distal hole of the needle body; and the enlarged distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

16. The magnet-assisted suture grasper according to claim 13, wherein:

the grasper member is a first grasper member;

the grasper wire is a first grasper wire;

the grasper arm is a first grasper arm;

the magnet-assisted suture grasper further comprises a second grasper member comprising: (a) a second grasper wire having a proximal end and a distal end, being fixedly disposed within the retriever tube, and extending distally therefrom; and (b) a second grasper arm comprising a proximal end, a proximal-to-intermediate portion, a distal portion, and a distal end, the second grasper arm extending from the distal end of the second grasper wire and being reversibly moveable between the first position and the second position;

the first and second grasper arms are connected at their distal ends, thereby forming a grasper arm loop;

the first and second grasper members further comprise an enlarged distal terminus at the distal ends of the first and second grasper arms;

the grasper arm loop is reversibly moveable between the first position and the second position based on translation of the grasper arm loop from inside of the needle lumen to outside of the needle lumen through the distal hole of the needle body;

the grasper arm loop circumscribes an area sufficiently large, and the enlarged distal terminus has a size sufficiently small, to allow contact between the grasper magnet and a suture magnet of a magnetic suture attracted thereto when the grasper arm loop is in the second position;

the enlarged distal terminus has a size sufficiently small to allow a suture of the magnetic suture to pass when the grasper arm loop is in the first position; and the enlarged distal terminus has a size sufficiently large to block the suture magnet of the magnetic suture from exiting the needle lumen through the distal hole of the needle body when the grasper arm loop is in the first position.

17. The magnet-assisted suture grasper according to claim 13, wherein:

the grasper arm is formed from a flat wire having a rectangular cross-section;

the grasper member further comprises an angled distal terminus at the distal end of the grasper arm;

the grasper arm is reversibly moveable between the first position and the second position based on translation of the grasper arm from inside of the needle lumen to outside of the needle lumen through the distal hole of the needle body; and the angled distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

18. The magnet-assisted suture grasper according to claim 17, wherein the angled distal terminus comprises a hook.

19. The magnet-assisted suture grasper according to claim 17, wherein the angled distal terminus fills 80% or more of an area of the distal hole of the needle body when the grasper arm is in the first position.

20. The magnet-assisted suture grasper according to claim 1, wherein:

the grasper member comprises a grasper arm comprising a proximal end, a proximal-to-intermediate portion, a distal portion, and a distal end;

the grasper arm is integral to the grasper ferrule; and the grasper magnet is disposed adjacent the proximal-to-intermediate portion of the grasper arm.

21. The magnet-assisted suture grasper according to claim 20, wherein:

the grasper ferrule and the grasper arm are formed from a flat wire having a rectangular cross-section;

the grasper ferrule comprises opposing first and second portions of the flat wire that have been folded inwardly toward each other, thereby forming the grasper ferrule;

the grasper member further comprises an angled distal terminus at the distal end of the grasper arm;

the grasper arm is reversibly moveable between the first position and the second position based on translation of the grasper arm from inside of the needle lumen to outside of the needle lumen through the distal hole of the needle body; and the angled distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

22. The magnet-assisted suture grasper according to claim 21, wherein the angled distal terminus comprises a hook.

23. The magnet-assisted suture grasper according to claim 21, wherein the angled distal terminus fills 80% or more of an area of the distal hole of the needle body when the grasper arm is in the first position.

24. The magnet-assisted suture grasper according to claim 20, wherein:

the grasper ferrule and the grasper arm are formed from a cut tube comprising a cylindrical portion and a semi-cylindrical portion;

the cylindrical portion of the cut tube comprises the grasper ferrule;

the semi-cylindrical portion of the cut tube comprises the grasper arm;

the grasper member further comprises an angled distal terminus at the distal end of the grasper arm;

the grasper arm is reversibly moveable between the first position and the second position based on translation of the grasper arm from inside of the needle lumen to outside of the needle lumen through the distal hole of the needle body; and the angled distal terminus has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

25. The magnet-assisted suture grasper according to claim 24, wherein the angled distal terminus comprises a hook.

26. The magnet-assisted suture grasper according to claim 24, wherein the angled distal terminus fills 80% or more of an area of the distal hole of the needle body when the grasper arm is in the first position.

27. The magnet-assisted suture grasper according to claim 20, wherein:

the grasper ferrule has been crimped onto the magnet wire with the proximal portion of the magnet wire being disposed within the ferrule lumen of the grasper ferrule; and the retriever tube has been crimped onto the grasper ferrule with the grasper ferrule and the proximal portion of the magnet wire being disposed within the retriever tube lumen.

28. The magnet-assisted suture grasper according to claim 20, wherein:

the retriever tube has been crimped onto the grasper ferrule and the proximal portion of the magnet wire, with the grasper ferrule and the proximal portion of the magnet wire being disposed within the retriever tube lumen, and with the proximal portion of the magnet wire being disposed adjacent the grasper ferrule and not within the ferrule lumen of the grasper ferrule.

29. The magnet-assisted suture grasper according to claim 1, wherein the magnet wire further comprises a magnet wire distal terminus, the magnet-assisted suture grasper further comprises a magnet ferrule fixedly attached to the magnet wire distal terminus, and the grasper magnet is fixedly attached to the magnet ferrule.

30. The magnet-assisted suture grasper according to claim 1, further comprising a lock mechanism that can be reversibly engaged to prevent translation of the retriever tube within the needle lumen in the first direction and/or the second direction.

31. The magnet-assisted suture grasper according to claim 30, wherein the lock mechanism can be reversibly engaged in a first setting that prevents translation of the retriever tube within the needle lumen in the first direction but not the second direction when the distal end of the grasper arm is inside the needle lumen and reversibly engaged in a second setting that prevents translation of the retriever tube within the needle lumen in the first direction but not the second direction when the grasper magnet is outside of the needle lumen.

32. The magnet-assisted suture grasper according to claim 31, wherein maintaining the lock mechanism in the first setting or the second setting does not require energy input.

33. A system for passing a magnetic suture comprising:

the magnet-assisted suture grasper of claim 1; and a magnetic suture comprising a suture magnet and a suture extending from the suture magnet.

* * * * *